(12) United States Patent
Cesa et al.

(10) Patent No.: US 11,191,662 B2
(45) Date of Patent: Dec. 7, 2021

(54) OSTOMY DEVICE, APPARATUS, AND SYSTEM

(71) Applicant: Avent, Inc., Alpharetta, GA (US)

(72) Inventors: Joseph A. Cesa, Franklin, MA (US); Nathan C. Griffith, Johns Creek, GA (US); Benone Tarcau, Buford, GA (US); James Zacha, Cumming, GA (US); Donald McMichael, Roswell, GA (US)

(73) Assignee: Avent, Inc., Alpharetta, GA (US)

(*) Notice: Subject to any disclaimer, the term of this patent is extended or adjusted under 35 U.S.C. 154(b) by 683 days.

(21) Appl. No.: 15/773,629

(22) PCT Filed: Nov. 4, 2016

(86) PCT No.: PCT/US2016/060487
§ 371 (c)(1),
(2) Date: May 4, 2018

(87) PCT Pub. No.: WO2017/079533
PCT Pub. Date: May 11, 2017

(65) Prior Publication Data
US 2019/0060105 A1 Feb. 28, 2019

Related U.S. Application Data

(60) Provisional application No. 62/251,746, filed on Nov. 6, 2015.

(51) Int. Cl.
*A61F 5/449* (2006.01)
*A61F 5/44* (2006.01)
(Continued)

(52) U.S. Cl.
CPC .............. *A61F 5/448* (2013.01); *A61F 5/44* (2013.01); *A61F 5/445* (2013.01); *A61F 5/4405* (2013.01);
(Continued)

(58) Field of Classification Search
CPC combination set(s) only.
See application file for complete search history.

(56) References Cited

U.S. PATENT DOCUMENTS 4,041,203 A * 8/1977 Brock ............... B32B 5/08
428/157
4,351,322 A 9/1982 Prager
(Continued)

FOREIGN PATENT DOCUMENTS

EP 1 741 464 A2 1/2007
GB 2247192 A 2/1992
(Continued)

OTHER PUBLICATIONS

International Search Report and Written Opinion for PCT/US2016/060487, dated Feb. 6, 2017, 12 pages.
(Continued)

*Primary Examiner* — Guy K Townsend
(74) *Attorney, Agent, or Firm* — Dority & Manning, P.A.

(57) ABSTRACT

Devices for insertion into a stoma formed in a patient's body are provided, comprising a tube having distal and proximal ends and defining a path for movement of waste. To retain the device in the stoma and seal the stoma, the tube includes a retention mechanism located on the distal end and/or a sealing mechanism extending along a length of the tube between the proximal and distal ends. Collection apparatus for collecting waste from a patient's body also are provided, comprising a waste pouch and a connector for connecting the collection apparatus to a device inserted into a stoma.

(Continued)

Additionally, waste collection systems for collecting waste from a patient's body are provided, comprising a tube for insertion into a stoma and a waste pouch. Each system may comprise a separate tube and waste pouch or the tube and waste pouch may be formed as an integral, inseparable component.

20 Claims, 27 Drawing Sheets

(51) Int. Cl.
  *A61F 5/445* (2006.01)
  *A61M 25/10* (2013.01)
  *A61F 5/448* (2006.01)
(52) U.S. Cl.
  CPC ............ *A61F 5/4408* (2013.01); *A61F 5/449* (2013.01); *A61M 25/10* (2013.01); *A61M 25/10185* (2013.11)

(56) References Cited

U.S. PATENT DOCUMENTS

| | | | | |
|---|---|---|---|---|
| 4,555,242 | A * | 11/1985 | Saudagar | A61F 5/445 604/103.08 |
| 4,941,869 | A * | 7/1990 | D'Amico | A61F 5/445 600/32 |
| 5,364,378 | A | 11/1994 | Denard | |
| 6,033,390 | A * | 3/2000 | von Dyck | A61F 5/441 600/29 |
| 6,350,255 | B1 * | 2/2002 | von Dyck | A61F 5/441 604/332 |
| 6,485,476 | B1 * | 11/2002 | von Dyck | A61F 5/441 604/332 |
| 6,526,977 | B1 | 3/2003 | Göbel | |
| 6,689,111 | B2 * | 2/2004 | Mulhauser | A61F 5/445 604/332 |
| 6,802,317 | B2 | 10/2004 | Göbel | |
| 7,001,367 | B2 * | 2/2006 | Arkinstall | A61F 5/445 604/337 |
| 8,070,737 | B2 * | 12/2011 | Cline | A61F 5/445 604/338 |
| 8,167,859 | B2 * | 5/2012 | Shah | B29C 51/267 604/339 |
| 8,323,254 | B2 * | 12/2012 | Tsai | B32B 1/08 604/317 |
| 8,388,586 | B2 * | 3/2013 | Weig | A61F 5/451 604/338 |
| 8,821,464 | B2 * | 9/2014 | Hanuka | A61F 5/44 604/333 |
| 8,845,607 | B2 | 9/2014 | Hanuka et al. | |
| 9,345,612 | B2 * | 5/2016 | Hanuka | A61F 5/445 604/342 |
| 9,636,249 | B2 * | 5/2017 | Davies | A61F 5/445 604/342 |
| 9,707,120 | B2 * | 7/2017 | Nguyen-DeMary | A61F 5/4407 604/342 |
| 2002/0077611 | A1 * | 6/2002 | von Dyck | A61F 5/445 604/333 |
| 2003/0181879 | A1 * | 9/2003 | Mulhauser | A61F 5/445 604/332 |
| 2003/0187393 | A1 * | 10/2003 | Cline | A61F 5/448 604/131 |
| 2003/0220621 | A1 * | 11/2003 | Arkinstall | A61F 5/445 604/335 |
| 2005/0261646 | A1 | 11/2005 | Conrad et al. | |
| 2007/0191794 | A1 * | 8/2007 | Cline | A61F 5/445 604/335 |
| 2008/0103463 | A1 * | 5/2008 | Tsai | B32B 7/12 604/317 |
| 2008/0262449 | A1 * | 10/2008 | Shah | B29C 66/232 604/339 |
| 2009/0275795 | A1 * | 11/2009 | Martino | A61F 5/445 600/32 |
| 2010/0069859 | A1 * | 3/2010 | Weig | A61F 2/0027 604/335 |
| 2010/0241092 | A1 * | 9/2010 | Nguyen-DeMary | A61P 31/00 604/336 |
| 2010/0280489 | A1 * | 11/2010 | Nishtala | A61M 3/0283 604/514 |
| 2011/0147114 | A1 * | 6/2011 | Bain | A61F 5/441 181/198 |
| 2013/0060212 | A1 | 3/2013 | Hanuka et al. | |
| 2013/0304008 | A1 * | 11/2013 | Hanuka | A61F 5/448 604/334 |
| 2014/0213995 | A1 | 7/2014 | Garrettson | |
| 2014/0323990 | A1 * | 10/2014 | Nishtala | A61M 3/0287 604/265 |
| 2015/0065971 | A1 * | 3/2015 | Goldsmith | A61F 5/448 604/342 |
| 2017/0312115 | A1 * | 11/2017 | Nguyen-DeMary | A61F 5/441 604/342 |
| 2019/0060104 | A1 * | 2/2019 | Cesa | A61F 5/445 604/342 |
| 2019/0060105 | A1 * | 2/2019 | Cesa | A61F 5/4405 604/342 |

FOREIGN PATENT DOCUMENTS

| | | |
|---|---|---|
| JP | 3017308 U | 10/1995 |
| JP | H 07-1161898 | 3/1999 |
| JP | 2014023605 A | 2/2014 |
| WO | WO 01/49224 A1 | 7/2001 |
| WO | WO 2005/063152 A1 | 7/2005 |
| WO | WO 2011/007355 A2 | 1/2011 |

OTHER PUBLICATIONS

Translation of Japanese Office Action dated Dec. 8, 2020, 7 pages.

* cited by examiner

OSTOMY DEVICE, APPARATUS, AND SYSTEM

CROSS-REFERENCE TO RELATED APPLICATIONS

The present application is the national stage entry of International Patent Application No. PCT/US2016/060487 having a filing date of Nov. 4, 2016, which claims priority to U.S. Provisional Application Ser. No. 62/251,746, filed on Nov. 6, 2015, both of which are incorporated herein in their entirety by reference thereto.

FIELD OF THE INVENTION

The subject matter of the present disclosure relates generally to devices for placement within a stoma in the body of a patient and, more particularly, to ostomy devices for placement within a stoma to facilitate the removal of waste from the body of a patient.

BACKGROUND

Due to one or more disease states that prevent disposing of waste naturally, a patient living with an ostomy such as, e.g., a colostomy, ileostomy, or urostomy, has a portion of the patient's lower gastrointestinal organs pulled through the patient's abdominal wall and external to the patient's body to enable the patient's body to dispose of waste. Unfortunately, a stoma site created by these ostomies commonly has one or more complications including, e.g., infection, irritation, odor, leakage, and embarrassment to the patient. These problems can be further exacerbated by additional variables. Typically, an ostomy or waste bag or pouch is used to collect the waste, and the ostomy pouch is fastened to the patient's body with an adhesive that is placed directly over the stoma site. Thus, the stoma site is exposed to constant pushing and pulling of adhesive around it and must also bear the weight of the ostomy pouch pulling on the site. Further, the waste dumps directly out of the stoma into the ostomy pouch and waste and/or effluent may leak from the stoma, such that the stoma site is exposed to acids and feces. Therefore, on a daily basis, the patient must follow a rigorous and undesirable process of cleaning the stoma site to prevent infection, irritation, or the like. Additionally, gases such as, e.g., air and sulphuric gas, can accumulate in the pouch and cause the pouch to balloon or expand and cause odors. These several variables and concerns, in addition to complications associated with the stoma itself, are major contributors to deterioration of the health of the stoma, as well as the patient's quality of life.

Consequently, there is a need for a waste disposal device that substantially reduces or eliminates these variables and concerns. In particular, a device configured to be placed directly into a stoma site and retained internally to an organ's natural path would be beneficial. More specifically, a device that seals a waste path from a gastrointestinal organ that enables material to move only out of the device and not contact an external portion of the organ would be advantageous. More generally, a device that prevents leakage from the stoma would be desirable. Additionally, a device that eliminates the need for adhesives for retention of a waste pouch would be useful. Further, a waste pouch system that does not fasten over the top of a stoma site also would be helpful. Moreover, a waste pouch that is selectively permeable to filter gases from the pouch would be beneficial.

SUMMARY

The present invention provides devices for insertion into a stoma formed in a body of a patient. Each device comprises a tube defining a path for movement of waste, as well as a retention mechanism located on a distal end of the tube and/or a sealing mechanism extending along a length of the tube between a proximal end and a distal end. The retention mechanism and/or sealing mechanism may help retain the device in the stoma and seal a pathway formed by the stoma against movement of waste through the stoma rather than the tube. The present invention also provides collection apparatus for collecting waste from a body of a patient. Each collection apparatus comprises a waste pouch for collecting waste and a connector for connecting the collection apparatus to a device inserted into a stoma formed in a body of a patient. Further, the present invention provides waste collection systems for collecting waste from a body of a patient. Each system comprises a tube for insertion into a stoma formed in the body and a waste pouch for collecting waste from the body. Each system may comprise a separate tube and waste pouch or the tube and waste pouch may be formed as an integral, inseparable component. Additional aspects and advantages of the invention will be set forth in part in the following description, may be apparent from the description, or may be learned through practice of the invention.

In one aspect, the present subject matter is directed to a device for insertion into a stoma formed in a body of a patient. The device defines an axial direction and has a distal end and a proximal end spaced apart along the axial direction. The device comprises a tube extending along the axial direction from the distal end to the proximal end. The tube defines a path for movement of waste. The device also includes a sealing mechanism extending axially along a length of the tube between the proximal end and the distal end of the tube. The sealing mechanism has an insertion position and a sealing position, and the sealing mechanism expands against a surface of the stoma in the sealing position.

It should be understood that the device may be further configured with any of the additional features as described herein. For example, the sealing mechanism may be an inflatable sealing balloon that is deflated in the insertion position and inflated in the sealing position. In some embodiments, the sealing balloon is a thin-wall, high-volume, low-pressure cuff. The sealing balloon may have an inflated diameter and the tube may have an outer diameter, and in some embodiments, the inflated diameter of the sealing balloon is from 1.2 to 1.5 times the outer diameter of the tube.

In other embodiments of the device, the device includes a retention mechanism at the distal end of the tube. The retention mechanism has an insertion position and a retention position. In some embodiments, the retention mechanism is an inflatable retention balloon that is deflated in the insertion position of the retention mechanism and inflated in the retention position of the retention mechanism. Further, the retention balloon may have an inflated diameter and the tube may have an outer diameter, and in some embodiments, the inflated diameter of the retention balloon is at least twice the outer diameter of the tube.

In embodiments in which the device comprises retention and sealing balloons, the device may include a first inflation valve for inflating the sealing balloon and a second inflation valve for inflating the retention balloon. Further, in some embodiments, the proximal end of the tube receives a connector of a waste collection apparatus, which extends the path for movement of the waste into the waste collection apparatus. In other embodiments, a waste collection pouch is integrally formed with the tube.

In another aspect, the present subject matter is directed to a device for insertion into a stoma formed in a body of a patient. The device defines an axial direction and has a distal end and a proximal end spaced apart along the axial direction. The device comprises a tube extending along the axial direction between the distal end and the proximal end; the tube defines a path for movement of waste. The device also includes a sealing mechanism extending axially along an external length of the tube between the proximal end and the distal end of the tube and a retention mechanism positioned at the distal end of the tube. The sealing mechanism has an insertion position and a sealing position, and the retention mechanism has an insertion position and a retention position. The sealing mechanism expands against the stoma in the sealing position, and the retention mechanism expands to a diameter greater than the diameter of the stoma in the retention position.

It should be understood that the device may be further configured with any of the additional features as described herein. As an example, the sealing mechanism may be an inflatable sealing balloon that is deflated in the insertion position and inflated in the sealing position. In some embodiments, the sealing balloon is a thin-wall, high-volume, low-pressure cuff. The sealing balloon may have an inflated diameter and the tube may have an outer diameter, and in some embodiments, the inflated diameter of the sealing balloon is from 1.2 to 1.5 times the outer diameter of the tube.

Further, in some embodiments the retention mechanism of the device is an inflatable retention balloon that is deflated in the insertion position of the retention mechanism and inflated in the retention position of the retention mechanism. The retention balloon may have an inflated diameter and the tube may have an outer diameter, and in some embodiments, the inflated diameter of the retention balloon is at least twice the outer diameter of the tube.

In embodiments in which the device comprises retention and sealing balloons, the device may include a first inflation valve for inflating the sealing balloon and a second inflation valve for inflating the retention balloon. Alternatively, the device may include an inflation valve for inflating both the sealing balloon and the retention balloon.

Moreover, in some embodiments, the device also includes a waste collection apparatus. For example, the proximal end of the tube receives a connector of a waste collection apparatus to couple the waste collection apparatus to the device, which extends the path for movement of the waste into the waste collection apparatus. Alternatively, a waste collection pouch is integrally formed with the tube.

In other embodiments, the tube is a thin walled tube. The tube may have other configurations as well.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

Figure 1:
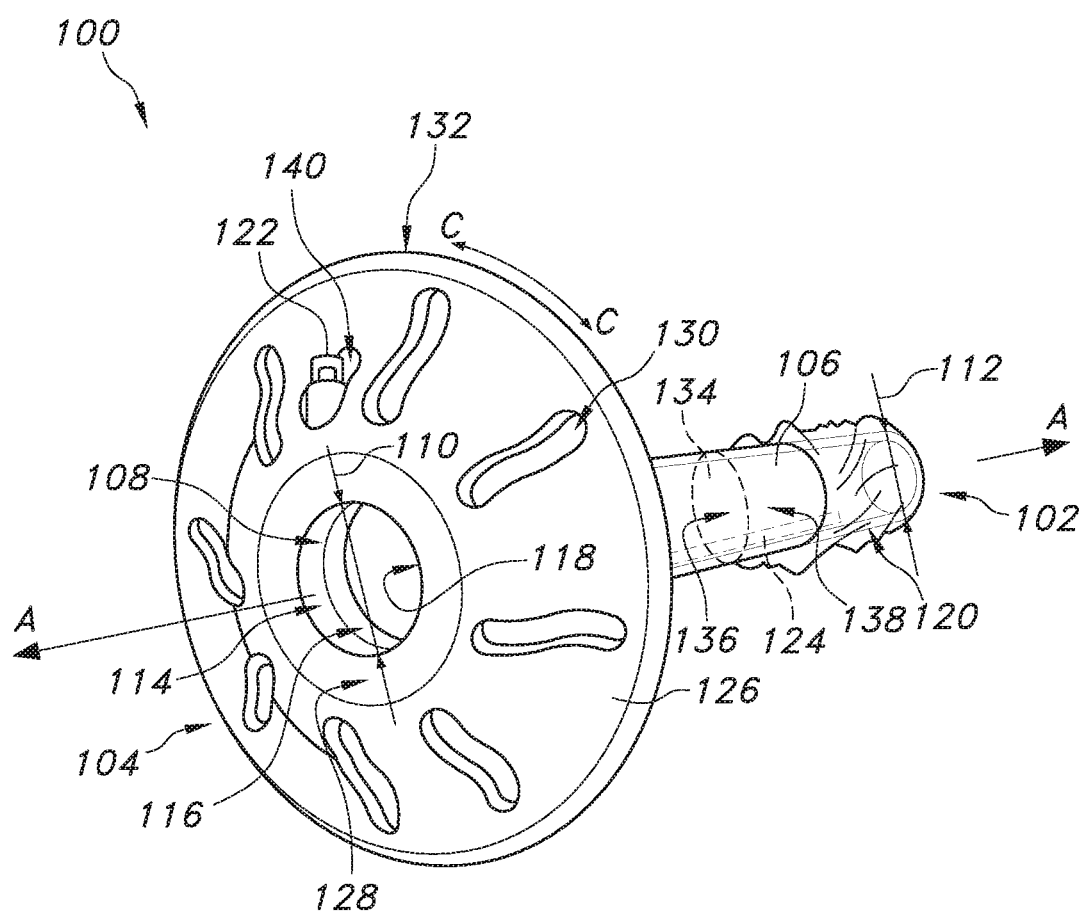
FIG. 1 provides a perspective view of a device for insertion into a stoma formed in a body of a patient, according to an exemplary embodiment of the present subject matter, in which a retention mechanism of the device is in an insertion position.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Moreover, the particular naming of the components, capitalization of terms, the attributes, data structures, or any other programming or structural aspect is not mandatory or significant, and the mechanisms that implement the invention or its features may have different names, formats, or protocols. Also, the particular division of functionality between the various components described herein is merely exemplary and not mandatory; functions performed by a single component may instead be performed by multiple components, and functions performed by multiple components may instead performed by a single component.

Figure 2:
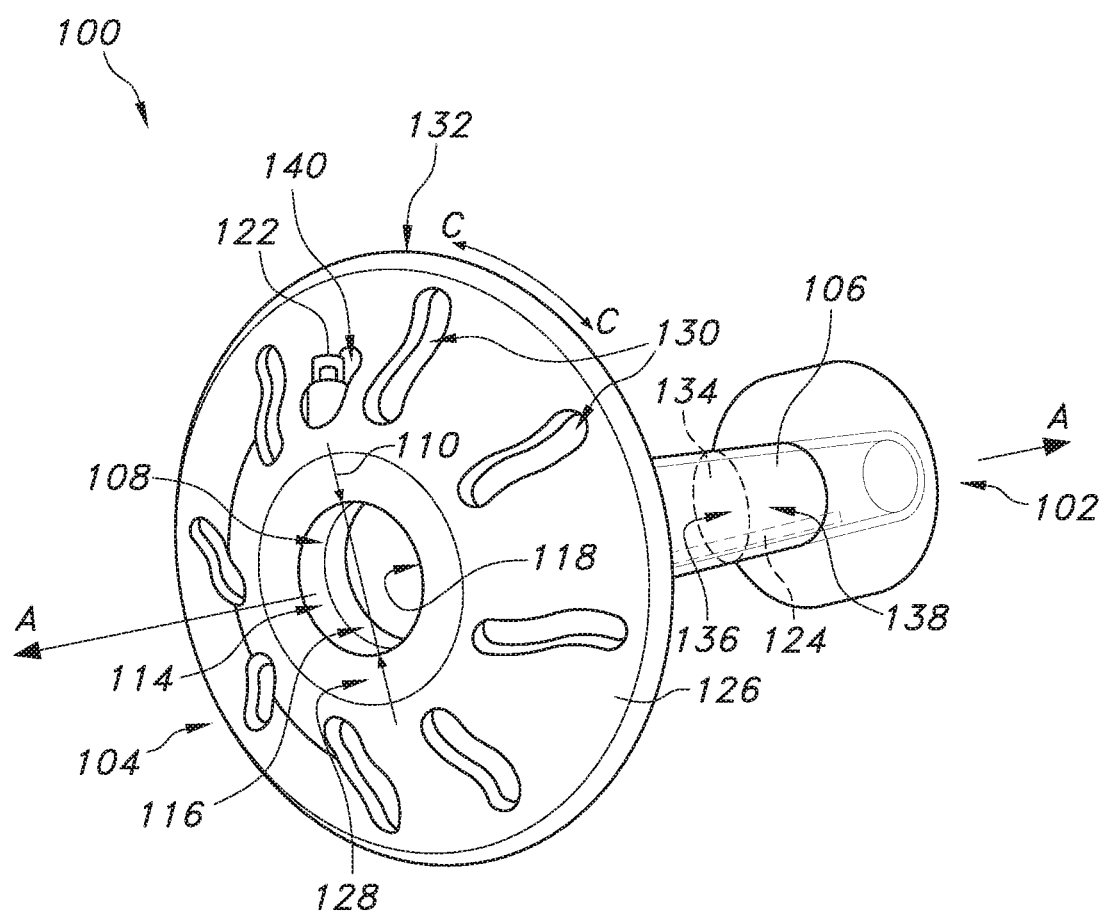
FIG. 2 provides a perspective view of the device of FIG. 1 in which the retention mechanism of the device is in a retention position.

FIG. 1 provides a perspective view of a device for insertion into a stoma formed in a body of a patient, according to an exemplary embodiment of the present subject matter, in which a retention mechanism of the device is in an insertion position. FIG. 2 illustrates the device of FIG. 1 with the retention mechanism of the device in a retention position. As shown in FIGS. 1 and 2, the device 100 defines an axial direction A and has a distal end 102 and a proximal end 104. Distal end 102 is spaced apart from proximal end 104 along the axial direction A.

Device 100 includes a tube 106 extending along the axial direction A between distal end 102 and proximal end 104 of device 100. Tube 106 defines a path 108 for movement of waste or effluent, e.g., for movement of waste, such as, e.g., urine, stool, or mucus, through the stoma as described in greater detail below. In some embodiments, tube 106 is tapered from proximal end 104 toward distal end 102. In such embodiments, tube 106 may have a first diameter 110 at proximal end 104 and a second diameter 112 at distal end 102, and first diameter 110 is larger or greater than second diameter 112 such that tube 106 decreases in diameter from proximal end 104 to distal end 102. In other embodiments, second diameter 112 may be different from first diameter 110 but tube 106 may not taper from proximal end 104 to distal end 102. For example, second diameter 112 may be larger than first diameter 110 or tube 106 may have a larger or smaller diameter at one or more locations along tube 106 between proximal end 104 and distal end 102. In still other embodiments, the tube 106 may have a constant diameter from the proximal end 104 to the distal end 102. Further, in various embodiments, tube 106 may be rigid, flexible, or fully or partially collapsible; expandable, non-expandable, or partially expandable; soft or hard; or any appropriate combination of the foregoing. Moreover, tube 106 may be relatively thin walled, e.g., to permit as large of an inner diameter and/or cross-sectional area as possible for the movement of waste through tube 106. Tube 106 may have other configurations as well.

Referring still to FIGS. 1 and 2, in the depicted embodiment of device 100, tube 106 defines a connection portion 114 near proximal end 104. Connection portion 114 includes a groove 116 defined along an inner surface 118 of tube 106. As will be further describe below, groove 116 may be configured to receive a protrusion of a waste collection bag or pouch to connect the pouch to device 100 and seal the connection such that waste may move through tube 106 to the waste pouch without leaking through the connection between the pouch and the device. In other embodiments, connection portion 114 may have other configurations to mechanically or otherwise fasten or attach a waste pouch or other apparatus to device 100.

Figure 3:
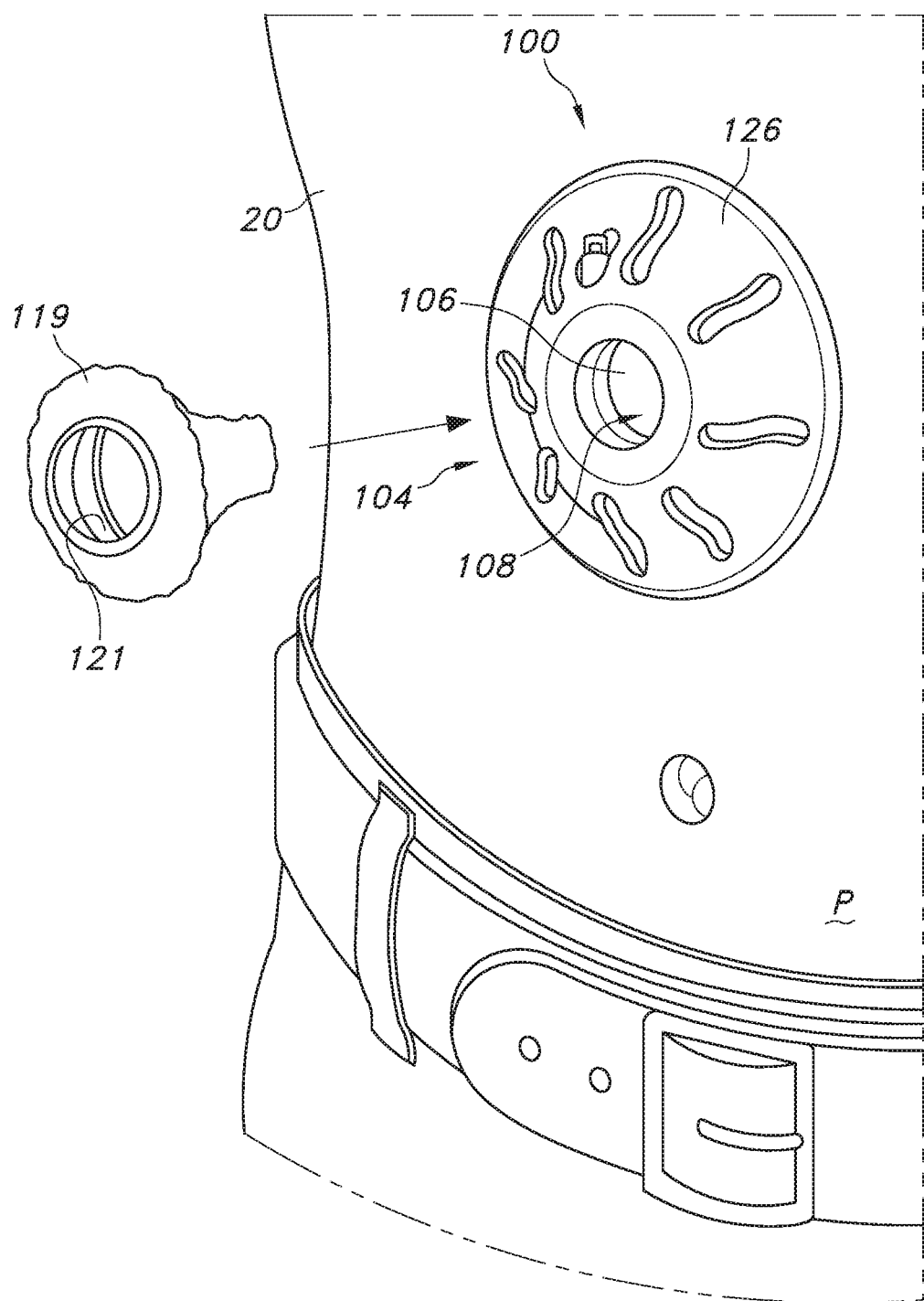
FIG. 3 provides a schematic illustration of the installation of a cap into the device of FIG. 1, where the device of FIG. 1 has been inserted into a stoma formed in a body of a patient.
Figure 4:
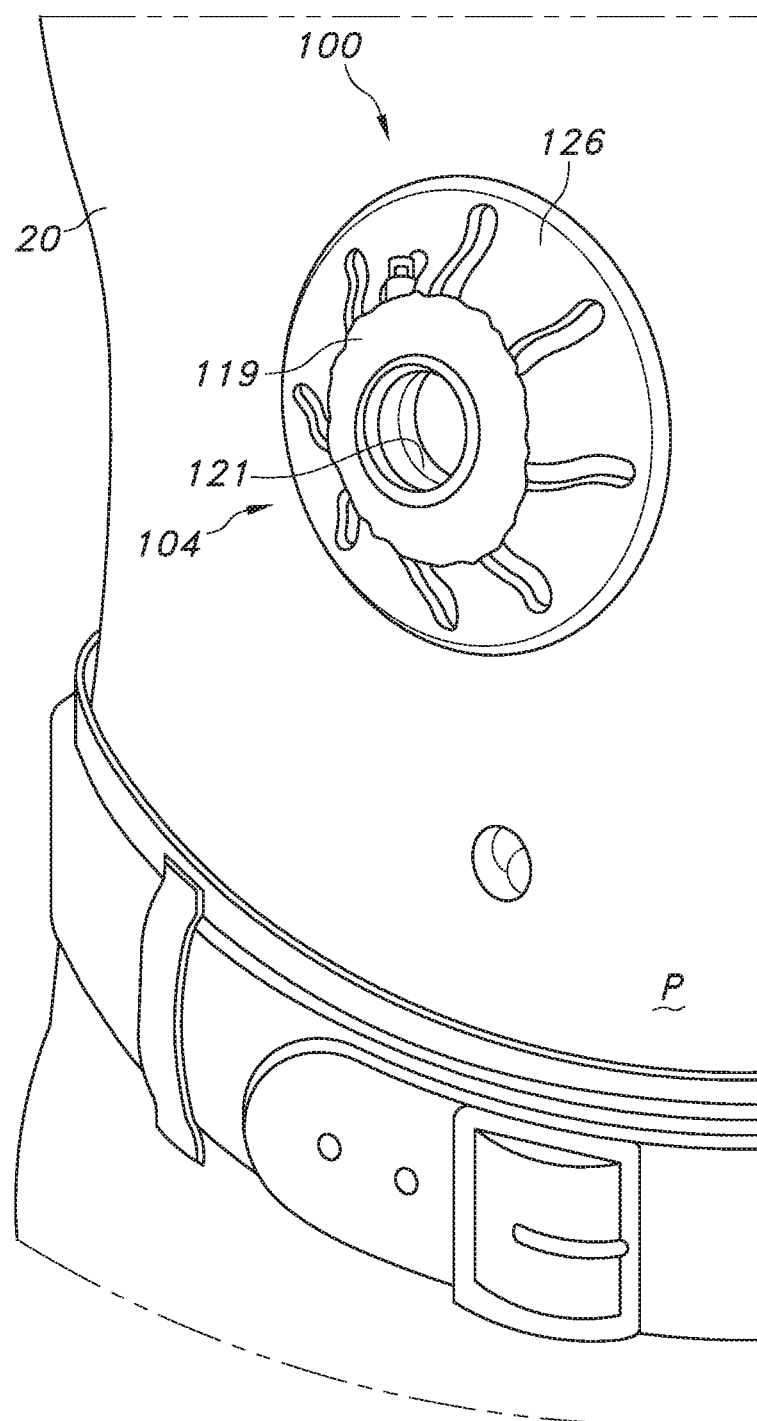
FIG. 4 provides an illustration of the cap of FIG. 3 inserted into the device of FIG. 1.

In some embodiments, device 100 may include a removable cap 119 for selectively sealing the proximal end 104 of path 108 defined by tube 106. Cap 119 may have any appropriate configuration for sealing path 108, e.g., when a waste pouch is not attached to device 100. For example, in one embodiment, cap 119 may be configured to interface with connection portion 114 of tube 106 to close or seal path 108. In a particular embodiment, cap 119 may include a protrusion that fits within groove 116 to create a fluid tight seal between cap 119 and tube 106. In an exemplary embodiment, as shown in FIGS. 3 and 4, cap 119 may be an absorbent plug configured to fit into tube 106 to seal path 108. The depicted cap 119 includes a grip portion 121 to help the patient or other user grip cap 119 for insertion into or removal from tube 106. Additionally, in some embodiments, cap 119 may be tethered to device 100 such that cap 119 is readily available to seal path 108, e.g., when a waste pouch is not attached to device 100. Those of ordinary skill in the art will readily understand that cap 119 also may have other configurations to seal or cap off path 108 to prevent the movement of waste through or out of proximal end 104 of tube 106.

A retention mechanism 120 is located on tube 106 near distal end 102. As illustrated, retention mechanism 120 has an insertion position, shown in FIG. 1, and a retention position, shown in FIG. 2. In the depicted embodiment, retention mechanism 120 is an inflatable balloon or cuff, such as a Microcuff® balloon by Halyard Health of Alpharetta, Ga. Such inflatable balloons or cuffs have been shown to create effective sealing against pathway walls and to reduce leakage around the balloon at the walls. In such embodiments, the balloon is deflated when in the insertion position and inflated when in the retention position. An inflation valve 122 and an inflation line 124 may be provided for inflating the balloon. As shown in FIGS. 1 and 2, inflation valve 120 may be positioned at a flange or barrier 126 included at proximal end 104 of device 100. Of course, other configurations of inflation valve 122 and inflation line 124 also may be used, e.g., inflation line 124 may be incorporated into tube 106. It also will be readily understood by those of ordinary skill in the art that other retention mechanisms 120 may be used as well, such as a flexible diaphragm or other mechanical means of retention and sealing.

Continuing with FIGS. 1 and 2, barrier 126 defines a proximal surface 128 at proximal end 104 of device 100. As depicted, barrier 126 is generally circular in shape and defines a circumferential direction C. More particularly, as shown in FIGS. 1 and 2, barrier 126 has a generally domed shape such that a perimeter 132 of barrier 126 is spaced from proximal end 104 along the axial direction A toward distal end 102. Barrier 126 smoothly transitions from proximal surface 128 to perimeter 132 spaced apart from proximal surface 128 along the axial direction A. Barrier 126 further defines a plurality of vents 130 about the circumferential direction C, but in other embodiments, barrier 126 defines at least one vent 130. In still other embodiments, vents 130 may be omitted.

Preferably, barrier 126 is flexible to provide access to an area beneath the barrier. That is, flexible barrier 126 may be bent or rolled back, e.g., along the axial direction A away from distal end 102, such that an area otherwise covered by barrier 126 may be accessed. In some embodiments, barrier 126 may be made from an elastomeric material that allows barrier 126 to flex. Barrier 126 may be made from other suitable materials as well, and in appropriate embodiments, barrier 126 may be inflexible.

Device 100 also may include a valve 134 positioned in path 108. Valve 134 may selectively permit movement of waste through tube 106 along path 108. As further described below, valve 134 may permit movement of waste through tube 106 when a waste collection pouch is connected to device 100 but may prohibit movement of waste through tube 106 when no waste collection pouch is connected. In an exemplary embodiment, valve 134 is positioned in path 108 such that a first side 136 of valve 134 is positioned toward proximal end 104 of device 100 and a second side 138 of valve 134 is positioned toward distal end 102 of device 100. Device 100 may further comprise a pressure gauge 140 for indicating a pressure at second side 138 of valve 134. More specifically, pressure gauge 140 can indicate changes in pressure within path 108 upstream of valve 134, where second side 138 disposed toward distal end 102 is upstream of valve 134. As an example, an increase in the upstream pressure in path 108 may indicate that waste is present behind valve 134 that needs to be removed or emptied. Pressure gauge 140 may indicate other conditions as well. In one embodiment, pressure gauge 140 is disposed at or near inflation valve 122, but pressure gauge 140 may be disposed at other locations as well. Other configurations of valve 134 and pressure gauge 140 also may be used, and in some embodiments of device 100, similar components may be substituted for valve 134 and pressure gauge 140. In still other embodiments, valve 134 and/or pressure gauge 140 may be omitted.

Figure 5:
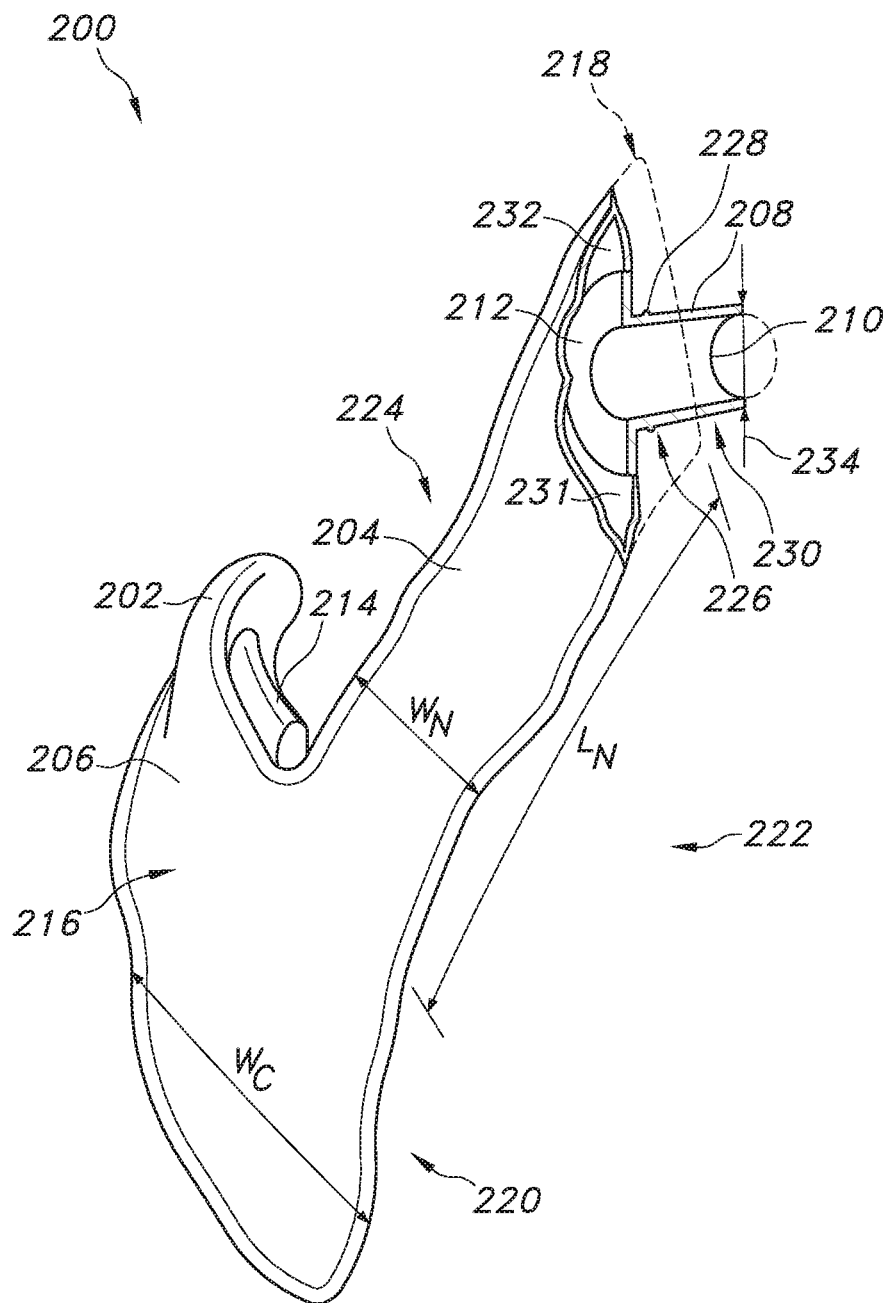
FIG. 5 provides a perspective view of a collection apparatus for collecting waste moving through a stoma formed in a body of a patient, according to an exemplary embodiment of the present subject matter.

Referring now to FIG. 5, a perspective view is provided of a collection apparatus for collecting waste moving through a stoma formed in a body of a patient, according to an exemplary embodiment of the present subject matter. The collection apparatus 200 includes a waste bag or a waste pouch 202, having a neck portion 204 and a container portion 206, and a connector 208, having a tubular portion 210 and a flange portion 212. Waste pouch 202 collects waste rejected from the body through the stoma formed in the body.

Collection apparatus 200 also may include an attachment mechanism 214 for attaching collection apparatus 200 to a support. For example, as described in greater detail herein, using attachment mechanism 214, collection apparatus 200 may be attached to a support—such as, e.g., the patient's clothing or a healthy portion of the patient's body away from the stoma—that can help support the weight of collection apparatus 200, particularly when it is filled with waste. Attachment mechanism 214 may be coupled to an outer surface 216 of waste pouch 202, e.g., at container portion 206 of pouch 202 as depicted, using any appropriate fastener or fastening mechanism. Additionally, attachment mechanism 214 may be any appropriate mechanism for attaching collection apparatus 200 to a support. For example, attachment mechanism 214 may be a stretchable, elastic loop; a hook-and-loop type fastener; an adhesive; or any other appropriate mechanism for attaching collection system 200 to a support.

For illustrative purposes, a segment of waste pouch 202 has been removed in FIG. 5 to show that connector 208 is attached to waste pouch 202. More particularly, connector 208 is attached to waste pouch 202 at flange portion 212 of connector 208 such that a fluid tight seal is formed between flange portion 212 and waste pouch 202. That is, waste pouch 202 and connector 208 are coupled such that fluid cannot leak at the attachment point between waste pouch 202 and connector 208. In some embodiments, waste pouch 202 and connector 208 may be mechanically coupled or thermally bonded to one another. In still other embodiments, an appropriate adhesive may be used to couple waste pouch 202 and connector 208. Any other appropriate means also may be used to attach waste pouch 202 to connector 208 such that a fluid tight seal is formed between the two components.

Referring still to FIG. 5, the depicted embodiment shows neck portion 204 of waste pouch 202 has a first end 218 and a second end 220 separated by a length $L_N$. As illustrated, connector 208 is attached to waste pouch 202 at first end 218 of neck portion 204. Container portion 206 is defined at second end 220 of neck portion 204 such that container portion 206 is separated from connector 208 generally by the length $L_N$ of neck portion 204. Further, neck portion 204 has a width $W_N$ and container portion 206 has a width $W_C$. In the depicted embodiment, width $W_C$ of container portion 206 is greater than width $W_N$ of neck portion 204, but in other embodiments, the widths $W_C$, $W_N$ may be equal or width $W_N$ may be greater than width $W_C$. As also shown in FIG. 5, neck portion 204 is defined on a right side 222 of waste pouch 202. Alternatively, neck portion 204 may be defined such that neck portion 204 and container portion 206 are centered with respect to each other, e.g., a centerline of neck portion 204 is aligned with a centerline of container portion 206, or neck portion 204 may be defined on a left side 224 of waste pouch 202.

Referring particularly to connector 208, tubular portion 210 defines a connection portion 226. Connection portion 226 of connector 208 includes a protrusion 228 extending about an outer surface 230 of tubular portion 210. As generally described above, groove 116 may be configured to receive protrusion 228 of connector 208 to connect waste pouch 202 to device 100 and to seal the connection. Thereby, when waste pouch 202 is sealingly connected to device 100, waste may move through tube 106 to waste pouch 202 without leaking through the connection between connector 208 of collection apparatus 200 and tube 106 of device 100. Connection portion 114 of device 100 and connection portion 226 of collection apparatus 200 generally may be described as a connection assembly, where groove 116 is a female portion of the mechanical assembly and protrusion 228 is a male portion of the assembly. In alternative embodiments, connection portion 114 of device 100 may define the male portion of the connection assembly and connection portion 226 of collection apparatus 200 may define the female portion of the assembly. Of course, as previously described, connection portion 114 may have other configurations and, similarly, connection portion 226 may have other configurations to mechanically or otherwise fasten or attach waste pouch 202 to device 100 or another device.

Collection apparatus 200 may incorporate one or more features for controlling odors, wet spots, irritation, or other undesirable conditions. For example, an inner surface 231 of waste pouch 202 may comprise a layer 232 of liquid impervious film, which can help prevent liquids from soaking through waste pouch 202 and creating wet spots on the patient's body, clothing, or the like. Additionally or alternatively, waste pouch 202 may be coated with a material or formulation, or the material or formulation may be integrated into the material of waste pouch 202, that is selectively permeable to one or more gases. For example, the coating may permit air to pass through waste pouch 202 to help prevent pouch 202 from ballooning or swelling such that, e.g., pouch 202 may remain relatively inconspicuous. However, while allowing air to pass through, the coating may inhibit the flow of, e.g., sulphuric gases to help prevent odors from waste collected in waste pouch 202. Other coatings, films, or the like also may be used to prevent undesirable conditions of collection system 200.

Further, in the depicted exemplary embodiment, waste pouch 202 comprises a nonwoven material such as a spunbonded-meltblown-spunbonded ("SMS") material. More particularly, outer surface 216 of waste pouch 202 may be made from a SMS material such that collection apparatus 200 has a soft shell, which can improve patient comfort, e.g., when collection system 200 is in contact with the patient's skin, without sacrificing other desirable properties of the waste pouch material. Nonwoven materials may be particularly appropriate for the construction of waste pouch 202 due to, e.g., the barrier properties, economics, and consistent quality of nonwovens. Nonwoven materials can be made from a variety of processes including, but not limited to, air laying processes, wet laid processes, hydroentangling processes, spunbonding, meltblowing, staple fiber carding and bonding, and solution spinning. The fibers themselves can be made from a variety of both natural and synthetic materials including, but not limited to, cellulose, rayon, nylon, polyesters, polyolefins and many other materials. The fibers may be relatively short, staple length fibers, typically less than three inches, or longer and substantially more continuous fibers such as are produced by spunbonding and meltblowing processes.

In some embodiments, a laminate material may be chosen for waste pouch 202, such as a laminate of spunbonded and meltblown or spunbonded, meltblown, spunbonded to impart both strength and barrier properties to waste pouch 202. A spunbonded-meltblown-spunbonded material is made from three separate layers that are laminated to one another. The method of making these layers is known and described in U.S. Pat. No. 4,041,203 to Brock, et al., which is incorporated herein in its entirety by reference. The material of Brock, et al. is a three layer laminate of spunbonded-meltblown-spunbonded layers that is also commonly referred to by the acronym "SMS." The two outer layers of SMS are a spunbonded material made from extruded polyolefin fibers, or filaments, laid down in a random pattern and then bonded to one another. The inner layer is a meltblown layer also made from extruded polyolefin fibers generally of a smaller diameter than the fibers in the spunbonded layers. As a result, the meltblown layer provides increased barrier properties due to its fine fiber structure, which, e.g., permits gases to pass through the fabric while preventing passage of liquids. Conversely, the two outer spunbonded layers provide a greater portion of the strength factor in the overall laminate. Thus, as in the depicted embodiment, SMS materials may be particularly suitable for use at least as an outer layer or shell of waste pouch 202.

Referring now to FIGS. 6-10, a method of using device 100 and/or collection apparatus 200 will be described, as well as a waste collection system for collecting waste from a body of a patient. Generally, the waste collection system 300 comprises device 100 and collection apparatus 200 to collect waste that would otherwise move through stoma 10 formed in body 20 of patient P. More particularly, in waste collection system 300, connector 208 of collection apparatus 200 is configured to interface with device 100 positioned in stoma 10. Connector 208 connects collection apparatus 200 to device 100 to facilitate the collection of waste from body 20.

Figure 6:
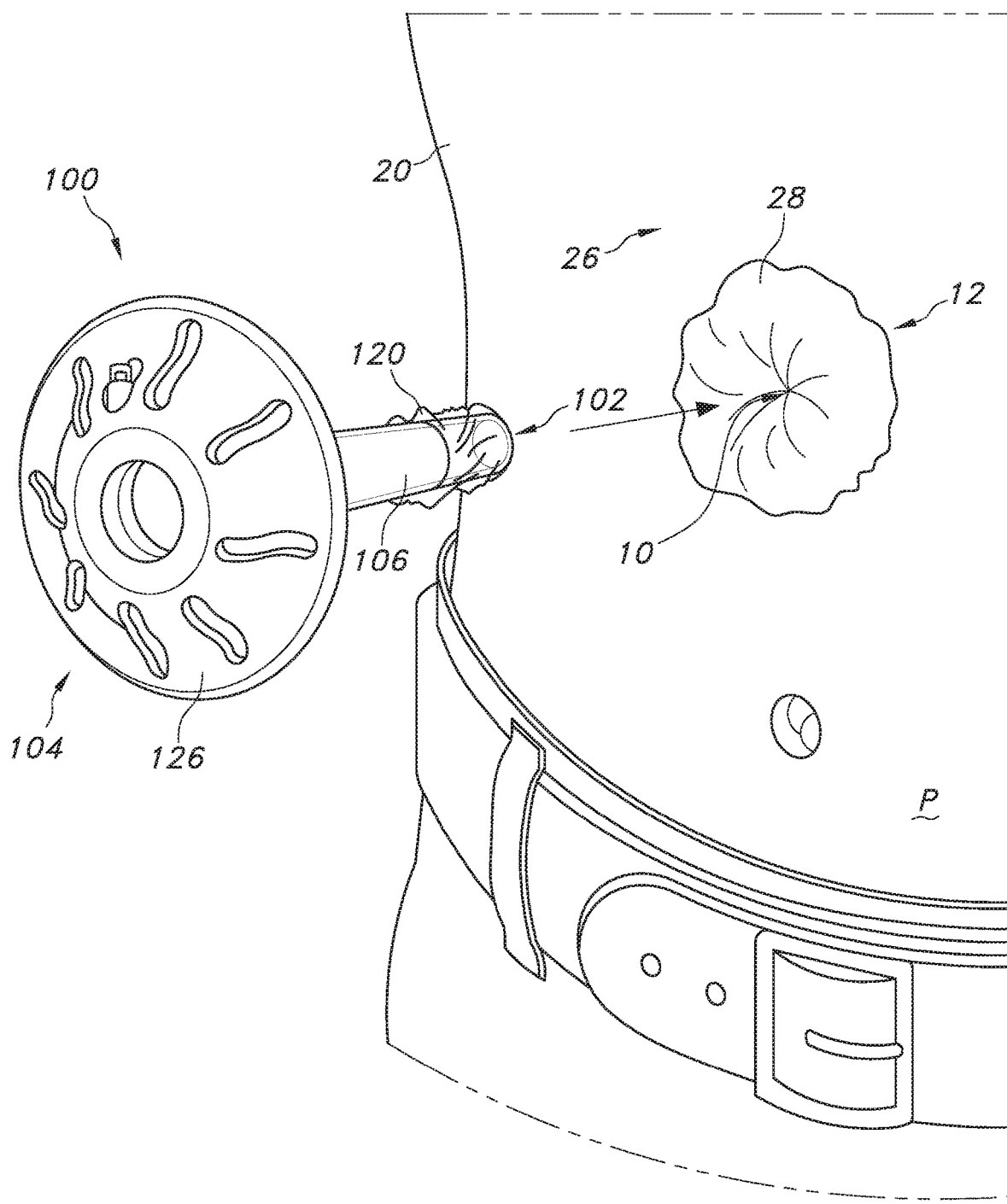
FIG. 6 provides a schematic illustration of the installation of the device of FIG. 1 within a stoma formed in a body of a patient, according to an exemplary embodiment of the present subject matter.

Referring particularly to FIG. 6, a schematic illustration is provided of the insertion of device 100 within stoma 10 formed in body 20 of patient P, according to an exemplary embodiment of the present subject matter. As shown, in a typical ostomy procedure, a portion of a lower gastrointestinal ("GI") organ 22 of the patient P is pulled through the patient's abdominal wall 24 (FIG. 7) such that this portion is external to the patient's body 20 and generally rests on an outer surface 26 (i.e., epidermis or skin) of body 20. As such, this portion will be referred to as an external portion 28 of lower GI organ 22 (FIG. 7), which together with stoma 10, defines a stoma site 12. As illustrated in FIG. 6, to insert device 100 into stoma 10, device 100 is oriented with distal end 102 of device 100 toward stoma site 12 and retention mechanism 120 is in its insertion position.

Figure 7:
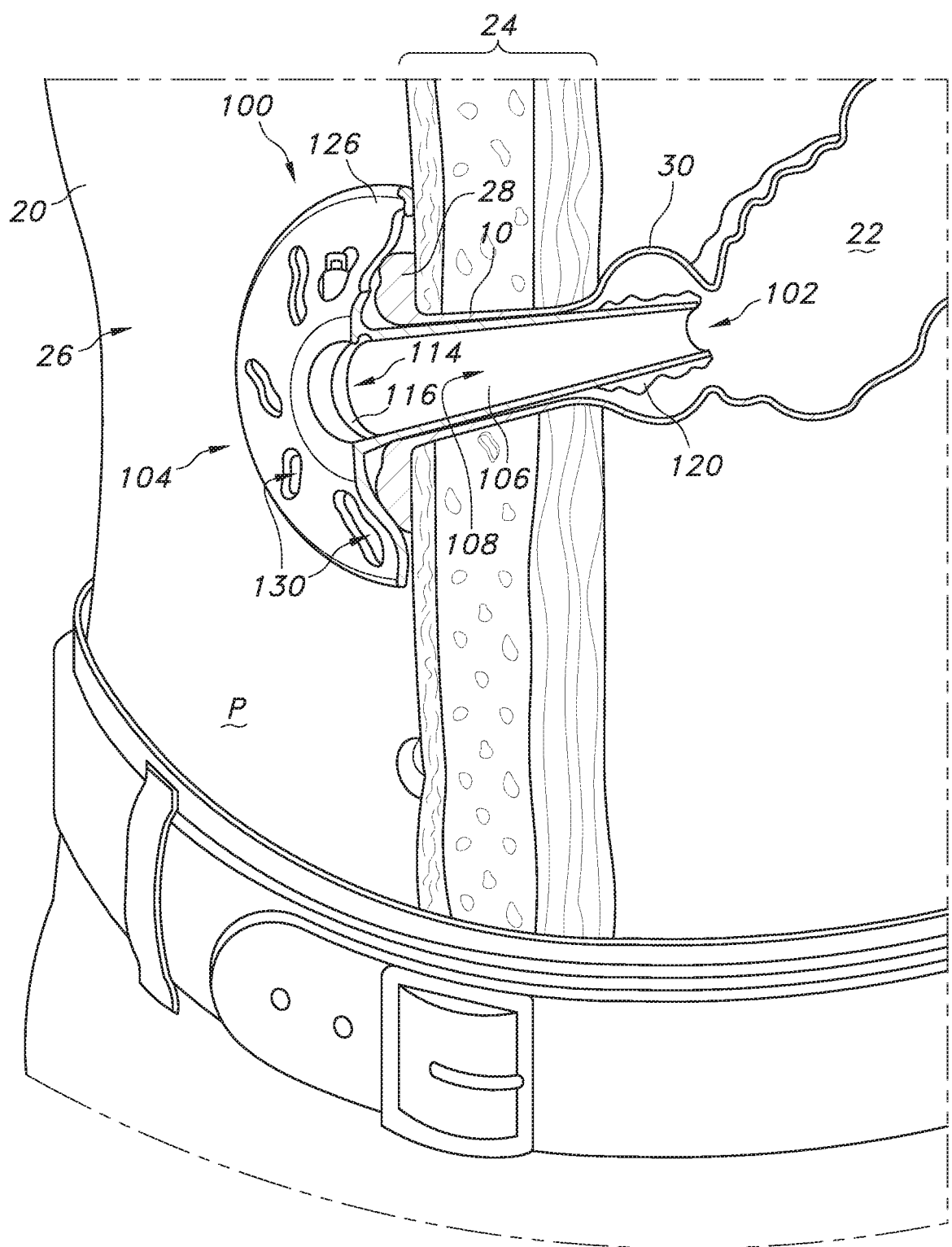
FIG. 7 provides an illustration of the device of FIG. 1 inserted within the stoma of FIG. 4, with the retention mechanism of the device in the insertion position.
Figure 8:
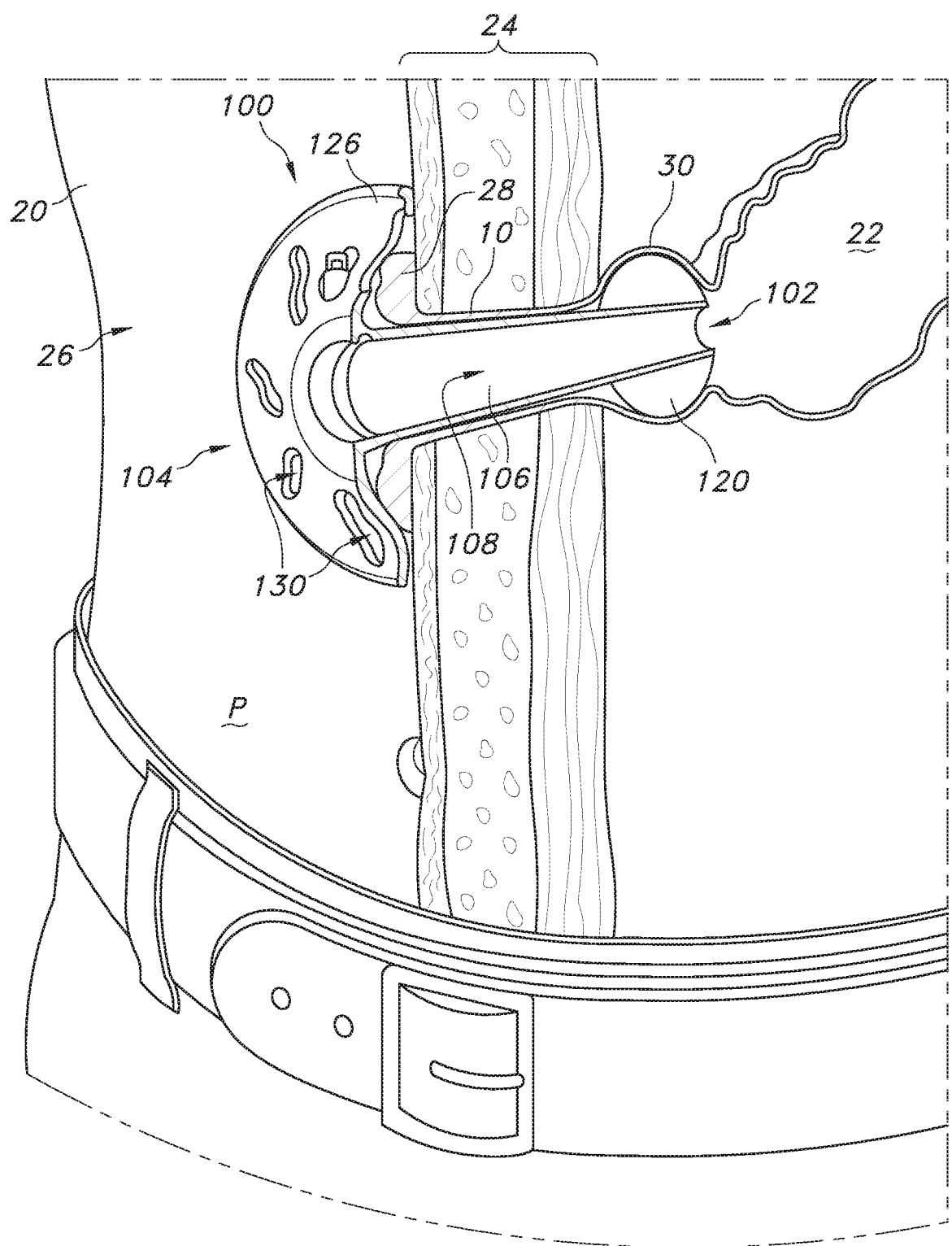
FIG. 8 provides an illustration of the device of FIG. 1 inserted within the stoma of FIG. 4, with the retention mechanism of the device in the retention position.

FIG. 7 provides an illustration of device 100 inserted within stoma 10, with retention mechanism 120 in the insertion position, and FIG. 8 provides an illustration of device 100 inserted within stoma 10, with retention mechanism 120 in the retention position. As illustrated, when device 100 is inserted within stoma 10, tube 106 is positioned within stoma 10 and barrier 126 is positioned adjacent external portion 28 of lower GI organ 22. Perimeter 132 of barrier 126 may rest against outer surface 26 of body 20. As previously discussed, barrier 126 may be flexible such that barrier 126 may be pulled back to access external portion 28 and/or external surface 26 beneath barrier 126, e.g., to clean external portion 28, external surface 26, and/or an underside of barrier 126. Further, vents 130 may be defined in barrier 126 to permit air to flow to external portion 28 and/or external surface 26 which, e.g., helps prevent an accumulation of moisture on body 20 that could lead to infection, irritation, or other adverse conditions.

Referring particularly to FIG. 8, in the depicted embodiment, retention mechanism 120 is an inflatable balloon or cuff that is inflated to retain device 100 within stoma 10. More specifically, a fluid (such as, e.g., air or a saline solution) may be introduced to balloon 120 through inflation valve 122 and inflation line 124 to inflate balloon 120. When inflated, i.e., when in the retention position, balloon 120 contacts walls 30 of lower GI organ 22 and/or stoma 10 to create an effective seal and thereby reduce leakage around the balloon at walls 30. Additionally, inflated balloon 120 (i.e., retention mechanism 120 in the retention position) abuts abdominal wall 24 of patient P to hold device 100 in place within stoma 10 and the natural pathway of organ 22 while sealing the natural pathway such that waste material moves only out of device 100 and, thus, the waste does not contact external portion 28 of lower GI organ 22.

Figure 9:
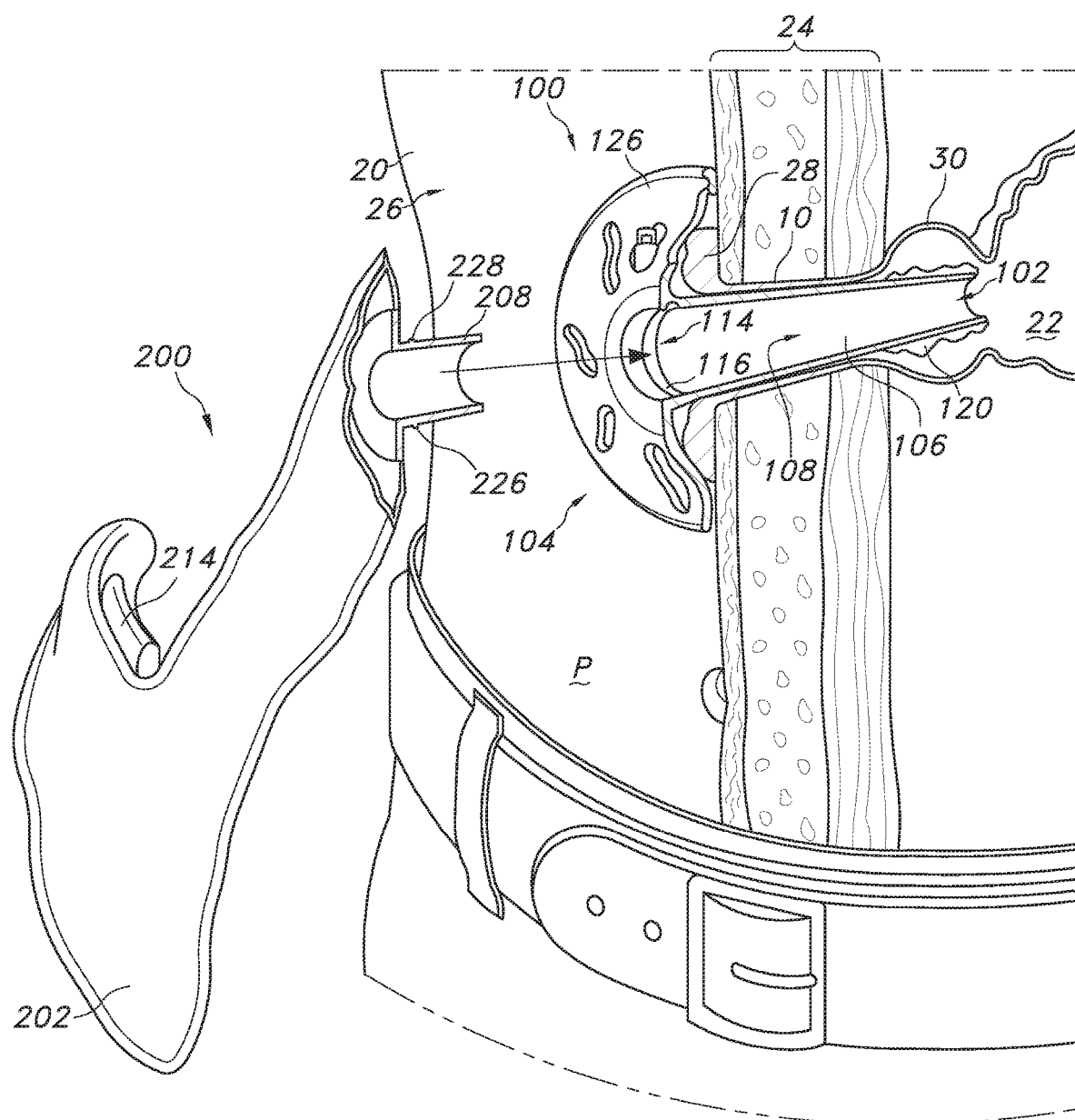
FIG. 9 provides a schematic illustration the insertion of the collection apparatus of FIG. 3 into the device of FIG. 1 to connect the collection apparatus and the device, according to an exemplary embodiment of the present subject matter.

Referring now to FIG. 9, a schematic illustration is provided of the insertion of collection apparatus 200 into device 100 to connect apparatus 200 and device 100, according to an exemplary embodiment of the present subject matter. As illustrated, to insert collection apparatus 200 into device 100, connector 208 of apparatus 200 is oriented toward proximal end 104 of device 100. As further illustrated, device 100 has been inserted into stoma 10 formed in body 20 of patient P, as described above.

Figure 10:
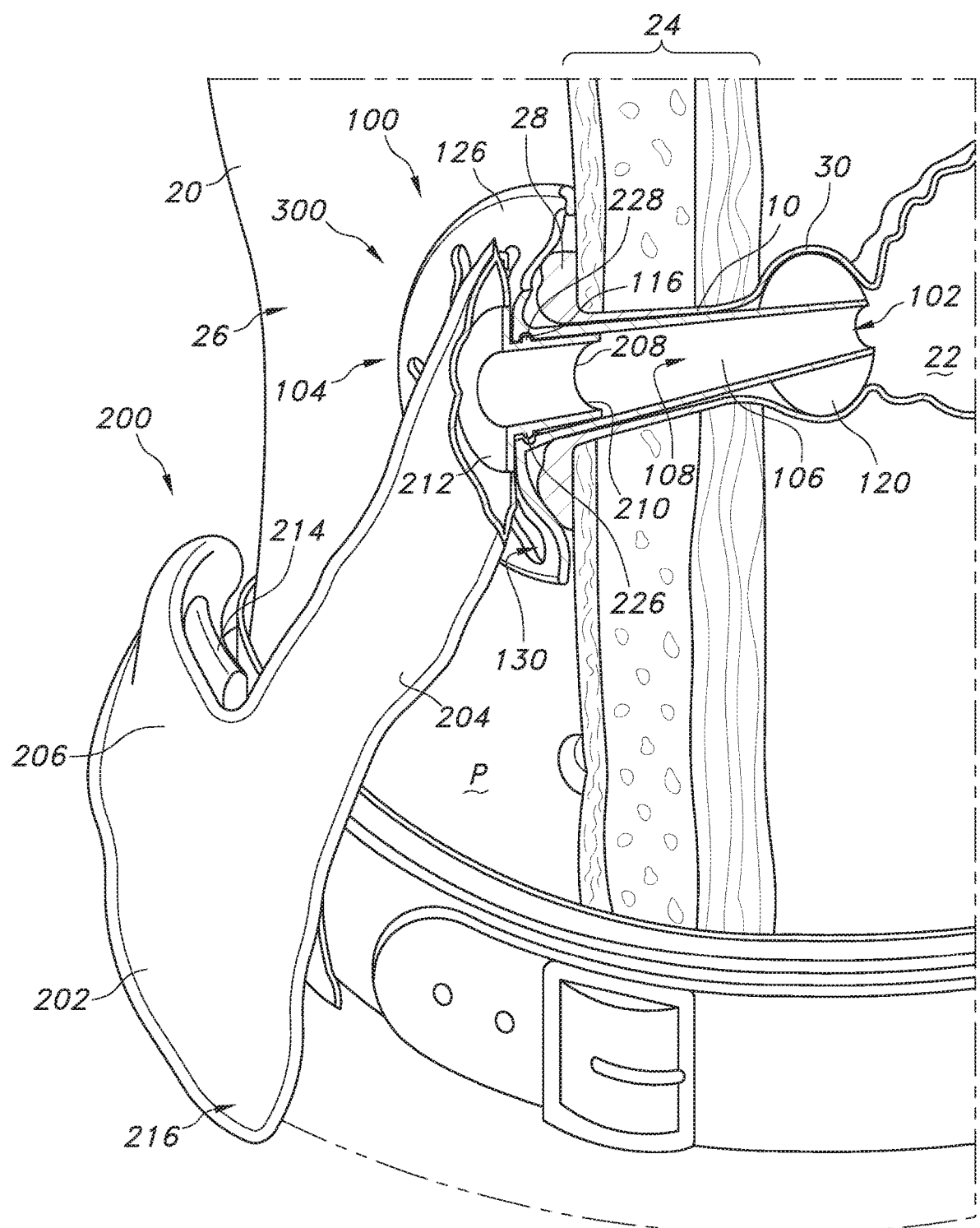
FIG. 10 provides a cross-section view of a waste collection system assembled for the collection of waste from a gastrointestinal organ of a patient, according to an exemplary embodiment of the present subject matter.

FIG. 10 provides a cross-section view of waste collection system 300 assembled for the collection of waste from lower GI organ 22 of patient P that would otherwise move through stoma 10, according to an exemplary embodiment of the present subject matter. As shown, waste collection system 300 comprises device 100 and collection apparatus 200, which are described in more detail above. Collection apparatus 200 is connected to device 100 via connection portions 114, 226 of device 100 and apparatus 200, respectively. When connected, a portion of outer surface 216 of waste pouch 202 adjacent flange portion 212 of connector 208 is positioned adjacent proximal surface 128 of barrier 126.

As further illustrated in the exemplary embodiment, tubular portion 210 of connector 208 has an outer diameter 234 sized to fit within an inner diameter 111 of tube 106 at proximal end 104 of device 100. Protrusion 228 of connection portion 226 of connector 208 fits within groove 116 of connection portion 114 of tube 106 to sealingly connect device 100 and collection apparatus 200. Generally, protrusion 228 may snap into groove 114 such that device 100 and apparatus 200 connect via a snap fit. As further described herein, other means of connecting device 100 and apparatus 200 and other fits between device 100 and apparatus 200, such as, e.g., an interference fit or the like, also may be used.

Moreover, in appropriate embodiments, device 100 and collection apparatus 200 may be coupled such that waste collection system 300 effectively is one piece. As one example, waste pouch 202 may be sealingly connected, coupled, or attached to barrier 126 or tube 106 of device 100. As such, waste collection system 300 may be configured for single use, such that the component that is placed within stoma 10 (e.g., tube 106) is disposable with waste pouch 202. Other configurations of waste collection system 300 as occur to one of ordinary skill in the art may be used as well.

In the depicted embodiment of FIG. 10, neck portion 204 of waste pouch 202 is configured as a transition between device 100 and container portion 206. That is, waste emptied from organ 22 via tube 106 of device 100 passes through connector 208 of collection apparatus 200 and into neck portion 204 before the waste is collected in container portion 206. More particularly, neck portion 204 permits some flexibility as to where container portion 206 is supported and in selecting an appropriately-sized waste pouch 202 for patient P. For example, the length $L_N$ of neck portion 204 may be selected such that attachment mechanism 214 of apparatus 200 is positioned at the patient's waistline, such that attachment mechanism 214 may be attached to the patient's belt or a waist of the patient's pants. In other embodiments, the length $L_N$ of neck portion 204 may be selected such that container portion 206 is supported at the small of the patient's back. As such, the length $L_N$ may vary from patient to patient, e.g., taller patients may require a longer length $L_N$ than shorter patients or stoma 10 may be formed at different locations for different patients. Thus, neck portion 204 permits container portion 206 to be supported away from stoma site 12, and the configuration of neck portion 204 may be selected based on a variety of variables.

As will readily be understood from the figures and the above description, to assemble waste collection system 300 for collection of waste from body 20 of patient P, stoma 10 first must be formed in body 20. Stoma 10 may be pre-existing, i.e., patient P may have used other systems for collecting waste before using waste collection system 300, or stoma 10 may be newly formed for use with system 300. As previously described, stoma 10 and stoma site 12 are formed by pulling a portion of lower GI organ 22 through abdominal wall 24 to outer surface 26 of body 20, such that the pulled-through portion is external portion 28 of organ 22. Then, device 100, in its insertion position, is inserted into stoma 10. Retention mechanism 120 is then deployed, e.g., by inflating the balloon, to place device 100 in its retention position and thereby retain device 100 within stoma 10. When in the retention position, distal end 102 of device 100 is positioned at organ 22 to receive waste from the organ. Waste may then move from organ 22 through path 108 formed by tube 106 of device 100. However, valve 134 may arrest the movement of waste, e.g., until a collection apparatus 200 is connected to device 100.

To connect apparatus 200 to device 100, tubular portion 210 of connector 208 is inserted into tube 106 at proximal end 104 of device 100. Connection portion 226 of connector 208 interfaces or engages with connection portion 114 of tube 106 to connect collection apparatus 200 to device 100. Attachment portion 214 may be attached to a support for supporting collection apparatus 200. Valve 134 may then open to permit the movement of waste to collection apparatus 200. Waste moves through tubular portion 210 of connector 208, through neck portion 204 of waste pouch 202, and into container portion 206 of waste pouch 202. When container portion 206 is full, or when the movement of waste has stopped, connector 208 may be disconnected and waste pouch 202 emptied or discarded. As needed, barrier 126 of device 100 may be bent or rolled or otherwise flexed back from external surface 26 of body 20 to clean stoma site 12, external surface 26, and/or barrier 126.

Figure 11:
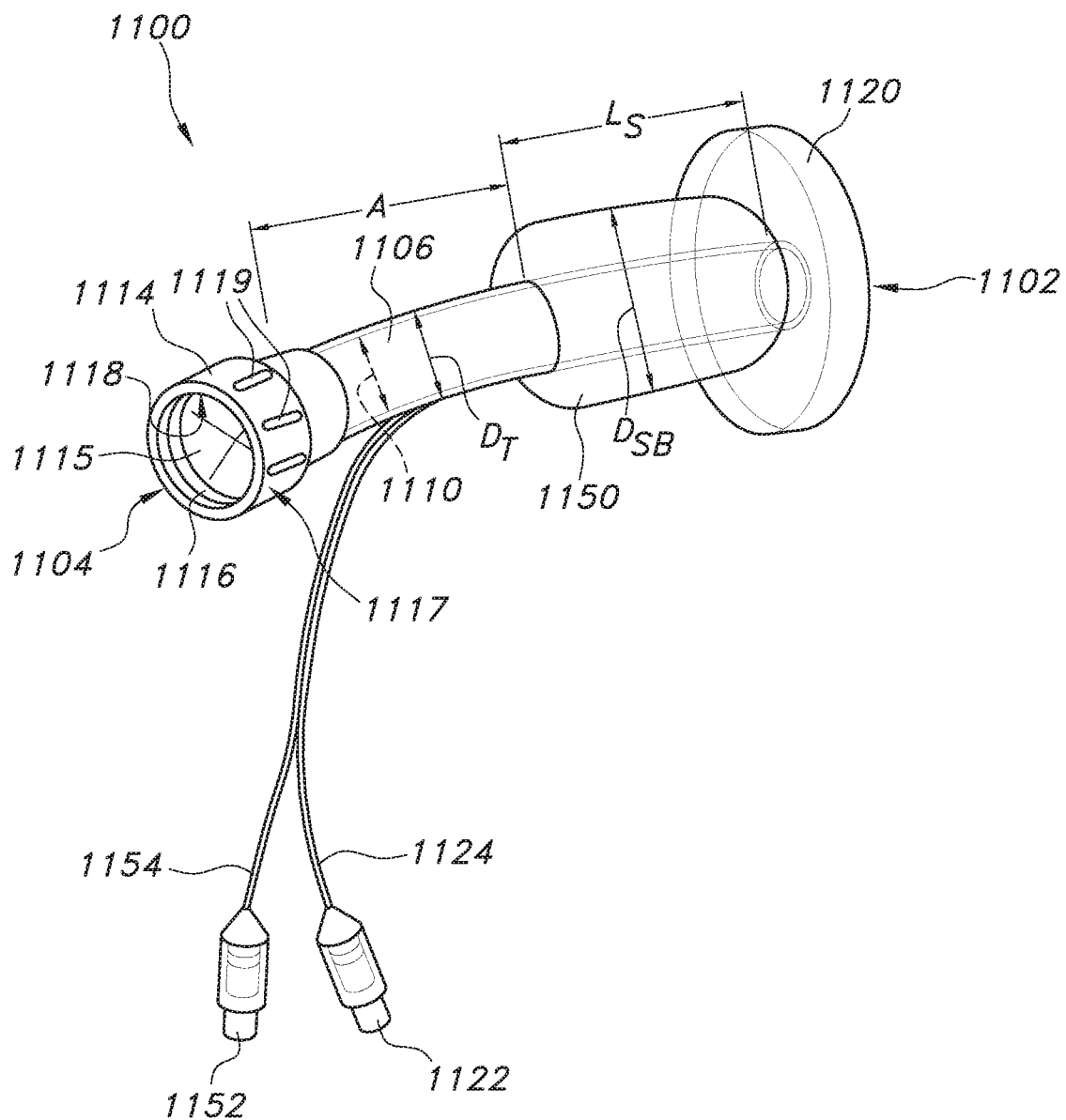
FIG. 11 provides a perspective view of a device for insertion into a stoma formed in a body of a patient, according to an exemplary embodiment of the present subject matter, in which a retention mechanism of the device is in a retention position and a sealing mechanism of the device is in a sealing position.

Turning to FIG. 11, a perspective view is provided of a device for insertion into a stoma formed in a body of a patient, according to another exemplary embodiment of the present subject matter. It will be appreciated that the device 1100 illustrated in FIG. 11 has some features that are similar to features of the device 100, but other features are different from or configured differently than features of the device 100. For example, unlike the device 100, the device 1100 includes a sealing mechanism that helps seal the stoma against undesirable travel of waste through the stoma rather than through a tube of the device 1100.

More particularly, the device 1100 defines an axial direction A and has a distal end 1102 and a proximal end 1104. Distal end 1102 is spaced apart from proximal end 1104 along the axial direction A. Device 1100 includes a tube 1106 extending along the axial direction A between distal end 1102 and proximal end 1104 of device 1100. Tube 1106 defines a path 1108 for movement of waste or effluent through the stoma as described in greater detail below. The tube 1106 has a length $L_T$ (FIG. 13) and an outer diameter $D_T$. In some embodiments, the tube 1106 may be tapered from one of ends 1102, 1104 toward the other end, may have a varying outer diameter $D_T$ along its length $L_T$, or may have a constant outer diameter $D_T$ from one end 1102, 1104 to the other. Further, tube 1106 may be rigid, flexible, or fully or partially collapsible; expandable, non-expandable, or partially expandable; soft or hard; or any appropriate combination of the foregoing. Moreover, tube 1106 may be relatively thin walled, e.g., to permit as large of an inner diameter and/or cross-sectional area as possible for the movement of waste through tube 1106. Tube 1106 may have other configurations as well.

In the depicted embodiment of FIG. 11, tube 1106 defines a connection portion 1114 at proximal end 1104. Connection portion 1114 includes a protrusion or rib 1116 defined along an inner surface 1118. Protrusion 1116 may be configured to be received in a groove of a waste collection pouch to connect the pouch to device 1100 and to seal the connection such that waste may move through tube 1106 to the waste pouch without leaking through the connection between the pouch and the device. It will be appreciated that, in other embodiments, connection portion 1114 may define a groove and the waste collection pouch may define a protrusion or rib that is received in the groove of the connection portion 1114 to connect the waste collection pouch to the device 1100. Connection portion 1114 also may have other configurations to mechanically or otherwise fasten or attach a waste pouch or other apparatus to device 1100. Further, as illustrated in FIG. 11, connection portion 1114 may include a seal or valve 1115 that helps prevent the passage of waste and gases through the connection portion 1114 when no waste pouch or other apparatus is connected to the device 1100. The seal or valve 1115 may be a passive flap valve as shown, which opens when a waste collection apparatus is connected to the device, but the seal or valve 1115 may have other configurations as well.

In the embodiment shown in FIG. 11, the connection portion 1114 defines a gripping surface 1117 around an outer diameter $D_C$ of the connection portion 1114. The gripping surface 1117 may include a plurality of ridges 1119, which can help a user such as patient P grip the connection portion 1114, e.g., as the user connects a waste collection apparatus to the connection portion 1114 of device 1100.

A retention mechanism 1120 is located on tube 1106 near distal end 1102. The retention mechanism 1120 has an insertion position and a retention position, shown in FIG. 11. In the depicted embodiment, retention mechanism 1120 is an inflatable balloon or cuff, such as a Microcuff® balloon described above. In such embodiments, the balloon is deflated when in the insertion position and inflated when in the retention position, similar to the retention mechanism 120 described above and illustrated in FIGS. 1, 2, and 6-10. In some embodiments, the retention balloon has an inflated diameter $D_{RB}$ that is from about 1.5 times to about 4 times the outer diameter $D_T$ of tube 1106. In particular embodiments, the inflated diameter $D_{RB}$ of the retention balloon is about twice the outer diameter $D_T$ of tube 1106 or from about two to about three times the outer diameter $D_T$ of tube 1106.

Figure 13:
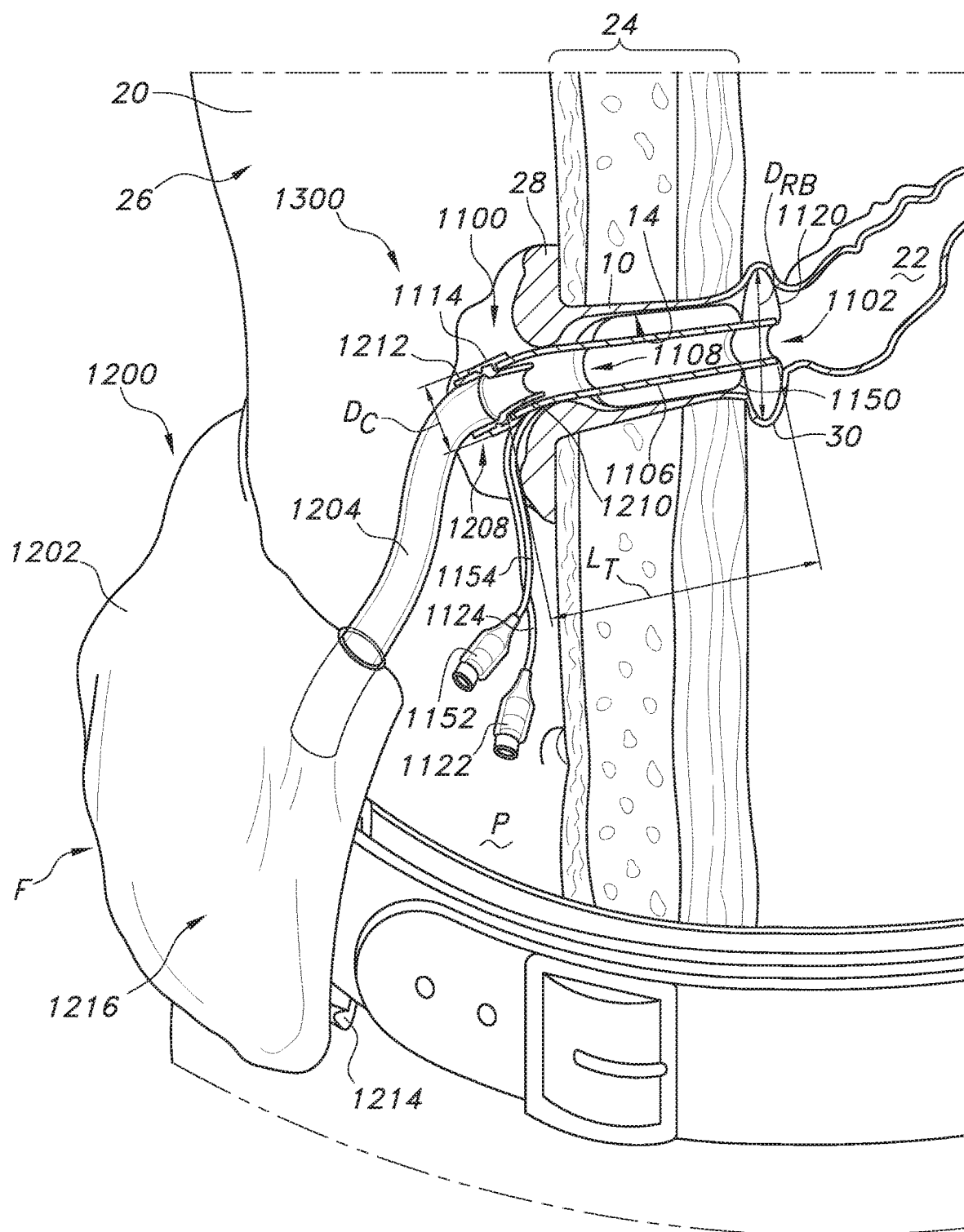
FIG. 13 provides a cross-section view of a waste collection system assembled for the collection of waste from a gastrointestinal organ of a patient, according to an exemplary embodiment of the present subject matter.

An inflation valve 1122 and an inflation line 1124 may be provided for inflating the balloon. As shown in FIGS. 11 and 13, the inflation line 1124 may extend from the retention balloon through the stoma 10 such that the inflation line 1124 extends through the stoma to outside the body of patient P and inflation valve 1122 is positioned outside of the patient P. Of course, other configurations of inflation valve 1122 and inflation line 1124 also may be used, e.g., inflation line 1124 may be incorporated into tube 1106 and inflation valve 1122 may be positioned at or near the connection portion 1114. It also will be readily understood by those of ordinary skill in the art that other retention mechanisms 1120 may be used as well, such as a flexible diaphragm or other mechanical means of retention and sealing at or near distal end 1102 of the tube 1106.

As further illustrated in FIG. 11, device 1100 also includes a sealing mechanism 1150. The sealing mechanism 1150 has an insertion position and a sealing position; the sealing mechanism is shown in the sealing position in FIG. 11. Further, the sealing mechanism 1150 extends axially along at least a portion $L_S$ of the length $L_T$ of the tube 1106 between the proximal end 1104 and the distal end 1102 of the tube 1106. As shown in FIG. 11, the sealing mechanism 1150 may extend over a greater length of tube 1106 than retention mechanism 1120. That is, the device 1100 may include a sealing mechanism 1150 along an extended axial length of tube 1106 such that the sealing portion $L_S$ of the length $L_T$ is a substantial portion of the length $L_T$ of the tube 1106, e.g., all or almost all of the length $L_T$. The tube 1106 may include a retention mechanism 1120 at the distal end 1102 of the tube 1106 such that the retention mechanism 1120 extends over little to none of the length $L_T$ of tube 1106.

Moreover, in the depicted embodiment, sealing mechanism 1150 is an inflatable balloon or cuff, which is deflated in the insertion position of the sealing mechanism 1150 and inflated in the sealing position of the sealing mechanism 1150, similar to the retention mechanism 120 described above and illustrated in FIGS. 1, 2, and 6-10. For instance, the inflatable balloon or cuff of the sealing mechanism 1150 may be a Microcuff® balloon described above. More particularly, the inflatable balloon or cuff forming the sealing mechanism 1150 may be fashioned of a thin film and designed to be a thin-wall, high-volume, low-pressure cuff. In some embodiments, the diameter of a thin-wall, high-volume, low-pressure cuff in a freely deployed state appreciably exceeds the diameter of the stoma into which the device 1100 is inserted. In other embodiments, the sealing balloon has an inflated diameter $D_{SB}$ that is from about 1.1 times to about twice the diameter $D_T$ of tube 1106, and in particular embodiments, the inflated diameter $D_{SB}$ is from about 1.2 times to about 1.5 times the outer diameter $D_T$ of tube 1106. When a high-volume/low-pressure cuff is used to seal the stoma, there is virtually no expansion of the cuff envelope under the potentially tissue-damaging pressures that are common with low-volume/high-pressure cuff balloons. Rather, the deployment of the cuff envelope to occlude the stoma results in an intentionally produced folding of the balloon envelope and permits filling pressures that are compatible with perfusion, providing certainty that the barometric pressure measured in the cuff balloon largely matches the pressure transmitted transmurally to the tissue forming the stoma. Further discussion of high-volume balloons may be found in, for example, U.S. Pat. Nos. 6,802,317 and 6,526,977, which teach oversized balloons with a wall thickness so low that the balloon walls lie in folds against a tracheal wall. The folds are so small that secretions or effluent cannot pass through them and, e.g., travel on along the path 1108 and out of the opening at proximal end 1104 of the tube 1106.

Similar to embodiments in which the retention mechanism 1120 is a retention balloon, in embodiments in which the sealing mechanism 1150 is a sealing balloon, an inflation valve 1152 and an inflation line 1154 may be provided for inflating the sealing balloon. As shown in FIGS. 11 and 13, the inflation line 1154 may extend from the sealing balloon through the stoma 10 such that the inflation line 1154 extends through the stoma 10 between the sealing balloon 1150 and the tube 1106 to inflation valve 1152 outside of the patient P. The inflation line 1124 of the retention balloon 1120 also may extend between the sealing mechanism 1150 and the tube 1106 to inflation valve 1122 outside of patient P. Further, other configurations of inflation valve 1152 and inflation line 1154 also may be used, e.g., inflation line 1154 may be incorporated into tube 1106 and inflation valve 1152 may be positioned at or near the connection portion 1114. In other embodiments, a single inflation line and inflation valve may be provided for inflating both the retention mechanism 1120 and the sealing mechanism 1150. In such embodiments, each of the retention balloon and sealing balloon may be inflated to the same pressure. Other sealing mechanisms 1150 than an inflatable sealing balloon may be used as well, such as a flexible diaphragm or other mechanical means of retention and sealing along a length $L_S$ of the tube 1106 within stoma 10.

Figure 12:
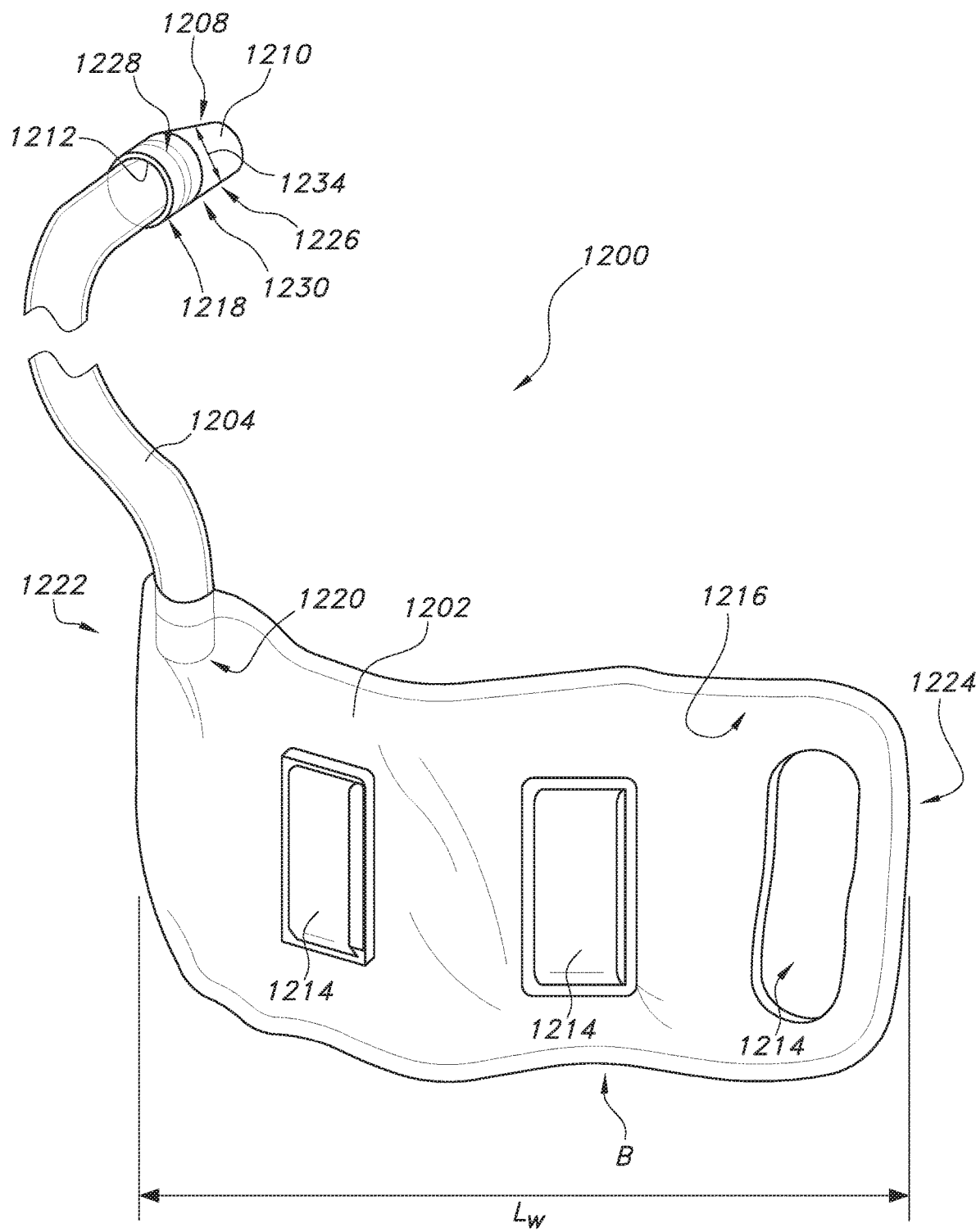
FIG. 12 provides a perspective view of a collection apparatus for collecting waste moving through a stoma formed in a body of a patient, according to an exemplary embodiment of the present subject matter.

As previously described, the connection portion 1114 defined at the proximal end 1104 of the device 1100 may receive a connector of a waste collection apparatus, which extends the path 1108 for movement of waste into the waste collection apparatus. An exemplary waste collection apparatus 200 is described above and illustrated in FIGS. 5, 9, and 10. Turning to FIG. 12, a perspective view is provided of a collection apparatus for collecting waste moving through a stoma formed in a body of a patient, according to another exemplary embodiment of the present subject matter. The exemplary collection apparatus 1200 described below may have some features that are similar to features of the collection apparatus 200, but other features may be different from or configured differently than features of the collection apparatus 200. For example, as depicted in FIG. 12, the collection apparatus 1200 includes a waste bag or a waste pouch 1202, a conduit 1204, and a connector 1208, having a tubular portion 1210 and a securing portion 1212. Like waste pouch 202, waste pouch 1202 collects waste rejected from the body through the stoma formed in the body.

Collection apparatus 1200 also may include one or more attachment mechanisms 1214 for attaching collection apparatus 1200 to a support. For example, using attachment mechanism(s) 1214, collection apparatus 1200 may be attached to a support or support structure—such as, e.g., the patient's clothing or a healthy portion of the patient's body away from the stoma—that can help support the weight of collection apparatus 1200, particularly when it is filled with waste. Attachment mechanism(s) 1214 may be coupled to an outer surface 1216 of waste pouch 1202, e.g., spaced along a length $L_W$ of waste pouch 1202 as depicted, using any appropriate fastener or fastening mechanism. Additionally, attachment mechanism(s) 1214 may be any appropriate mechanism for attaching collection apparatus 1200 to a support. For example, each attachment mechanism 1214 may be a stretchable, elastic loop; a hook-and-loop type fastener; an adhesive; a molded plastic clip; a loop defined in waste pouch 1202; or any other appropriate mechanism for attaching collection system 1200 to a support. In some embodiments, such as the embodiment shown in FIG. 12 in which attachment mechanisms 1214 include plastic clips and a loop defined in waste pouch 1202, a variety of attachment mechanisms 1214 may be used, i.e., each attachment mechanism 1214 need not be of the same type.

As further illustrated in FIG. 12, the conduit 1204 extends from connector 1208 to waste pouch 1202. Waste pouch 1202 defines an opening for receipt of conduit 1204, and conduit 1204 may be received within waste pouch 1202 such that a fluid tight seal is formed between conduit 1204 and waste pouch 202. That is, waste pouch 1202 and conduit 1204 may be coupled such that fluid cannot leak at the attachment point between waste pouch 1202 and conduit 1204. In some embodiments, waste pouch 1202 and conduit 1204 may be mechanically coupled or thermally bonded to one another. In still other embodiments, an appropriate adhesive may be used to couple waste pouch 1202 and conduit 1204. In suitable embodiments, the conduit 1204 is removably received within the waste pouch 1202, e.g., such that the conduit 1204 may be reused after the patient disposes of a waste pouch 1202. Any other appropriate means also may be used to attach conduit 1204 to waste pouch 1202 such that a fluid tight seal is formed between the two components.

Further, the connector 1208 of the collection apparatus 1200 is attached to conduit 1204 for coupling the collection apparatus 1200 to the device 1100. More particularly, conduit 1204 has a first end 1218 and a second end 1220 separated by a length. Connector 1208 is secured to the first end 1218 of conduit 1204 at the securing portion 1212 of connector 1208. The connector 1208 may be mechanically coupled, thermally bonded, or otherwise secured to the conduit 1204. The second end 1220 of conduit 1204 is received within waste pouch 1202 on a right side 1222 of waste pouch 1202 when viewing the collection apparatus 1200 from a front side F; a back side B of the collection apparatus 1200 is shown in FIG. 12. Alternatively, conduit 1204 may be received within waste pouch 1202 such that the conduit 1204 is centered with respect to waste pouch 1202, e.g., a centerline of conduit 1204 is aligned with a centerline of waste pouch 1202, or conduit 1204 may be received within waste pouch 1202 on a left side 1224 of waste pouch 1202.

Referring particularly to connector 1208, the tubular portion 1210 defines a connection portion 1226. Connection portion 1226 includes a groove 1228 extending about an outer surface 1230 of connection portion 1226. As generally described above, a protrusion 1116 of the device 1100 may be configured to be received within the groove 1228 of connector 1208 to connect waste pouch 1202 of collection apparatus 1200 to device 1100, as well as to seal the connection between waste pouch 1202 and device 1100. Thereby, when waste pouch 1202 is sealingly connected to device 1100, waste may move through tube 1106 to waste pouch 1202 without leaking through the connection between connector 1208 of collection apparatus 1200 and tube 1106 of device 1100. Connection portion 1114 of device 1100 and connection portion 1226 of collection apparatus 1200 generally may be described as a connection assembly, where protrusion 1116 is a male portion of the mechanical connection assembly and groove 1228 is a female portion of the assembly. In alternative embodiments, connection portion 1114 may define the female portion of the connection assembly and connection portion 1226 may define the male portion of the assembly. Of course, as previously described, connection portion 1114 may have other configurations and, similarly, connection portion 1226 may have other configurations to mechanically or otherwise fasten or attach waste pouch 1202 to device 1100 or another device.

Collection apparatus 1200 may incorporate one or more features for controlling odors, wet spots, irritation, or other undesirable conditions that could occur when collection apparatus 1200 receives waste. For example, similar to waste pouch 202 depicted in FIG. 5, the waste pouch 1202 may include a layer of liquid impervious film to help prevent liquids from soaking through the pouch 1202, or waste pouch 1202 may include a coating or integrated material or formulation that is selectively permeable to one or more gases such that the pouch 1202 does not balloon or swell and/or does not emit odors. Of course, other coatings, films, or the like also may be used to prevent undesirable conditions of collection system 1200. Additionally, the waste pouch 1202 may be made from a nonwoven material, e.g., a SMS material, which may improve patient comfort as well as impart strength and barrier properties to the waste pouch 1202. Nonwoven and SMS materials are described in greater detail above with respect to waste pouch 202, and such discussion is also applicable to nonwoven materials, such as SMS, that may be used to produce waste pouch 1202.

Referring now to FIG. 13, a waste collection system for collecting waste from a body of a patient is illustrated. Generally, the waste collection system 1300 comprises device 1100 and collection apparatus 1200 to collect waste that would otherwise move through stoma 10 formed in body 20 of patient P. A typical ostomy procedure for forming stoma 10 is described above with respect to FIGS. 6 and 7. FIG. 13 provides a schematic illustration of waste collection system 1300 positioned to collect waste from lower GI organ 22 of the patient P through stoma 10, which may be formed as previously described. As shown in FIG. 13, the device 1100 is inserted into stoma 10 such that distal end 1102 of device 1100 is positioned at or within lower GI organ 22. It will be appreciated that, when device 1100 is inserted into stoma 10, retention mechanism 1120 is in its insertion position, in which the retention mechanism 1120 generally conforms to the outer diameter $D_T$ of the tube 1106 or in a position in which the retention mechanism 1120 is smaller than the outer diameter $D_T$ of tube 1106.

As further illustrated in FIG. 13, when device 1100 is inserted within stoma 10, tube 1106 is positioned within stoma 10 and connection portion 1114 is positioned adjacent external portion 28 of lower GI organ 22. In the depicted embodiment, retention mechanism 1120 is an inflatable balloon or cuff that is inflated to retain device 1100 within stoma 10. More specifically, a fluid (such as, e.g., air or a saline solution) may be introduced to retention balloon 1120 through inflation valve 1122 and inflation line 1124 to inflate retention balloon 1120. When inflated, i.e., when in the retention position and inflated to its inflated diameter $D_{RB}$, the retention balloon 1120 contacts walls 30 of lower GI organ 22 and/or stoma 10 to create an effective seal and thereby reduce leakage around the balloon at walls 30 and/or stoma 10. In its retention position, the retention mechanism 1120 expands to a diameter greater than a diameter $D_{ST}$ of the stoma 10. For instance, in the embodiment of FIG. 13, the inflated diameter $D_{RB}$ of retention balloon 1120 is greater than the stoma diameter $D_{ST}$; as previously stated, in some embodiments, the inflated diameter $D_{RB}$ may be about two to three times greater than the stoma diameter $D_{ST}$. Additionally, inflated retention balloon 1120 (i.e., retention mechanism 1120 in the retention position) abuts abdominal wall 24 of patient P to hold device 1100 in place within stoma 10 and the natural pathway of organ 22 while sealing the natural pathway such that waste material moves only out of device 1100 and, thus, the waste does not contact external portion 28 of lower GI organ 22.

Moreover, the sealing mechanism 1150 may be deployed to help seal the stoma 10 such that waste moves only outer of device 1100 and into waste pouch 1202. In the exemplary embodiment shown in FIG. 13, the sealing mechanism 1150 is an inflatable balloon or cuff as described above. The sealing balloon 1150 inflates to retain device 1100 within stoma 10. More particularly, the exemplary sealing balloon 1150 expands as a fluid (such as, e.g., air or a saline solution) is introduced to sealing balloon 1150 through inflation valve 1152 and inflation line 1154. When inflated, i.e., when in the sealing position and inflated to its inflated diameter $D_{SB}$, the sealing balloon 1150 expands against a surface 14 of the stoma 10 such that the sealing balloon 1150 contacts stoma 10 to create an effective seal and thereby reduce leakage around the sealing balloon. As described above, the inflated diameter $D_{SB}$ of sealing balloon 1150 is greater than the diameter $D_T$ of tube 1106, and in some embodiments, the inflated diameter $D_{SB}$ may be about 1.2 to about 1.5 times greater than the tube diameter $D_T$. Further, as previously stated, the sealing balloon 1150 may be a thin-wall, high-volume, low-pressure cuff, which may effectively seal stoma 10 without imparting too great a pressure to the tissue forming stoma 10. Additionally, as shown in FIG. 13, the sealing mechanism 1150 extends along a greater length of tube 1106 than retention mechanism 1120, i.e., the sealing mechanism 1150 has an extended axial length compared to retention mechanism 1120.

As further illustrated in FIG. 13, collection apparatus 1200 is connected to device 1100 via connection portions 1114, 1226 of device 1100 and apparatus 1200, respectively. More particularly, the protrusion 1116 of connection portion 1114 of device 1100 is received within the groove 1228 of connection portion 1226 of apparatus 1200, thereby coupling or the device 1100 and apparatus 1200 and providing a path for the movement of waste from lower GI organ 22 to waste pouch 1202.

As further illustrated in the exemplary embodiment, tubular portion 1210 of connector 1208 has an outer diameter 1234 sized to fit within an inner diameter 1110 of tube 1106 at proximal end 1104 of device 1100. The connection mechanism of device 1100 and collection apparatus 1200 sealingly connects the device 1100 and collection apparatus 1200. Generally, protrusion 1116 may snap into groove 1228 such that device 1100 and apparatus 1200 connect via a snap fit. As further described herein, other means of connecting device 1100 and apparatus 1200 and other fits between device 1100 and apparatus 1200, such as, e.g., an interference fit or the like, also may be used.

Moreover, in appropriate embodiments, device 1100 and collection apparatus 1200 may be coupled such that waste collection system 1300 effectively is one piece. As one example, connector 1208 of collection apparatus 1200 may be sealingly connected, coupled, or attached to connection portion 1114 or tube 1106 of device 1100. As such, waste collection system 1300 may be configured for single use, such that the component that is placed within stoma 10 (e.g., tube 1106) is disposable with waste pouch 1202. Of course, even when waste collection system 1300 is not configured as a single piece, the device 1100 and collection apparatus 1200 of system 1300 may be configured for single, one-time use. Other configurations of waste collection system 1300 as occur to one of ordinary skill in the art may be used as well.

In the depicted embodiment of FIG. 13, conduit 1204 is configured as a transition between device 1100 and waste pouch 1202. That is, waste emptied from organ 22 via tube 1106 of device 1100 passes through connector 1208 of collection apparatus 1200 and into conduit 1204 before the waste is collected in waste pouch 1202. More particularly, conduit 1204 permits some flexibility as to where waste pouch 1202 is supported and in selecting an appropriately-sized waste pouch 1202 for patient P. For example, the length of conduit 1204 may be selected such that attachment mechanism(s) 1214 of apparatus 1200 are positioned at the patient's waistline, such that attachment mechanism(s) 1214 may be attached to a belt or a waist of the patient's pants. In other embodiments, the length of conduit 1204 may be selected such that waste pouch 1202 is supported at the small of the patient's back. As such, the conduit length may vary from patient to patient, e.g., taller patients may require a longer length conduit 1204 than shorter patients or stoma 10 may be formed at different locations for different patients. In still other embodiments, the length of conduit 1204 inserted into waste pouch 1202 may vary to adjust to the distance between stoma site 12 and waste pouch 1202, e.g., conduit 1204 may be inserted further into waste pouch 1202 for some patients than others or depending on where the patient P chooses to support the waste pouch 1202 at a particular time (e.g., patient P could wear the waste pouch 1202 on the patient's belt for a period of time and then wear the waste pouch 1202 at the small of the pateint's back for another period of time). In any event, conduit 1204 permits waste pouch 1202 to be supported away from stoma site 12, and the configuration of conduit 1204 may be selected based on a variety of variables.

As will readily be understood from the foregoing description and FIG. 13, to assemble waste collection system 1300 for collection of waste from body 20 of patient P, stoma 10 first must be formed in body 20. Stoma 10 may be pre-existing, i.e., patient P may have used other systems for collecting waste before using waste collection system 1300, or stoma 10 may be newly formed for use with system 1300. As previously described, stoma 10 and stoma site 12 are formed by pulling a portion of lower GI organ 22 through abdominal wall 24 to outer surface 26 of body 20, such that the pulled-through portion is external portion 28 of organ 22. Then, device 1100, in its insertion position, is inserted into stoma 10. Retention mechanism 1120 is then deployed, e.g., by inflating a retention balloon, to place retention mechanism 1120 in its retention position and thereby retain device 1100 within stoma 10. When in the retention position, distal end 1102 of device 1100 is positioned at organ 22 to receive waste from the organ. Sealing mechanism 1150 also is deployed, e.g., by inflating a sealing balloon, to place sealing mechanism 1150 in its sealing position and thereby seal stoma 10 from the passage of waste through the stoma rather than tube 1106. Waste may then move from organ 22 through path 1108 formed by tube 1106 of device 1100. However, seal or valve 115, or another valve within tube 1106 similar to valve 134 described with respect to device 100, may arrest the movement of waste, e.g., until a collection apparatus 1200 is connected to device 1100.

To connect apparatus 1200 to device 1100, tubular portion 1210 of connector 1208 is inserted into tube 1106 at proximal end 1104 of device 1100. Connection portion 1226 of connector 1208 interfaces or engages with connection portion 1114 of tube 1106 to connect collection apparatus 1200 to device 1100. Attachment mechanism(s) 1214 may be attached to a support for supporting collection apparatus 1200; the attachment mechanism(s) 1214 may be attached to the support before the connector 1208 is inserted into tube 1106. Waste may then move through tube 1106, connector 1208, conduit 1204, and into waste pouch 1202. When waste pouch 1202 is full, or when the movement of waste has stopped, connector 1208 may be disconnected and waste pouch 1202 emptied or discarded.

Figure 14:
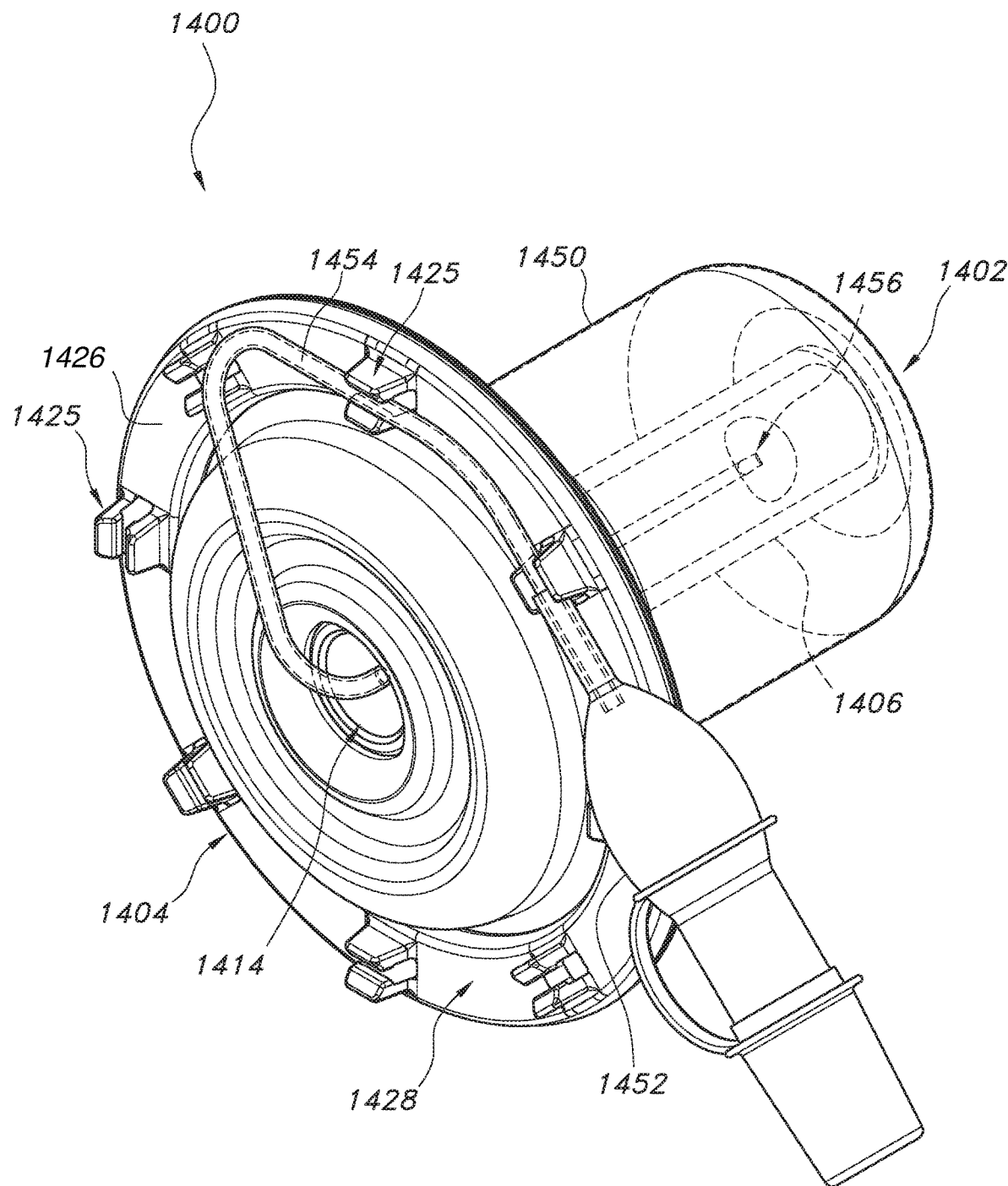
FIG. 14 provides a perspective view of a device for insertion into a stoma formed in a body of a patient, according to an exemplary embodiment of the present subject matter, in which a sealing mechanism of the device is in a sealing position.
Figure 15:
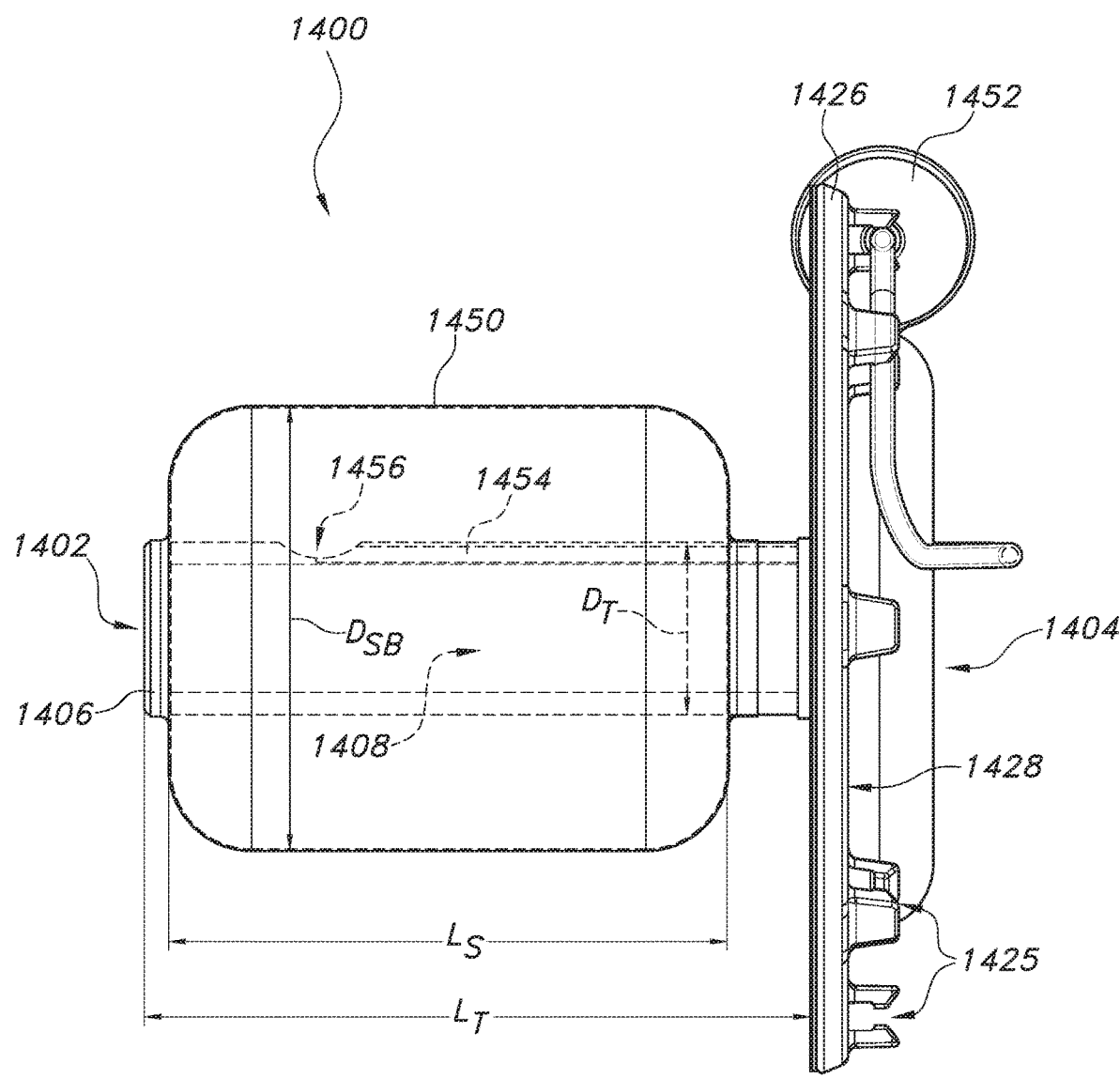
FIG. 15 provides a side view of the device of FIG. 14.

Turning now to FIGS. 14 and 15, a device for insertion into a stoma formed in a body of a patient is illustrated, according to another exemplary embodiment of the present subject matter. Similar to devices 100 and 1100 described above, the device 1400 defines an axial direction A and has a distal end 1402 and a proximal end 1404. Distal end 1402 is spaced apart from proximal end 1404 along the axial direction A.

Device 1400 includes a tube 1406 extending along the axial direction A between the distal and proximal ends 1402, 1404. The tube 1406 defines a path 1408 for movement of waste or effluent through a stoma 10 (FIG. 16) defined in the body 20 of a patient P. The tube 1406 has a length $L_T$ and an outer diameter $D_T$. As described with respect to devices 100 and 1100, in some embodiments, tube 1406 is tapered from one of ends 1402, 1404 toward the other end, or tube 1406 may have a varying outer diameter $D_T$ along its length $L_T$. In other embodiments, the tube 1406 has a constant outer diameter $D_T$ from the proximal end 1404 to the distal end 1402. The tube 1406 may be rigid, flexible, or fully or partially collapsible; expandable, non-expandable, or partially expandable; soft or hard; or any appropriate combination of the foregoing. Moreover, tube 1406 may be relatively thin walled, e.g., to permit as large of an inner diameter and/or cross-sectional area as possible for the movement of waste through tube 1406. Tube 1406 may have other configurations as well.

Tube 1406 defines a connection portion 1414 at its proximal end 1404. Connection portion 1414 includes one or more features for connecting a waste collection apparatus to the device 1400. For example, the connection portion 1414 may define a groove or a protrusion or rib defined along an inner surface 1418 of the connection portion 1414, similar to the connection portions 114, 1114 described with respect to other embodiments of a device for positioning in a stoma. The one or more features of the connection portion 1414 may help connect a waste pouch of a waste collection apparatus to device 1400 and seal the connection such that waste may move through tube 1406 to the waste pouch without leaking through the connection between the pouch and the device. Connection portion 1414 may have any suitable configuration to mechanically or otherwise fasten or attach a waste pouch or other apparatus to device 1400. Further, as described with respect to device 1100, connection portion 1414 of device 1400 may include a seal or valve similar to seal or valve 1115 that helps prevent the passage of waste and gases through the connection portion 1414 when no waste pouch or other apparatus is connected to the device 1400. The seal or valve may be configured to open when a waste collection apparatus is connected to the device 1400 and to remain closed when no apparatus is connected to the device. Alternatively, a valve such as valve 134 as described above with respect to device 100 may be positioned within the tube 1406 to control a flow of waste through the tube.

Continuing with FIGS. 14 and 15, the proximal end 1404 of the device 1400 may include a flange or barrier 1426 that defines a proximal surface 1428. As depicted, barrier 1426 is generally circular in shape and defines a circumferential direction C. A series of clips or retention structures 1425 may be defined along the proximal surface 1428. The retention structures 1425 may be equally spaced about the barrier 1426 as shown in FIGS. 14 and 15, or in other embodiments, only one retention structure 1425 or a small number of retention structures 1425 are positioned on one area of the proximal surface 1428. In some embodiments, the retention structures 1425 are configured to retain an inflation line for inflating a balloon positioned within the body of the patient as further described below. In other embodiments, the retention structures 1425 are configured to hold other features of the device 1400 or a waste collection apparatus attached to the device 1400, e.g., such that the features do not protrude from device 1400 or interfere with the use of device 1400.

Barrier 1426 may be flexible like barrier 126 described above, e.g., to provide access to an area beneath the barrier by bending or rolling back the barrier such that an area otherwise covered by the barrier may be accessed. Thus, in some embodiments, barrier 1426 is made from an elastomeric material that allows barrier 1426 to flex. However, barrier 1426 may be made from other suitable materials as well, and in appropriate embodiments, barrier 1426 may be inflexible. For example, the barrier 1426 may be relatively rigid, e.g., to provide support for a waste collection apparatus connected to the device 1400.

As further illustrated in FIGS. 14 and 15, device 1400 also includes a sealing mechanism 1450 similar to the sealing mechanism 1150 described above. The sealing mechanism 1450 has an insertion position and a sealing position; the sealing mechanism is shown in the sealing position in FIGS. 14 and 15. Further, as most clearly illustrated in FIG. 15, the sealing mechanism 1450 extends axially along at least a portion $L_S$ of the length $L_T$ of the tube 1406 between the proximal end 1404 and the distal end 1402 of the tube 1406. In the depicted embodiment, the sealing mechanism 1450 extends over almost the entire length $L_T$ of tube 1406 such that the device 1400 includes a sealing mechanism 1450 along an extended axial length of tube 1406.

Moreover, in the depicted embodiment, sealing mechanism 1450 is an inflatable balloon or cuff, which is deflated in the insertion position of the sealing mechanism 1450 and inflated in the sealing position of the sealing mechanism 1450. In an exemplary embodiment, the inflatable balloon or cuff forming sealing mechanism 1450 is a Microcuff® balloon as described with respect to sealing mechanism 1150. More particularly, as previously described, the inflatable balloon or cuff forming the sealing mechanism 1450 may be fashioned of a thin film and designed to be a thin-wall, high-volume, low-pressure cuff. In some embodiments, the diameter of a thin-wall, high-volume, low-pressure cuff in a freely deployed state appreciably exceeds the diameter of the stoma into which the device 1400 is inserted. In other embodiments, the sealing balloon has an inflated diameter $D_{SB}$ that is from about 1.1 times to about twice the diameter $D_T$ of tube 1406, and in particular embodiments, the inflated diameter $D_{SB}$ is from about 1.2 times to about 1.5 times the outer diameter $D_T$ of tube 1406. Thin-wall, high-volume, low-pressure balloons or cuffs are described in more detail above.

In embodiments in which the sealing mechanism 1450 is a sealing balloon, an inflation valve 1452 and an inflation line 1454 may be provided for inflating the sealing balloon. As shown in FIGS. 14 and 15, the inflation line 1454 may extend from the sealing balloon through the stoma 10 to inflation valve 1452 positioned at the barrier 1426 of device 1400. More specifically, a port 1456 may be defined in sealing balloon 1450, and inflation line 1454 extends from inflation valve 1452 to port 1456 to deliver fluid to sealing balloon 1450 to inflate the balloon. A length of inflation line 1454 outside of stoma 10 may be received in one or more retention structures 1425, e.g., to keep the inflation line 1454 relatively flat against barrier 1426. For instance, retaining any external inflation line 1454 within retention structures 1425 can prevent the inflation line 1454 from being caught, e.g., on the patient's clothing, and tugged on, which could uncomfortably pull the device against stoma 10 or perhaps pull the device 1400 out of the stoma 10. Of course, other configurations of inflation valve 1452 and inflation line 1454 also may be used, e.g., inflation line 1454 may be incorporated into tube 1406. It also will be readily understood by those of ordinary skill in the art that other sealing mechanisms 1450 than an inflatable sealing balloon may be used as well, such as a flexible diaphragm or other mechanical means of retention and sealing along a length $L_S$ of the tube 1406 within stoma 10.

Figure 16:
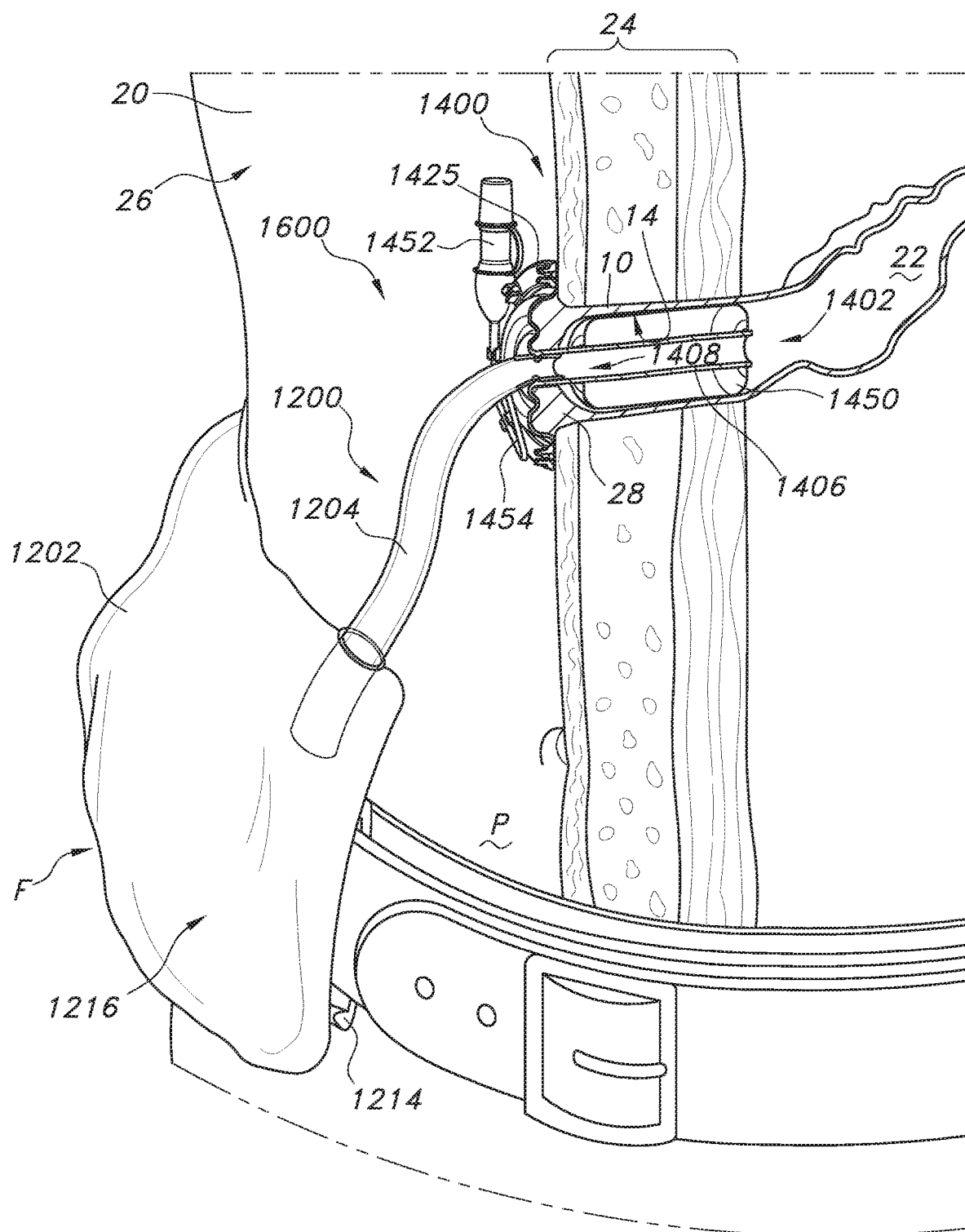
FIG. 16 provides a cross-section view of a waste collection system assembled for the collection of waste from a gastrointestinal organ of a patient, according to an exemplary embodiment of the present subject matter.

As previously described, the connection portion 1414 defined at the proximal end 1404 of the device 1400 may receive a connector of a waste collection apparatus, which extends the path 1408 for movement of waste into the waste collection apparatus. Exemplary waste collection apparatus 200 and 1200 are described above and illustrated in FIGS. 5, 9, 10, 12, and 13. Turning to FIG. 16, a schematic illustration is provided of a waste collection system according to another exemplary embodiment of the present subject matter. As shown in FIG. 16, the exemplary waste collection system 1600 is positioned to collect waste from lower GI organ 22 of the patient P through stoma 10, which may be formed as previously described. More particularly, a device 1400 is inserted into stoma 10 such that distal end 1402 of device 1400 is positioned at or within lower GI organ 22. In the depicted embodiment, a waste collection apparatus 1200 is connected to the device 1400; in other embodiments, a waste collection apparatus 200 may be connected to the device 1400. Collection apparatus 1200 is connected to device 1400 via connection portions 1414, 1226 of device 1400 and apparatus 1200, respectively. For example, the connection portion 1414 of device 1400 may include a protrusion or rib that is received within the groove 1228 of connection portion 1226 of apparatus 1200, thereby coupling or the device 1400 and apparatus 1200 and providing a path for the movement of waste from lower GI organ 22 to waste pouch 1202. The connection mechanism of device 1400 and collection apparatus 1200 sealingly connects the device 1400 and collection apparatus 1200, e.g., via a snap fit, interference fit, or other suitable connection between device 1400 and apparatus 1200. Thus, FIG. 16 illustrates waste collection system 1600 assembled for the collection of waste from lower GI organ 22 of patient P that would otherwise move through stoma 10.

It will be appreciated that, when device 1400 is inserted into stoma 10, the sealing mechanism 1450 is in its insertion position, in which the sealing mechanism 1450 generally conforms to the outer diameter $D_T$ of tube 1406 or assumes a position in which the sealing mechanism 1450 is smaller than the outer diameter $D_T$ of tube 1406. Once the device 1400 is inserted into stoma 10, the tube 1406 is positioned within stoma 10 and the connection portion 1414 is positioned adjacent external portion 28 of lower GI organ 22. In the depicted embodiment of FIG. 16, sealing mechanism 1450 is an inflatable balloon or cuff that is inflated to retain device 1400 within stoma 10 and to seal stoma 10 against leakage of waste around tube 1406, e.g., such that waste moves only out of device 1400 and into waste pouch 1202. More specifically, a fluid (such as, e.g., air or a saline solution) may be introduced to sealing balloon 1450 through inflation valve 1452 and inflation line 1454 to inflate sealing balloon 1450. When inflated, i.e., when in the sealing position and inflated to its inflated diameter $D_{SB}$, the sealing balloon 1450 expands against a surface 14 of the stoma 10 such that the sealing balloon 1450 contacts stoma 10 to create an effective seal and thereby reduce leakage around the sealing balloon. As described above, the inflated diameter $D_{SB}$ of sealing balloon 1450 is greater than the diameter $D_T$ of tube 1406, and in some embodiments, the inflated diameter $D_{SB}$ may be about 1.2 to about 1.5 times greater than the tube diameter $D_T$. Further, as previously stated, the sealing balloon 1450 may be a thin-wall, high-volume, low-pressure cuff, which may effectively seal stoma 10 without imparting too great a pressure to the tissue forming stoma 10. Additionally, as shown in FIG. 16, the sealing mechanism 1450 extends along substantially the entire length of tube 1406. As such, the sealing mechanism 1450 may have an extended axial length compared to retention mechanisms 120, 1120 described above.

Moreover, in appropriate embodiments, device 1400 and collection apparatus 1200 may be coupled such that waste collection system 1600 effectively is one piece. As one example, connector 1208 of collection apparatus 1200 may be sealingly connected, coupled, or attached to connection portion 1414 of tube 1406 of device 1400. As such, waste collection system 1600 may be configured for single use, such that the component that is placed within stoma 10 (e.g., tube 1406) is disposable with waste pouch 1202. Of course, even if not configured as a single piece waste collection system 1600, the components of the system may be configured for single, one-time use. Other configurations of waste collection system 1600 as occur to one of ordinary skill in the art may be used as well.

Similar to the depicted embodiment of FIG. 13, in the embodiment of FIG. 16 conduit 1204 is configured as a transition between device 1400 and waste pouch 1202. That is, waste emptied from organ 22 via tube 1406 of device 1400 passes through connector 1208 of collection apparatus 1200 and into conduit 1204 before the waste is collected in waste pouch 1202. As described in greater detail with respect to FIG. 13, conduit 1204 permits some flexibility as to where waste pouch 1202 is supported and in selecting an appropriately-sized waste pouch 1202 for patient P. More particularly, conduit 1204 permits waste pouch 1202 to be supported away from stoma site 12, and the configuration of conduit 1204 may be selected based on a variety of variables as described above.

To assemble waste collection system 1600 for collection of waste from body 20 of patient P, stoma 10 first must be formed in body 20. Stoma 10 may be pre-existing, i.e., patient P may have used other systems for collecting waste before using waste collection system 1600, or stoma 10 may be newly formed for use with system 1600. As previously described, stoma 10 and stoma site 12 are formed by pulling a portion of lower GI organ 22 through abdominal wall 24 to outer surface 26 of body 20, such that the pulled-through portion is external portion 28 of organ 22. Then, device 1400, in its insertion position, is inserted into stoma 10. Sealing mechanism 1450 is then deployed, e.g., by inflating a sealing balloon, to place sealing mechanism 1450 in its sealing position and thereby seal stoma 10 from the passage of waste through the stoma rather than tube 1406. When the device 1400 is positioned within stoma 10 and retained by sealing mechanism 1450, the distal end 1402 of device 1400 is positioned at organ 22 to receive waste from the organ. Waste may then move from organ 22 through path 1408 formed by tube 1406 of device 1400. However, a seal or valve at proximal end 1404 (e.g., seal or valve 1115) or another valve within tube 1406 (e.g., valve 134) may arrest the movement of waste, e.g., until a collection apparatus 1200 is connected to device 1400.

To connect apparatus 1200 to device 1400, tubular portion 1210 of connector 1208 is inserted into tube 1406 at proximal end 1404 of device 1400. Connection portion 1226 of connector 1208 interfaces or engages with connection portion 1414 of tube 1406 to connect collection apparatus 1200 to device 1400. Attachment mechanism(s) 1214 may be attached to a support for supporting collection apparatus 1200; the attachment mechanism(s) 1214 may be attached to the support before the connector 1208 is inserted into tube 1406. Waste may then move through tube 1406, tubular portion 1210 of connector 1208, conduit 1204, and into waste pouch 1202. When waste pouch 1202 is full, or when the movement of waste has stopped, connector 1208 may be disconnected and waste pouch 1202 emptied or discarded. As previously stated, waste collection apparatus 200 or another suitable collection apparatus described herein, rather than apparatus 1200, may be connected to device 1400 for the collection of waste from stoma 10.

Figure 17:
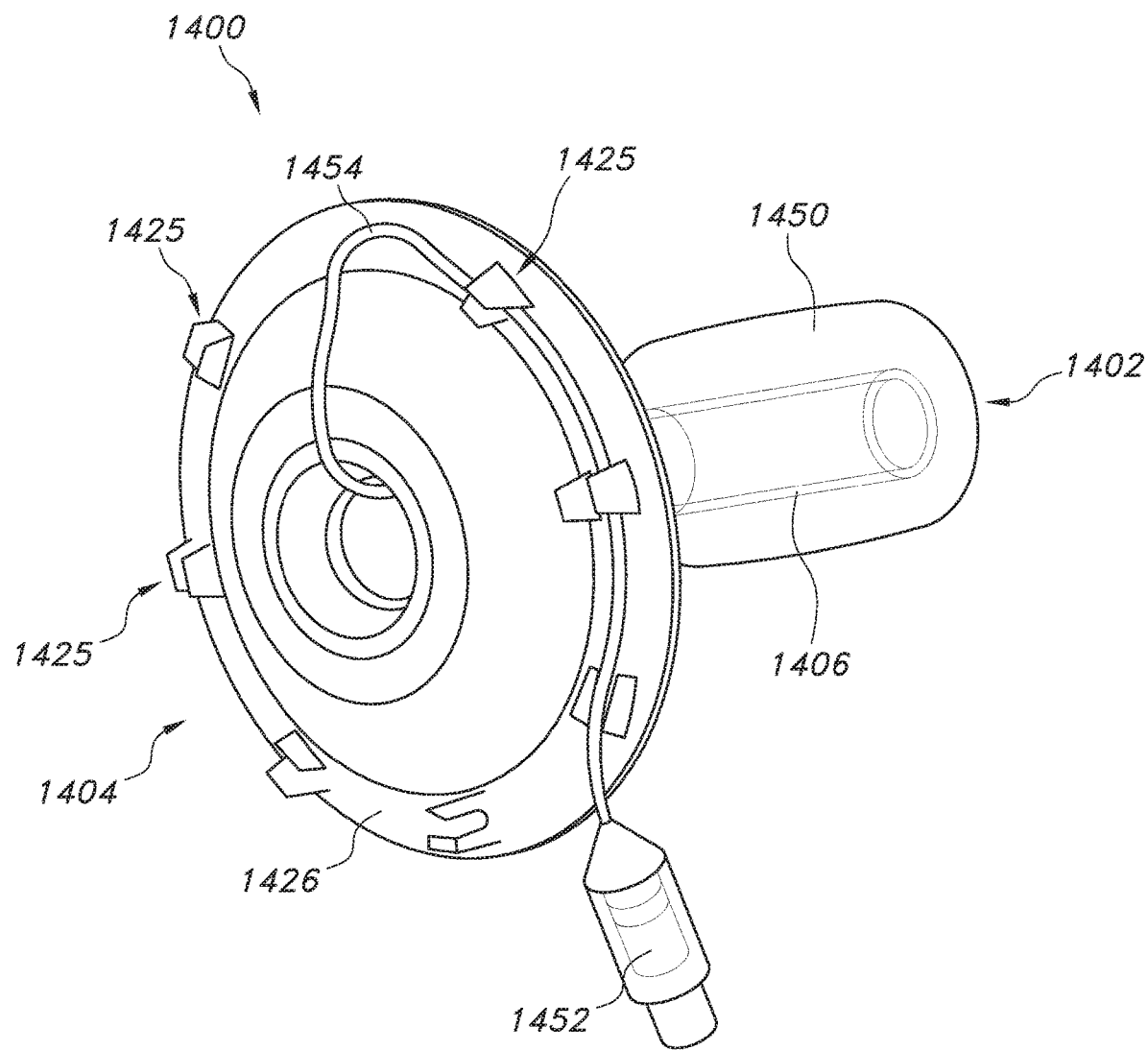
FIG. 17 provides a perspective view of the device of FIG. 14, according to another exemplary embodiment of the present subject matter.

Referring now to FIG. 17, the device 1400 is shown according to another exemplary embodiment of the present subject matter. As illustrated in FIG. 17, the valve 1452 of the device 1400 is more loosely positioned with respect to the barrier 1426 than the valve 1452 shown in FIGS. 14 and 15. As such, the valve 1452 for inflating the sealing mechanism 1450 can more easily adapt to the structure of a waste collection apparatus that may be attached to the device 1400 for the collection of waste from the patient's body. That is, the valve 1452 illustrated in FIG. 17 can be more easily positioned with respect to a waste collection apparatus than, e.g., the valve 1452 illustrated in FIGS. 14 and 15 and, thus, the device of 1400 of FIG. 17 may be better suited for use with some waste collection apparatus than the device 1400 illustrated in FIGS. 14 and 15.

Figure 18:
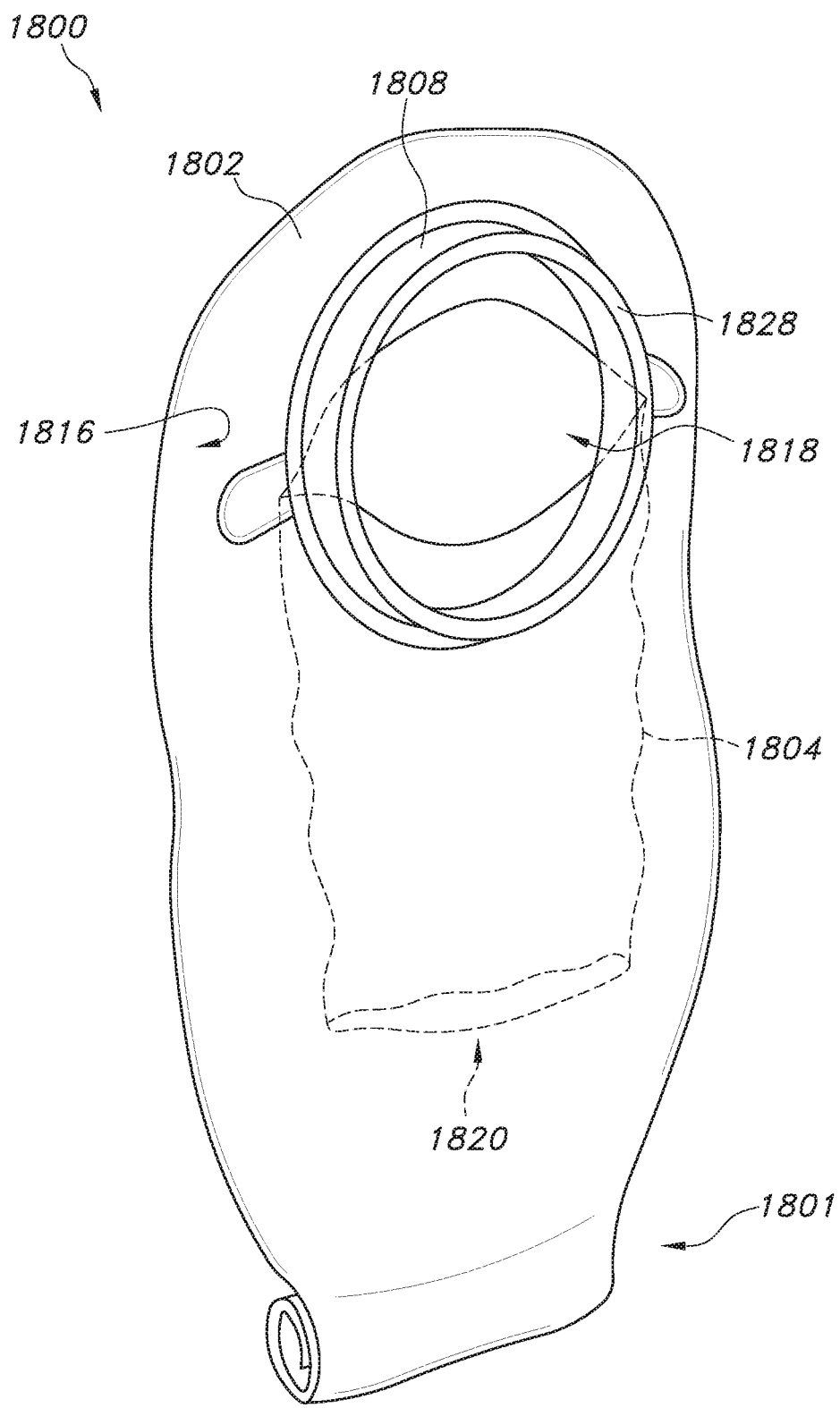
FIG. 18 provides a perspective view of a collection apparatus for collecting waste moving through a stoma formed in a body of a patient, according to an exemplary embodiment of the present subject matter.

Turning to FIG. 18, a perspective view is provided of a collection apparatus for collecting waste moving through a stoma formed in a body of a patient, according to another exemplary embodiment of the present subject matter. The waste collection apparatus 1800 described with respect to FIG. 18 has several features in common with the collection apparatus 200 and 1200 described above. However, the collection apparatus 1800 also has some features that are different from or configured differently than similar features of the previously described collection apparatus.

As depicted in FIG. 18, the waste collection apparatus 1800 includes a waste bag or a waste pouch 1802, a transition duct 1804, and a connector 1808. Waste pouch 1802 collects waste rejected from the body through the stoma formed in the body. More particularly, the connector 1808 is attached to the waste pouch 1802 for coupling the collection apparatus 1800 to a device received within the stoma, e.g., device 1400 described above, such that waste moves through the device to the collection apparatus 1800, where it is collected in waste pouch 1802. Collection apparatus 1800 also may include one or more attachment mechanisms (not shown) for attaching collection apparatus 1200 to a support such as, e.g., the patient's clothing or a healthy portion of the patient's body away from the stoma. The support can help support the weight of collection apparatus 1800, particularly when it is filled with waste. As described with respect to other embodiments of collection apparatus, the attachment mechanism(s) may be coupled to an outer surface 1816 of waste pouch 1802 using any appropriate fastener or fastening mechanism, and the attachment mechanisms may be any appropriate mechanism or combination of mechanisms for attaching collection apparatus 1800 to an appropriate support.

As further illustrated in FIG. 18, the transition duct 1804 extends within waste pouch 1802 from connector 1808 toward a bottom portion 1801 of waste pouch 1802. That is, the transition duct 1804 is enclosed within the waste pouch 1802 and extends from an open first end 1818 to an open second 1820. The second end 1820 of transition duct 1804 is positioned toward the bottom portion 1801 of waste pouch 1802 to direct waste toward the bottom of the waste pouch 1802 such that waste pouch 1802 fills from the bottom toward the top. The transition duct 1804 may be generally configured as a sleeve having first open end 1818 and second open end 1820. The transition duct 1804 may be bonded to an interior surface of waste pouch 1802, e.g., such that the waste pouch 1802 supports the transition duct 1804 and/or keeps the transition duct 1804 in a certain position or orientation. In some embodiments, the transition duct 1804 is flexible such that the transition duct 1804 can expand or flex away from the inner surface of waste pouch. For example, the transition duct 1804 may be formed from a film or film-like material, which collapses generally against the inner surface of waste pouch 1802 when no waste is moving through the transition duct and expands or flexes away from the inner surface as waste moves therethrough. As such, the transition duct 1804 may exert little force on any waste moving through the transition duct, and the pressure that causes the waste to move toward the transition duct 1804 is sufficient to move the waste through the transition duct.

Referring particularly to connector 1808, the connector 1808 includes one or more features for connecting to, e.g., a device positioned within a stoma formed in a patient's body, such as device 1400, or a connection component that helps form a connection between the collection apparatus and the device. As described above, the connection portion 1414 of device 1400 may define a groove or a protrusion or rib defined along an inner surface 1418 of the connection portion 1414. The connector 1808 of collection apparatus 1800 includes one or more features to help connect the waste pouch 1802 to a device positioned in a stoma formed in a patient's body and to help seal the connection such that waste may move through the device to the waste pouch without leaking through the connection between the pouch and the device. In an exemplary embodiment, the collection apparatus 1800 connects to the connection portion 1414 of a device 1400. As previously described, connection portion 1414 may have any suitable configuration to mechanically or otherwise fasten or attach a waste pouch or other apparatus to device 1400. As depicted in FIG. 18, the connector 1808 defines a protrusion or rib 1828, which would mate with a groove defined in connection portion 1414 of device 1400. Alternatively, the protrusion 1828 of connector 1808 may mate with a groove defined in a connection component 1900, as described in greater detail below. Connector 1808 and either connection portion 1414 of device 1400 or connector component 1900 generally may be described as a connection assembly, where protrusion 1828 is a male portion of the mechanical connection assembly and the groove of connection portion 1414 or connector component 1900 is a female portion of the assembly. In other embodiments, connection portion 1414 or connector component 1900 may define the male portion of the connection assembly and connector 1808 of collection apparatus 1800 may define the female portion of the assembly. Of course, as previously described, connection portion 1414 or connector component 1900 may have other configurations and, similarly, connector 1808 may have other configurations to mechanically or otherwise fasten or attach waste pouch 1802 to device 1400 or another device to receive waste from a patient's body.

As described above with respect to other collection apparatus, collection apparatus 1800 may incorporate one or more features for controlling odors, wet spots, irritation, or other undesirable conditions that could occur when collection apparatus 1800 receives waste. For example, as previously described with respect to other waste pouches, the waste pouch 1802 may include a layer of liquid impervious film to help prevent liquids from soaking through the pouch 1802, or waste pouch 1802 may include a coating or integrated material or formulation that is selectively permeable to one or more gases such that the pouch 1802 does not balloon or swell and/or does not emit odors. Of course, other coatings, films, or the like also may be used to prevent undesirable conditions of collection system 1800. Additionally, the waste pouch 1802 may be made from a nonwoven material, e.g., a SMS material, which may improve patient comfort as well as impart strength and barrier properties to the waste pouch 1802. Nonwoven and SMS materials are described in greater detail above with respect to other waste pouches, and such discussion is also applicable to nonwoven and SMS materials that may be used to produce waste pouch 1802.

Figure 19:
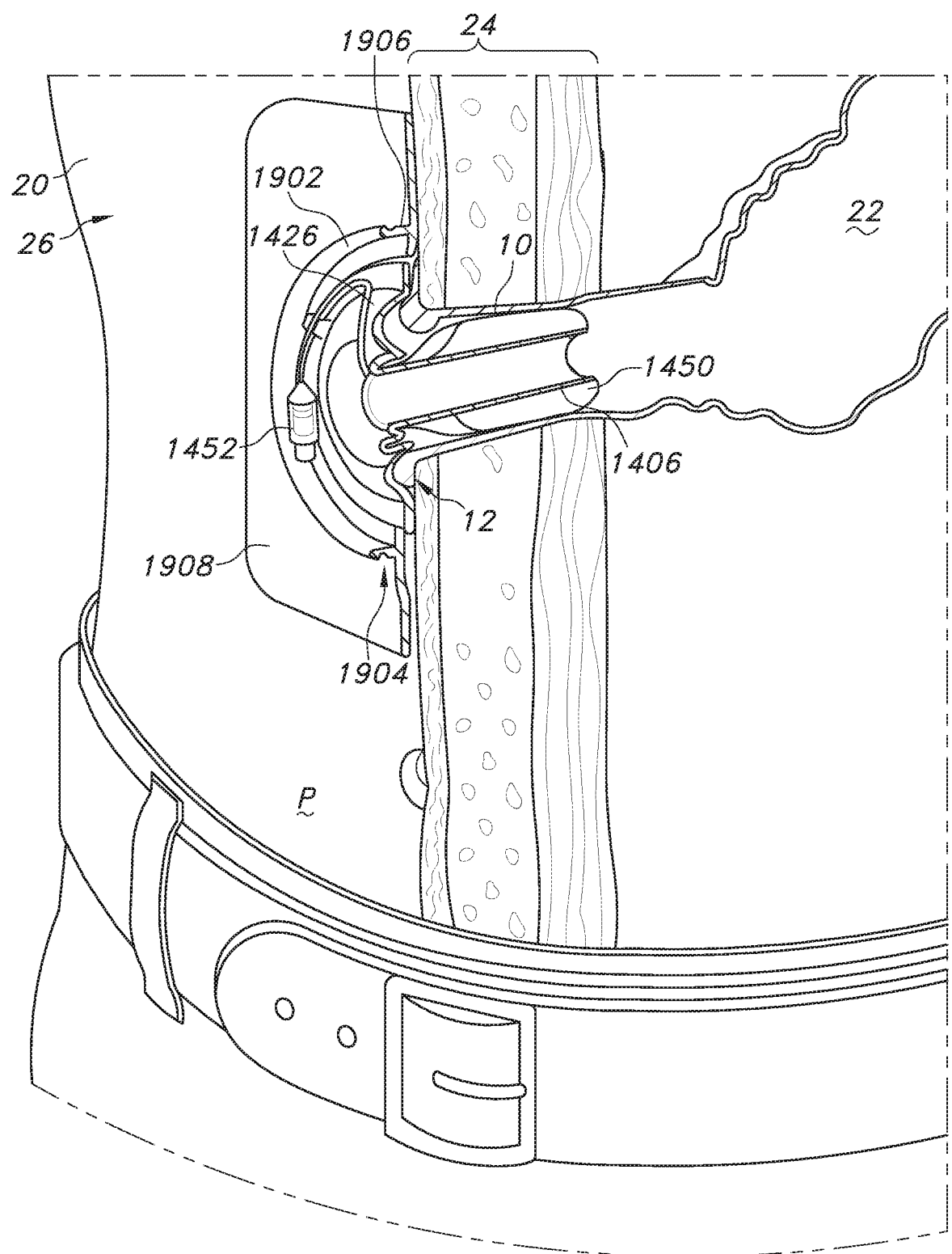
FIG. 19 provides a cross-section view of a connection component and the device of FIG. 17 inserted into a stoma formed in the body of a patient and having a sealing mechanism in a sealing position, according to an exemplary embodiment of the present subject matter.

Turning to FIG. 19, an illustration is provided of a connection component 1900 assembled with a device 1400 that has been positioned in a stoma 10 formed in the body 20 of patient P, according to an exemplary embodiment of the present subject matter. As shown in FIG. 19, the sealing mechanism 1450 of the device 1400 is deployed to seal the stoma 10 and retain the device 1400 within the stoma 10. More particularly, in the illustrated embodiment, the sealing mechanism 1450 is an inflatable sealing balloon, which is in an inflated position to thereby seal stoma 10 as well as retain device 1400 in the stoma 10.

Figure 20:
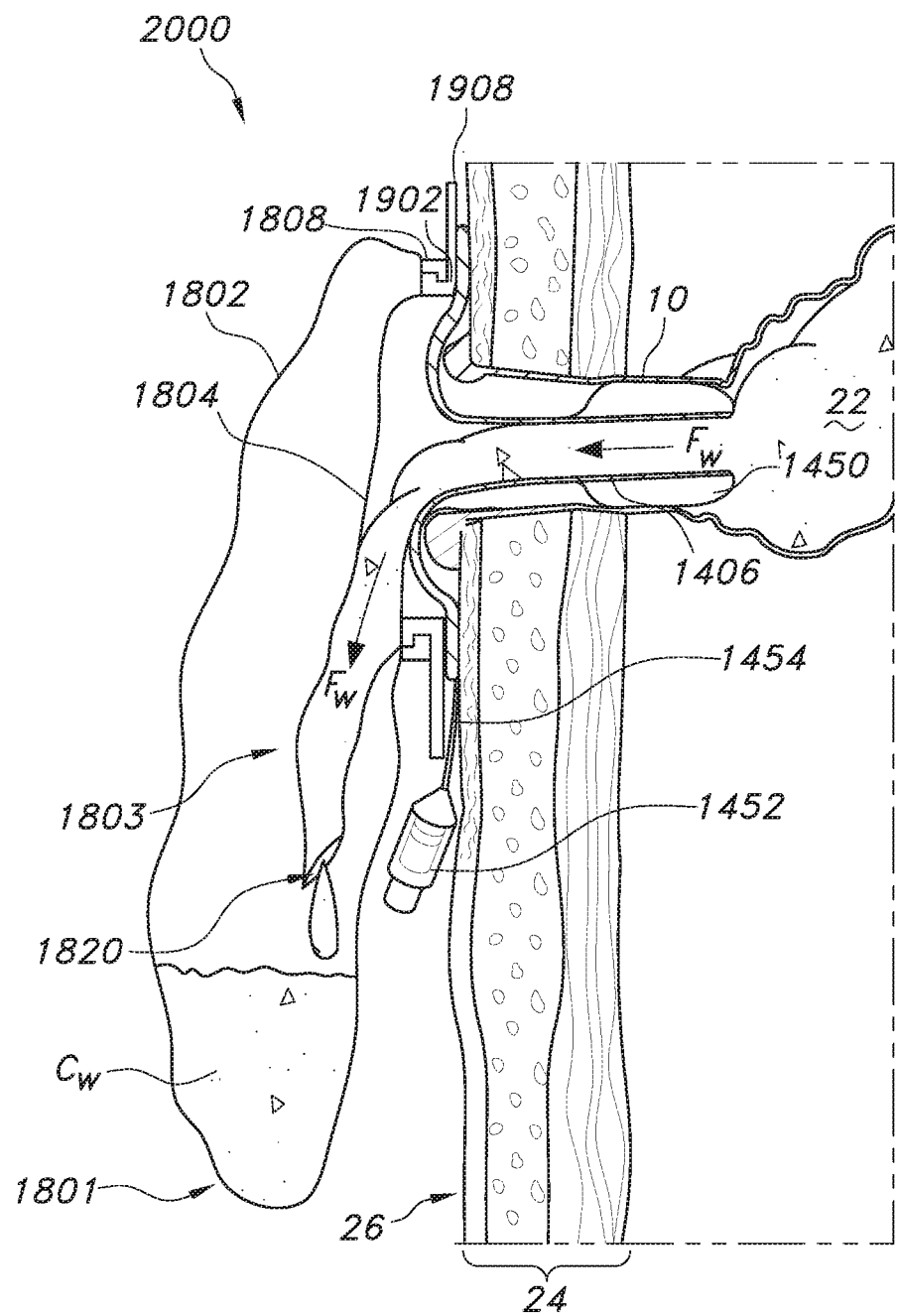
FIG. 20 provides a cross-section view of a waste collection system assembled for the collection of waste from a gastrointestinal organ of a patient, according to an exemplary embodiment of the present subject matter.

The connection component 1900 includes a connection portion 1902 projecting away from the body 20 of patient P. Although a cross-sectional view is provided, it will be appreciated that the illustrated connection portion 1902 has a generally circular shape to match the circular shape of connector 1808 of collection apparatus 1800, such that the connector 1808 can connect to the connection component 1900 as shown in FIG. 20. More specifically, the connection portion 1902 is configured in the depicted embodiment as a circular wall and defines a groove 1904 around its outer surface 1906. As described above, the connector 1808 includes a protrusion 1828, which mates with the groove 1904 to connect the collection apparatus 1800 to the connection component 1900. Further, the protrusion 1828 mates with the groove 1904 to seal the connection between the collection apparatus 1800 and the connection component 1900 such that waste may flow from the tube 1406 of the device 1400 and into waste pouch 1802 without leaking through the connection between the connector 1808 and the connection portion 1902. For instance, a snap fit or interference fit may be used between the collection apparatus 1800 and the connection component 1900, and it will be understood that, as previously described, the connector 1808 or the connection component 1900 may include the male portion of the connection assembly formed by the two components, while the other component includes the female portion of the assembly.

Keeping with FIG. 19, the connection component 1900 also includes a barrier 1908. The barrier 1908 extends away or outward from the connection portion 1902, but the barrier 1908 also may extend inward from the connection portion 1902. That is, the barrier 1908 may define an opening through which the device 1400 protrudes, or the connection portion 1902 may define such opening. In embodiments in which the barrier 1908 defines the opening through which the external portion of device 1400 protrudes, as shown in FIG. 19, a portion of the barrier 1908 may be positioned between the barrier 1426 of device 1400 and the outer surface 26 of patient P, i.e., between barrier 1426 and the patient's skin. In any event, the barrier 1908 extends outward from the connection portion 1902 such that the barrier 1908 is positioned against the outer surface or skin 26 of patient P. As such, the barrier 1908 may help support a collection apparatus connected to the connection component 1900, e.g., the barrier 1908 may distribute the weight of an attached collection apparatus such that the weight of the apparatus is not concentrated at the stoma site 12. Barrier 1908 may serve other purposes as well, such as, e.g., the barrier 1908 may help keep the stoma site 12 clean as used waste pouches are exchanged for unused waste pouches.

The connection component 1900 may be secured to the body 20 of patient P or to the device 1400. For example, the connection component 1900 may be secured to patient P using a suitable adhesive, such as a medical tape or the like. In other embodiments, the connection component 1900 may be secured to the device 1400 may suitable mechanical or other mechanisms, e.g., a connection assembly defined by the connection component 1900 and device 1400 may be formed that is similar to the connection assembly described above that is defined by the collection apparatus 1800 and the connection component 1900. Other suitable mechanisms for securing the connection component 1900 may be used as well.

Referring now to FIG. 20, a waste collection system for collecting waste from a body of a patient is illustrated. Generally, the waste collection system 2000 comprises device 1400, collection apparatus 1800, and connection component 1900 to collect waste that would otherwise move through stoma 10 formed in body 20 of patient P. More particularly, in waste collection system 2000, connector 1808 of collection apparatus 1800 interfaces with connection component 1900 to position the waste pouch 1802 in communication with tube 1406 of device 1400 positioned in stoma 10 to thereby facilitate the collection of waste from body 20.

A typical ostomy procedure is described above, and FIG. 20 provides a schematic illustration of waste collection system 2000 positioned to collect waste from lower GI organ 22 of the patient P through stoma 10. As shown in FIG. 20, the device 1400 is inserted into stoma 10 such that distal end 1402 of device 1400 is positioned at or within lower GI organ 22. It will be appreciated that, when device 1400 is inserted into stoma 10, sealing mechanism 1450 is in its insertion position, in which the sealing mechanism 1450 generally conforms to the outer diameter $D_T$ of the tube 1406.

As further illustrated in FIG. 20, the sealing mechanism 1450 may be deployed to help seal the stoma 10 such that waste moves only out of device 1400 and into waste pouch 1802. In the exemplary embodiment shown in FIG. 20, the sealing mechanism 1450 is an inflatable balloon or cuff, such as a thin-wall, high-volume, low-pressure cuff, and may be deployed within stoma 10 as described above with respect to the waste collection system 1600 depicted in FIG. 16. Moreover, collection apparatus 1800 is connected to device 1400 via connection component 1900. More particularly, the protrusion 1828 of connector 1808 is received within the groove 1904 of connection component 1900, positioning the first open end 1818 of the transition duct at the proximal end 1404 of the tube 1406 and thereby providing a path for a flow of waste $F_W$ from lower GI organ 22 to waste pouch 1802. As described above, the protrusion 1828 may snap into groove 1904 such that collection apparatus 1800 and connection component 1900 connection via a snap fit, and the collection apparatus 1800 may sealingly connect to the connection component 1900 to prevent leakage of waste through the connection.

As depicted in FIG. 20, transition duct 1804 directs the flow of waste $F_W$ to the bottom portion 1801 of waste pouch 1802. That is, waste emptied from organ 22 via tube 1406 of device 1400 passes through the first open end 1818 and into transition duct 1804, through which the waste travels to the second open end 1820 and into the interior 1803 of waste pouch 1802. As such, the waste CW is collected in waste pouch 1802 starting at the bottom portion 1801 of the waste pouch, and waste pouch 1802 accordingly fills from the bottom up.

As will readily be understood from the foregoing description and FIG. 20, to assemble waste collection system 2000 for collection of waste from body 20 of patient P, stoma 10 first must be formed in body 20. Stoma 10 may be pre-existing, i.e., patient P may have used other systems for collecting waste before using waste collection system 2000, or stoma 10 may be newly formed for use with system 2000. As previously described, stoma 10 and stoma site 12 are formed by pulling a portion of lower GI organ 22 through abdominal wall 24 to outer surface 26 of body 20, such that the pulled-through portion is external portion 28 of organ 22. Then, device 1400, in its insertion position, is inserted into stoma 10 such that distal end 1402 of device 1400 is positioned at organ 22 to receive waste from the organ. Sealing mechanism 1450 is deployed, e.g., by inflating a sealing balloon, to place sealing mechanism 1450 in its sealing position and thereby seal stoma 10 from the passage of waste through the stoma rather than tube 1406. The sealing mechanism 1450 also helps retain the device 1400 within stoma 10. Waste may then move from organ 22 through path 1408 formed by tube 1406 of device 1450. However, a seal or valve, or such as similar to seal or valve 1115 or valve 134 described with respect to device 100, may arrest the movement of waste, e.g., until a collection apparatus is connected to device 1400.

To connect collection apparatus 1800 to device 1400, connection component 1900 is positioned at barrier 1426 of device 1400. In some embodiments, the connection component 1900 is positioned with its opening around stoma site 12 before device 1400 is inserted into stoma 10, e.g., such that a portion of barrier 1426 overlaps barrier 1908 of connection portion 1900. In other embodiments, connection portion 1900 is positioned after device 1400 is inserted into stoma 10. Connector 1808 of collection apparatus 1800 interfaces or mates with connection portion 1902 of connection component 1900 to connect the apparatus 1800 to connection component 1900 and thereby position waste pouch 1802 in communication with tube 1406. If provided, the attachment mechanism(s) of apparatus 1800 may be attached to a support for supporting collection apparatus 1800; the attachment mechanism(s) may be attached to the support before or after the connector 1808 is connected to the connection component 1900. Waste may then move through tube 1406, transition duct 1804, and into the bottom portion 1801 of waste pouch 1802. When waste pouch 1802 is full, or when the movement of waste has stopped, connector 1808 may be disconnected and waste pouch 1802 emptied or discarded.

Figure 21:
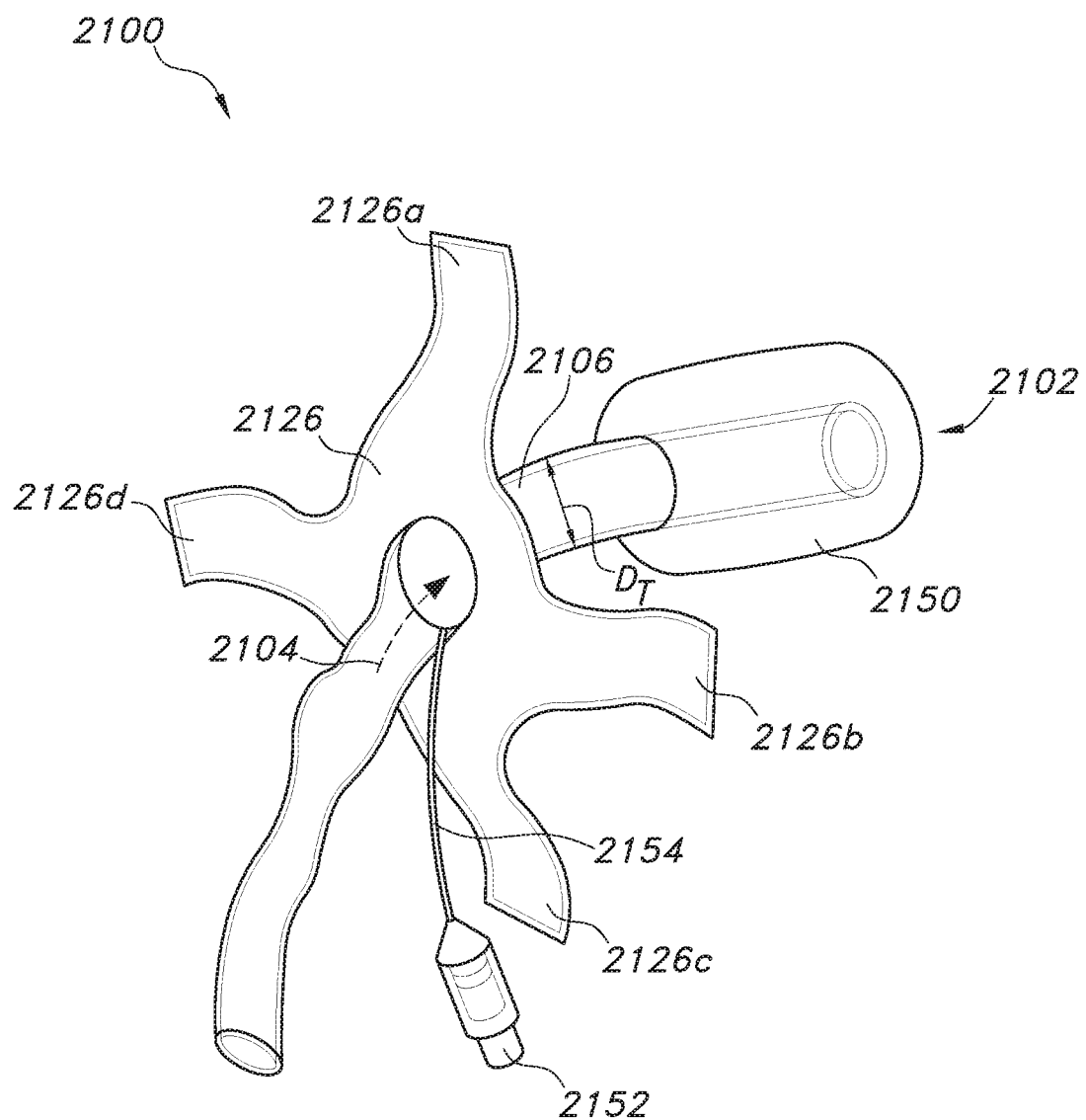
FIG. 21 provides a perspective view of a device for insertion into a stoma formed in a body of a patient, according to an exemplary embodiment of the present subject matter, the device having an integral transition duct and a sealing mechanism shown in a sealing position.
Figure 23:
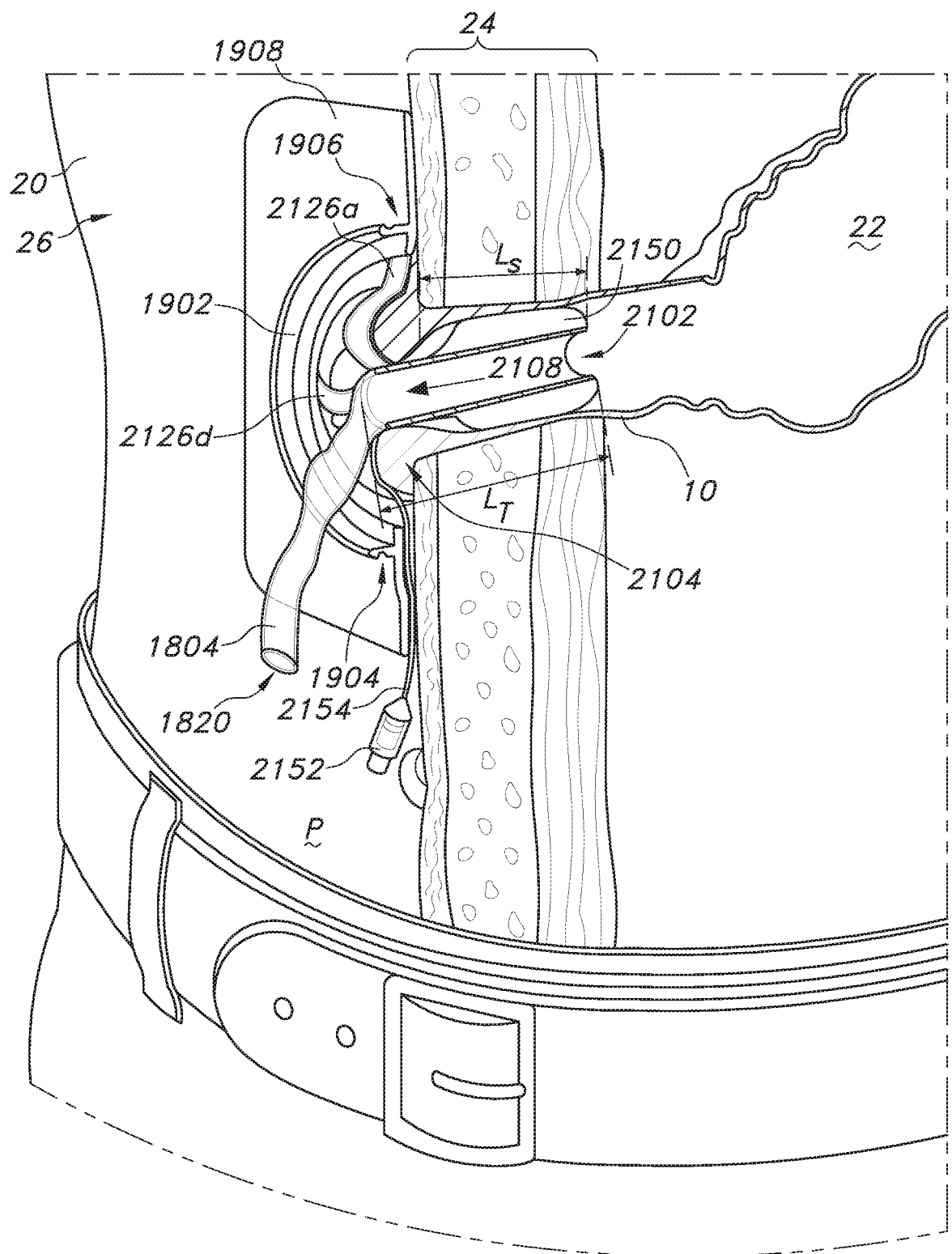
FIG. 23 provides a cross-section view of a connection component and the device of FIG. 21 inserted into a stoma formed in the body of a patient and having a sealing mechanism in a sealing position, according to an exemplary embodiment of the present subject matter.

Turning now to FIG. 21, a device for insertion into a stoma formed in a body of a patient is illustrated, according to another exemplary embodiment of the present subject matter. Similar to devices 100, 1100, and 1400 described above, the device 2100 defines an axial direction A and includes a tube 2106 extending along the axial direction A between a distal end 2102 and a proximal end 2104 (FIG. 23). As shown in FIG. 23, the tube 2106 defines a path 2108 for movement of waste or effluent through a stoma 10 defined in the body 20 of a patient P. The tube 2106 has a length $L_T$ and an outer diameter $D_T$. As described with respect to other devices, the tube 2106 may be tapered from one of ends 2102, 2104 toward the other end, may have a varying outer diameter $D_T$ along its length $L_T$, or may have a constant outer diameter $D_T$ from one end 2102, 2104 to the other. Further, the tube 2106 may be rigid, flexible, or fully or partially collapsible; expandable, non-expandable, or partially expandable; soft or hard; or any appropriate combination of the foregoing. Moreover, tube 2106 may be relatively thin walled, e.g., to permit as large of an inner diameter and/or cross-sectional area as possible for the movement of waste through tube 2106. Tube 2106 may have other configurations as well.

As further depicted in FIG. 21, the device 2100 includes a flange or barrier 2126 at the proximal end 2104 of the tube 2106. The barrier 2126 may be positioned over an external portion 28 of the patient's organ at the stoma site 12, as shown in FIG. 23. The barrier 2126, e.g., may help stabilize an external portion of the device 2100, ensure the device 2100 is inserted to a proper depth by providing an external stop against further insertion, and/or protect the stoma site 12. The barrier 2126 may comprise a plurality of arms, e.g., arms 2126a, 2126b, 2126c, 2126d, as shown in FIG. 21, and each arm may be secured to the patient's body 20 using a suitable adhesive or other securement mechanism. Alternatively, the barrier 2126 may be configured similar to the barrier 126 of device 100 or barrier 1426 of device 1400, but other configurations of barrier 2126 may be used as well.

In the illustrated embodiment of FIG. 21, the device 2100 includes a sealing mechanism 2150. Similar to the other sealing mechanisms described herein, the sealing mechanism 2150 has an insertion position and a sealing position; the sealing mechanism is shown in the sealing position in FIG. 21. Further, the sealing mechanism 2150 extends axially along at least a portion $L_S$ of the length $L_T$ of the tube 2106 between the proximal end 2104 and the distal end 2102 of the tube 2106. In the depicted embodiment, the sealing mechanism 2150 extends over a substantial portion of the length $L_T$ of tube 2106 such that the device 2100 includes a sealing mechanism 2150 along an extended axial length of tube 2106. Moreover, in the depicted embodiment, sealing mechanism 2150 is an inflatable balloon or cuff, which is deflated in the insertion position of the sealing mechanism 2150 and inflated in the sealing position of the sealing mechanism 2150. For example, the sealing balloon 2150 may be substantially similar to the sealing balloons 1150, 1450 described above, e.g., sealing mechanism 2150 may be a thin-wall, high-volume, low-pressure cuff such as a Microcuff® balloon having an inflated diameter in the ranges described with respect to sealing balloons 1150, 1450. For example, the sealing balloon may have an inflated diameter $D_{SB}$ that is from about 1.1 times to about twice the diameter $D_T$ of tube 2106, and in particular embodiments, the inflated diameter $D_{SB}$ is from about 1.2 times to about 1.5 times the outer diameter $D_T$ of tube 2106. Of course, the sealing mechanism 2150 may have other configurations as well.

In embodiments in which the sealing mechanism 2150 is a sealing balloon, an inflation valve 2152 and an inflation line 2154 may be provided for inflating the sealing balloon. As shown in FIGS. 21 and 23, the inflation line 1454 may extend from the sealing balloon through the stoma 10 to inflation valve 1452 located outside of the patient's body 20. A length of inflation line 1454 outside of stoma 10 may be located outside of the patient's body 20, e.g., to allow the inflation valve 20 to be positioned in an appropriate location for inflating the sealing balloon 2150 or to avoid a waste collection apparatus connected to the device 2100. Other configurations of inflation valve 2152 and inflation line 2154 also may be used, e.g., inflation line 2154 may be incorporated into tube 2106. It also will be readily understood by those of ordinary skill in the art that other sealing mechanisms 2150 than an inflatable sealing balloon may be used as well, such as a flexible diaphragm or other mechanical means of retention and sealing along a length $L_S$ of the tube 2106 within stoma 10.

Additionally, the device 2100 includes an integrated transition duct 1804. As described with respect to FIG. 18, in some embodiments, the transition duct 1804 is integral with the waste pouch 1802 of collection apparatus 1800, such that the transition duct 1804 extends within waste pouch 1802 from the connector 1808 toward a bottom portion 1801 of waste pouch 1802. In the embodiment of device 2100 illustrated in FIG. 21, the transition duct 1804 is integral with the tube 2106 such that the transition duct 1804 extends from the proximal end 2104 of the tube 2106 to open second end 1820 of the transition duct 1804. That is, the first end 1818 is integrally formed with or bonded to the tube 2106 such that the flow path 2108 defined by the tube 2106 extends through the integral transition duct 1804 as well. In some embodiments, the transition duct 1804 is flexible such that the transition duct 1804 can expand or flex, e.g., the transition duct 1804 may be formed from a film or film-like material, which collapses generally against itself when no waste is moving through the transition duct and expands or flexes away from itself as waste moves therethrough. As such, the transition duct 1804 of device 2100 may exert little force on any waste moving through the transition duct, and the pressure that causes the waste to move toward the transition duct 1804 is sufficient to move the waste through the transition duct.

Figure 22:
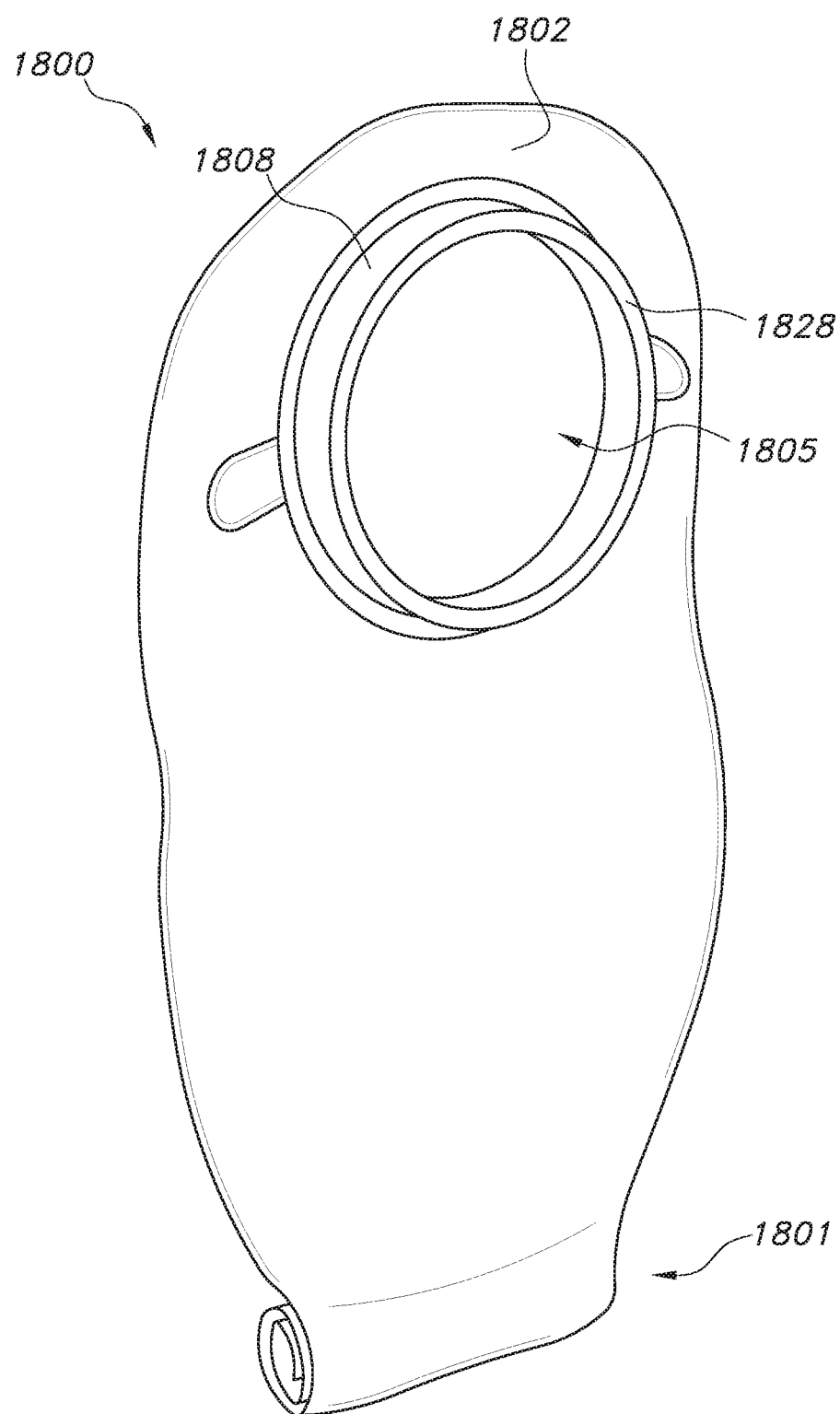
FIG. 22 provides a perspective view of the collection apparatus of FIG. 18, according to another exemplary embodiment of the present subject matter.

FIG. 22 illustrates an alternative embodiment of the waste collection apparatus 1800 described above and depicted in FIG. 18. Like previously described with respect to collection apparatus 1800, the embodiment shown in FIG. 22 includes a waste bag or a waste pouch 1802 and a connector 1808, which connects the waste pouch 1802 to a device inserted in a stoma formed in the body of a patient to collect waste rejected from the body. Unlike the embodiment shown in FIG. 18, the embodiment of collection apparatus 1800 shown in FIG. 22 does not include a transition duct 1804. Rather, connector 1808 defines an opening 1805 for the passage of waste from a device positioned in the stoma to the waste pouch 1802. Otherwise, the collection apparatus 1800 is substantially similar to the collection apparatus 1800 described with respect to FIG. 18, such that the remainder of the above discussion of the collection apparatus 1800 also applies to the embodiment shown in FIG. 22.

Turning to FIG. 23, an illustration is provided of a connection component 1900 assembled with a device 2100 that has been positioned in a stoma 10 formed in the body 20 of patient P, according to an exemplary embodiment of the present subject matter. The sealing mechanism 2150 of the device 2100 is deployed to seal the stoma 10 and retain the device 2100 within the stoma 10. More particularly, in the illustrated embodiment, the sealing mechanism 2150 is an inflatable sealing balloon, which is in an inflated position to thereby seal stoma 10 as well as retain device 2100 in the stoma 10. As further shown in FIG. 23, the connection component 1900 is substantially similar to the connection component 1900 described above and illustrated in FIG. 19. As such, as illustrated in FIG. 23, the connection component 1900 includes circular connection portion 1902, defining a groove 1904 in its outer surface 1906; the groove 1904 is configured to receive the protrusion or rib 1828 of collection apparatus 1800. The barrier 1908 of the connection component 1900 extends outward of connection portion 1902, as well as somewhat inward of connection portion 1902. In the embodiment depicted in FIG. 23, the barrier 1908 is positioned over the barrier 2126 of the device 2100 such that, where the barriers of the components overlap, the barrier 2126 of the device 2100 is between the outer surface or skin 26 of patient P and the barrier 1908 of connection component 1900.

Figure 24:
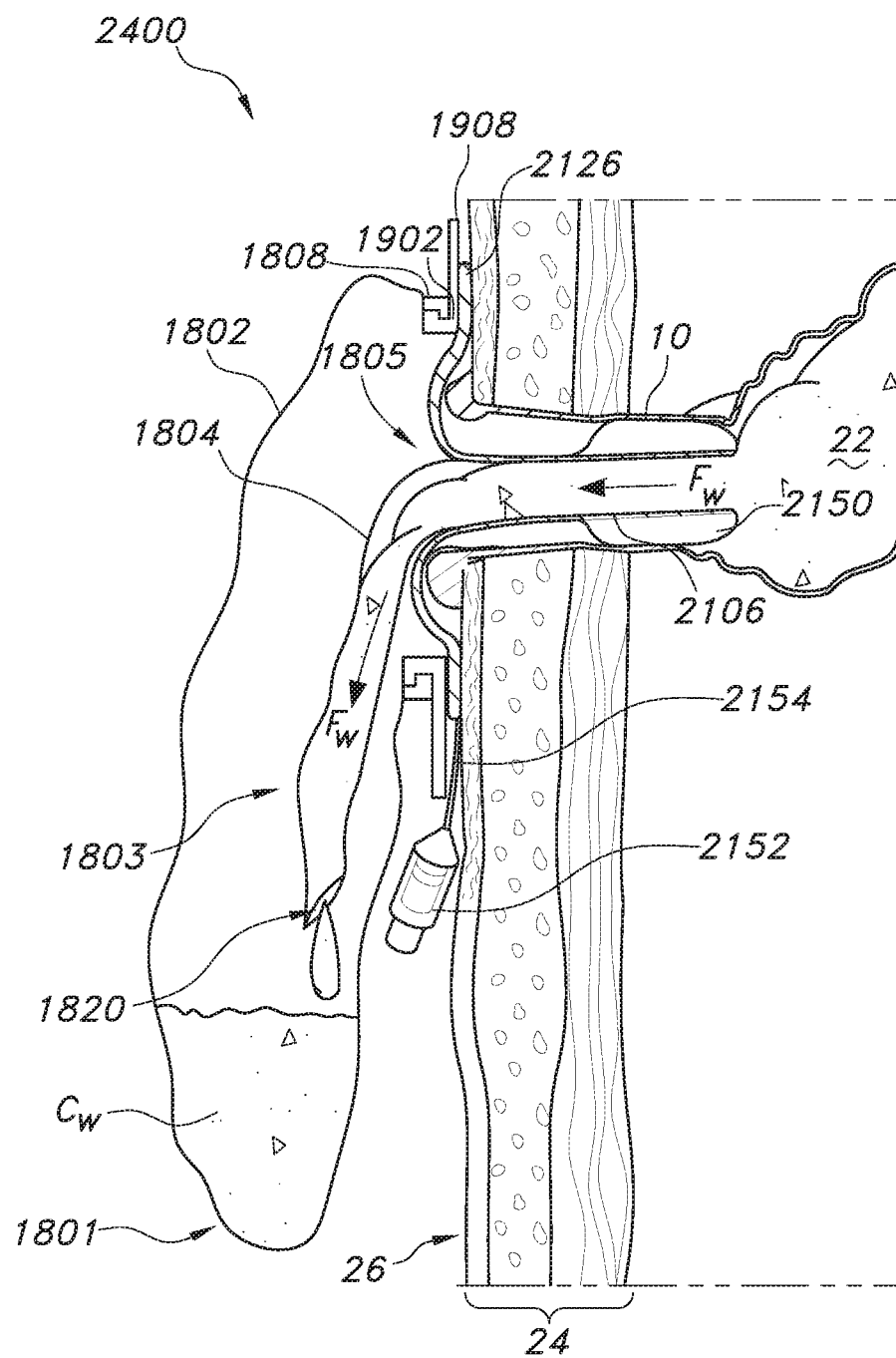
FIG. 24 provides a cross-section view of a waste collection system assembled for the collection of waste from a gastrointestinal organ of a patient, according to an exemplary embodiment of the present subject matter.

Referring now to FIG. 24, a waste collection system for collecting waste from a body of a patient is illustrated. Generally, the waste collection system 2400 comprises device 2100, collection apparatus 1800 of FIG. 22, and connection component 1900 to collect waste that would otherwise move through stoma 10 formed in body 20 of patient P. More particularly, in waste collection system 2400, the transition duct 1804 of device 2100 is received within waste pouch 1802 of collection apparatus 1800, and connector 1808 of collection apparatus 1800 interfaces with connection component 1900 to position the waste pouch 1802 for the collection of waste from body 20.

A typical ostomy procedure is described above, and FIG. 24 provides a schematic illustration of waste collection system 2400 positioned to collect waste from lower GI organ 22 of the patient P through stoma 10. As shown in FIG. 24, the device 2100 is inserted into stoma 10 such that distal end 2102 of device 2100 is positioned at or within lower GI organ 22. It will be appreciated that, when device 2100 is inserted into stoma 10, sealing mechanism 2150 is in its insertion position, in which the sealing mechanism 2150 generally conforms to the outer diameter $D_T$ of the tube 2106.

As further illustrated in FIG. 24, the sealing mechanism 2150 may be deployed to help seal the stoma 10 such that waste moves only out of device 2100 and into waste pouch 1802. In the exemplary embodiment shown in FIG. 24, the sealing mechanism 2150 is an inflatable balloon or cuff, such as a thin-wall, high-volume, low-pressure cuff, and may be deployed within stoma 10 as described above with respect to the waste collection system 1600 depicted in FIG. 16. Moreover, collection apparatus 1800 is connected to device 2100 via connection component 1900. More particularly, the protrusion 1828 of connector 1808 is received within the groove 1904 of connection component 1900, and with transition duct 1804 of device 2100 received within waste pouch 1802, a path for a flow of waste $F_W$ from lower GI organ 22 to waste pouch 1802. As described above, the protrusion 1828 may snap into groove 1904 such that collection apparatus 1800 and connection component 1900 connection via a snap fit, and the collection apparatus 1800 may sealingly connect to the connection component 1900 to prevent leakage of waste through the connection.

As depicted in FIG. 24, the integral transition duct 1804 of device 2100 is received within the waste pouch 1802 of collection apparatus 1800. The second end 1820 of transition duct 1804 is positioned toward the bottom portion 1801 of waste pouch 1802 to direct the flow of waste $F_W$ toward the bottom of the waste pouch 1802 such that waste pouch 1802 fills from the bottom toward the top. That is, waste emptied from organ 22 into tube 2106 of device 2100 passes through the integral transition duct 1804 of device 2100. The waste travels through the transition duct 1804 to the second open end 1820 and into the interior 1803 of waste pouch 1802. As such, the waste CW is collected in waste pouch 1802 starting at the bottom portion 1801 of the waste pouch, and waste pouch 1802 accordingly fills from the bottom up.

As will readily be understood from the foregoing description and FIG. 24, to assemble waste collection system 2400 for collection of waste from body 20 of patient P, stoma 10 first must be formed in body 20. Stoma 10 may be pre-existing, i.e., patient P may have used other systems for collecting waste before using waste collection system 2400, or stoma 10 may be newly formed for use with system 2400. As previously described, stoma 10 and stoma site 12 are formed by pulling a portion of lower GI organ 22 through abdominal wall 24 to outer surface 26 of body 20, such that the pulled-through portion is external portion 28 of organ 22. Then, device 2100, in its insertion position, is inserted into stoma 10 such that distal end 2102 of device 2100 is positioned at organ 22 to receive waste from the organ. Sealing mechanism 2150 is deployed, e.g., by inflating a sealing balloon, to place sealing mechanism 2150 in its sealing position and thereby seal stoma 10 from the passage of waste through the stoma rather than tube 2106. The sealing mechanism 2150 also helps retain the device 2100 within stoma 10. Waste may then move from organ 22 through path 2108 formed by tube 2106 and transition duct 1804 of device 2150. In some embodiments, the device 2100 may include a valve such as valve 134 described with respect to device 100 to arrest the movement of waste, e.g., until a collection apparatus is connected to device 2100.

To connect collection apparatus 1800 to device 2100, connection component 1900 is positioned at barrier 2126 of device 2100. In some embodiments, the connection component 1900 is positioned with its opening around stoma site 12 before device 2100 is inserted into stoma 10, e.g., such that a portion of barrier 2126 overlaps barrier 1908 of connection portion 1900. In other embodiments, such as the embodiment shown in FIGS. 23 and 24, connection portion 1900 is positioned after device 2100 is inserted into stoma 10. Transition duct 1804 is positioned in waste pouch 1802 and connector 1808 of collection apparatus 1800 interfaces or mates with connection portion 1902 of connection component 1900 to connect the apparatus 1800 to connection component 1900 and thereby position waste pouch 1802 in communication with tube 2106 and transition duct 1804 of device 2100. If provided, the attachment mechanism(s) of apparatus 1800 may be attached to a support for supporting collection apparatus 1800; the attachment mechanism(s)

may be attached to the support before or after the connector 1808 is connected to the connection component 1900. Waste may then move through tube 2106, transition duct 1804, and into the bottom portion 1801 of waste pouch 1802. When waste pouch 1802 is full, or when the movement of waste has stopped, connector 1808 may be disconnected and waste pouch 1802 emptied or discarded.

Figure 25:
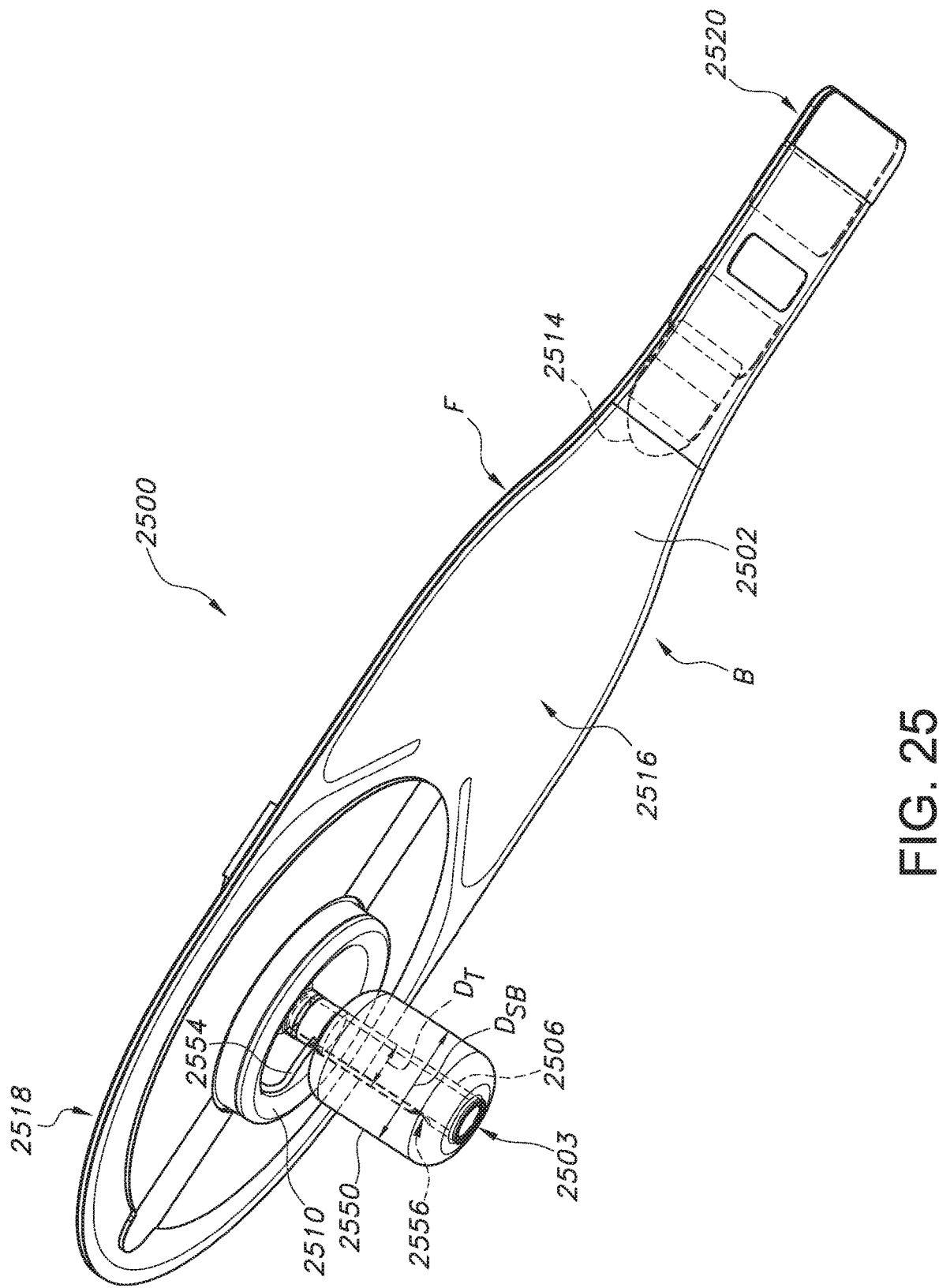
FIG. 25 provides a back, perspective view of a waste collection system for the collection of waste from a gastrointestinal organ of a patient, according to an exemplary embodiment of the present subject matter, in which a sealing mechanism of the system is in a sealing position.
Figure 26:
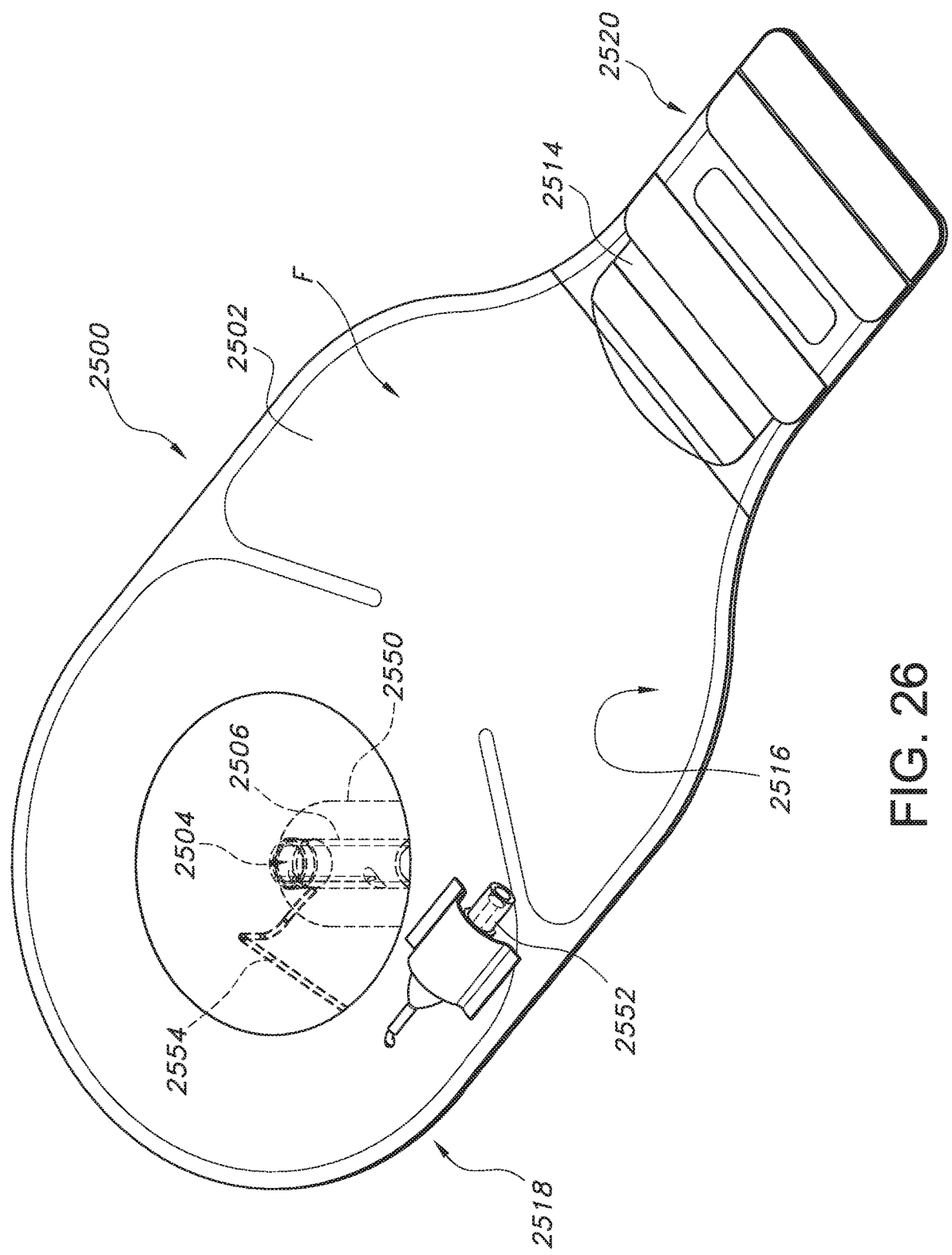
FIG. 26 provides a front, perspective view of the waste collection system of FIG. 25.
Figure 27:
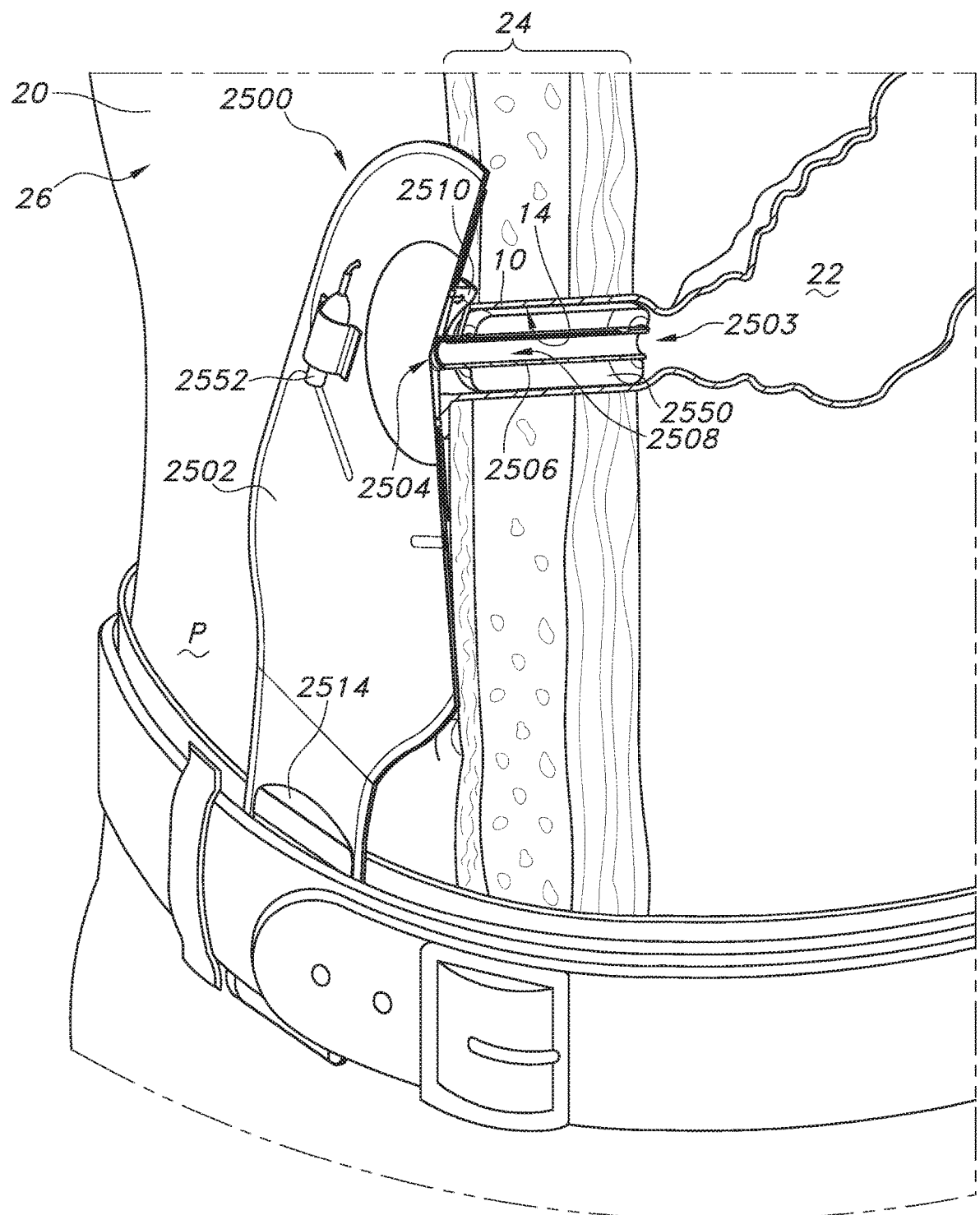
FIG. 27 provides a cross-section view of the waste collection system of FIGS. 25 and 26 assembled for the collection of waste from a gastrointestinal organ of a patient, according to an exemplary embodiment of the present subject matter.

Referring now to FIGS. 25 through 27, various views are provided of a waste collection system according to another exemplary embodiment of the present subject matter. As shown in FIGS. 25 through 27, the exemplary waste collection system 2500 includes a device for insertion within a stoma formed within a patient's body and a waste collection apparatus as generally described above with respect to FIGS. 1-24. However, the device and collection apparatus of waste collection system 2500 are one integral piece; that is, the device is integrated with the collection apparatus such that the system 2500 is a single piece waste collection system.

Turning to FIG. 25, a back perspective view is provided of the exemplary waste collection system 2500. As illustrated, the system 2500 includes a waste collection bag or pouch 2502 similar to the waste pouches 202, 1202, and 1802 described above. For instance, as described in greater detail with respect to other waste bags or pouches, the waste bag or pouch 2502 may be formed from a nonwoven material, such as an SMS material, and may include one or more layers or coatings, e.g., a liquid impervious film and/or a coating selectively permeable to one or more gases, to help control odors, wet spots, irritation, or other undesirable conditions that could occur when waste pouch 2502 receives waste. As further shown in FIG. 25, the system 2500 includes a tube 2506 defining an axial direction A. The tube 2506 extends between a distal end 2503 and a proximal end 2504. The waste pouch 2502 is integrally connected to the tube 2506 at its proximal end 2504, i.e., the waste collection pouch 2502 is integrally formed with the tube 2506 such that the pouch and tube are inseparable. As shown in FIG. 25, the tube 2506 extends from a back B of the waste pouch 2502.

The tube 2506 defines a path 2508 for movement of waste or effluent through a stoma 10 (FIG. 27) defined in the body 20 of a patient P. The tube 2506 has a length $L_T$ and an outer diameter $D_T$. As described with respect to other devices, the tube 2506 may be tapered from one of ends 2503, 2504 toward the other end, may have a varying outer diameter $D_T$ along its length $L_T$, or may have a constant outer diameter $D_T$ from one end 2503, 2504 to the other. The tube 2506 may be rigid, flexible, or fully or partially collapsible; expandable, non-expandable, or partially expandable; soft or hard; or any appropriate combination of the foregoing. Moreover, tube 2506 may be relatively thin walled, e.g., to permit as large of an inner diameter and/or cross-sectional area as possible for the movement of waste through tube 2506. Tube 2506 may have other configurations as well.

As depicted in FIG. 25, a barrier 2510 is defined at the proximal end 2504 of the tube 2506. The waste pouch 2502 is integrally connected with the barrier 2510 to form the integral, single piece system 2500. Moreover, the waste collection system 2500 includes a sealing mechanism 2550. The sealing mechanism 2550 has an insertion position and a sealing position; the sealing mechanism is shown in the sealing position in FIGS. 25 and 26. Further, as most clearly illustrated in FIG. 25, the sealing mechanism 2550 extends axially along at least a portion $L_S$ of the length $L_T$ of the tube 2506 between the proximal end 2504 and the distal end 2503 of the tube 2506. In the depicted embodiment, the sealing mechanism 2550 extends over almost the entire length $L_T$ of tube 2506 such that the device 2500 includes a sealing mechanism 2550 along an extended axial length of tube 2506.

Additionally, in the depicted embodiment, sealing mechanism 2550 is an inflatable balloon or cuff, which is deflated in the insertion position of the sealing mechanism 2550 and inflated in the sealing position of the sealing mechanism 2550, similar to the inflatable sealing mechanisms described above. In an exemplary embodiment of an inflatable sealing balloon 2550, the balloon is a Microcuff® balloon. More particularly, as previously described, the inflatable balloon or cuff forming the sealing mechanism 2550 may be fashioned of a thin film and designed to be a thin-wall, high-volume, low-pressure cuff. In some embodiments, the diameter of a thin-wall, high-volume, low-pressure cuff in a freely deployed state appreciably exceeds the diameter of the stoma into which the tube 2506 is inserted. In other embodiments, the sealing balloon has an inflated diameter $D_{SB}$ that is from about 1.1 times to about twice the diameter $D_T$ of tube 2506, and in particular embodiments, the inflated diameter $D_{SB}$ is from about 1.2 times to about 1.5 times the outer diameter $D_T$ of tube 2506. Thin-wall, high-volume, low-pressure balloons or cuffs are described in more detail above.

In embodiments in which the sealing mechanism 2550 is a sealing balloon, an inflation valve 2552 and an inflation line 2554 may be provided for inflating the sealing balloon. As shown in FIGS. 25 and 26, the inflation line 2554 may extend through the stoma 10 between the sealing balloon 2550 and the tube 2506 to inflation valve 2552 positioned on a front F of the waste pouch 2502. Other configurations of inflation valve 2552 and inflation line 2554 also may be used, e.g., inflation line 2554 may be incorporated into tube 2506. It also will be readily understood by those of ordinary skill in the art that other sealing mechanisms 2550 than an inflatable sealing balloon may be used as well, such as a flexible diaphragm or other mechanical means of retention and sealing along a length $L_S$ of the tube 2506 within stoma 10. Further, in some embodiments, the waste collection system 2500 may include a retention mechanism at the distal end 2503 of the tube 2506, similar to the retention mechanisms 120 and 1120 described above; the retention mechanism may be included in addition to the sealing mechanism 2550 or as an alternative to the sealing mechanism 2550.

Referring to FIGS. 25 and 26, the waste collection system 2500 includes one or more attachment mechanisms 2514 for attaching system 2500 to a support. Such attachment mechanisms are described above with respect to other collection apparatus. For example, using attachment mechanism(s) 2514, waste collection system 2500 may be attached to a support or support structure—such as, e.g., the patient's clothing or a healthy portion of the patient's body away from the stoma—that can help support the weight of system 2500, particularly when it is filled with waste. Attachment mechanism(s) 2514 may be coupled to an outer surface 2516 of waste pouch 2502 using any appropriate fastener or fastening mechanism, or may be incorporated into an end portion 2520 of the waste pouch 2502. For instance, the waste pouch 2502 may be integrally connected to the tube 2506 at or near a first end 2518 of the waste pouch 2502, and the attachment mechanism(s) 2514 may be defined at an opposite, second end 2520 of the waste pouch 2502, e.g., to support the waste pouch 2502 at a location away from the stoma. Attachment mechanism(s) 2514 may be any appropriate mechanism for attaching waste collection system 2500 to a support. For example, each attachment mechanism 2514 may be a stretchable, elastic loop; a hook-and-loop type fastener; an adhesive; a molded plastic clip; a loop defined in waste pouch 2502; or any other appropriate mechanism for attaching system 2500 to a support. In some embodiments, multiple attachment mechanisms 2514 are used, and each attachment mechanism 2514 may be of the same type or multiple types of attachment mechanisms 2514 may be used.

Turning to FIG. 27, a partial cross-sectional view is provided of the waste collection system 2500 positioned in a stoma formed in a patient's body. As shown in FIG. 27, the exemplary waste collection system 2500 is positioned to collect waste from lower GI organ 22 of the patient P through stoma 10, which may be formed as previously described. More particularly, the tube 2506 of system 2500 is inserted into stoma 10 such that distal end 2503 of tube 2506 is positioned at or within lower GI organ 22. The barrier 2510 at the proximal end 2504 of tube 2506 is positioned on the outer surface 26 of the patient's body 20, e.g., the barrier 2510 may be positioned over the external portion 28 of lower GI organ 22 such that the barrier 2510 covers the external portion 28. Waste pouch 2502 integrally attached to the tube 2506 at barrier 2510 is thereby positioned to receive a flow of waste from organ 22 through tube 2506.

It will be appreciated that, when waste collection system 2500 is inserted into stoma 10, the sealing mechanism 2550 is in its insertion position, in which the sealing mechanism 2550 generally conforms to the outer diameter $D_T$ of the tube 2506 or assumes a position in which the sealing mechanism 2550 is smaller than the outer diameter $D_T$ of the tube 2506. Once the device 2500 is inserted into stoma 10 such that the tube 2506 is positioned within stoma 10, the sealing mechanism 2550 may be deployed such that the sealing mechanism is in its sealing position as shown in FIG. 27. In the depicted embodiment, sealing mechanism 2550 is an inflatable balloon or cuff that is inflated to retain device 2500 within stoma 10 and to seal stoma 10 against leakage of waste around tube 2506, e.g., such that waste moves only out of tube 2506 and into waste pouch 2502. More specifically, a fluid (such as, e.g., air or a saline solution) may be introduced to sealing balloon 2550 through inflation valve 2552 and inflation line 2554 to inflate sealing balloon 2550. When inflated, i.e., when in the sealing position and inflated to its inflated diameter $D_{SB}$, the sealing balloon 2550 expands against a surface 14 of the stoma 10 such that the sealing balloon 2550 contacts stoma 10 to create an effective seal and thereby reduce leakage around the sealing balloon. As described above, the inflated diameter $D_{SB}$ of sealing balloon 2550 is greater than the diameter $D_T$ of tube 2506, and in some embodiments, the inflated diameter $D_{SB}$ may be about 1.2 to about 1.5 times greater than the tube diameter $D_T$. Further, as previously stated, the sealing balloon 2550 may be a thin-wall, high-volume, low-pressure cuff, which may effectively seal stoma 10 without imparting too great a pressure to the tissue forming stoma 10. Additionally, as shown in FIG. 25, the sealing mechanism 2550 extends along substantially the entire length $L_T$ of tube 2506. As such, the sealing mechanism 2550 may have an extended axial length $L_S$, e.g., compared to retention mechanisms 120, 1120 described above.

In the exemplary embodiment of FIG. 27, the attachment mechanism 2514 included at the second end 2520 of waste pouch 2502 is a piece of material that wraps around the patient's belt and attaches to waste pouch 2502. Thus, the patient's belt and pants, as well as the patient's body against which the waste pouch 2502 rests, help support the waste pouch 2502. In other embodiments, different and/or additional attachment mechanisms 2514 may be included, as generally described above. The attachment mechanism(s) 2514 may permit some flexibility as to where waste pouch 2502 is supported. Preferably, the configuration of attachment mechanism(s) 2514 and waste pouch 2502 permits waste pouch 2502 to be supported away from stoma site 12, e.g., to minimize irritation of and wear on stoma 10.

To position waste collection system 2500 for collection of waste from body 20 of patient P, stoma 10 first must be formed in body 20. Stoma 10 may be pre-existing, i.e., patient P may have used other systems for collecting waste before using waste collection system 2500, or stoma 10 may be newly formed for use with system 2500. As previously described, stoma 10 and stoma site 12 are formed by pulling a portion of lower GI organ 22 through abdominal wall 24 to outer surface 26 of body 20, such that the pulled-through portion is external portion 28 of organ 22. Then, tube 2506, with sealing mechanism 2550 in its insertion position, is inserted into stoma 10. As previously described, some embodiments of waste collection system 2500 also may include a retention mechanism, which also is in its insertion position when tube 2506 is inserted into stoma 10. Sealing mechanism 2550 (as well as the retention mechanism, if included) is then deployed, e.g., by inflating a sealing balloon, to place sealing mechanism 2550 in its sealing position and thereby seal stoma 10 from the passage of waste through the stoma rather than tube 2506. When the system 2500 is positioned within stoma 10 and retained by sealing mechanism 2550, the distal end 2502 of tube 2506 is positioned at organ 22 to receive waste from the organ. Waste may then move from organ 22 through path 2508 formed by tube 2506 of system 2500. In some embodiments, the system 2500 also may include a seal or valve at proximal end 2504 (e.g., seal or valve 1115) or another valve within tube 2506 (e.g., valve 134) to arrest the movement of waste until a condition is met or until a user or the patient P selects to allow the movement of waste through the tube 2506 to waste pouch 2502. That is, waste may not freely flow to waste pouch 2502 but the movement of the waste may be controlled by one or more valves within the system 2500.

Once tube 2506 is positioned in stoma 10 and sealing mechanism 2550 deployed to its sealing position, as shown in FIG. 27, waste may then move through tube 2506 and into waste pouch 2502. When waste pouch 2502 is full, or when the movement of waste has stopped, sealing mechanism 2550 may revert to its insertion position (e.g., by deflating the sealing balloon by expelling the fluid from the balloon), the tube 2506 may be removed, and waste pouch 2502 emptied or discarded.

Although device 100 is described as used with waste collection apparatus 200, device 1100 is described as used with waste collection apparatus 1200, and device 1400 is described as used with waste collection apparatus 1200, in suitable embodiments, the devices may be used with other apparatus and vice versa. For instance, in some embodiments, the device 100 may be used with waste collection apparatus 1200. Further, the teachings described with respect to, e.g., one device or apparatus may be applied to other devices or apparatus. As an example, the teachings described with respect to waste collection apparatus 1200 also may be applied to waste collection apparatus 200. Moreover, other devices and apparatus may be combined into a single unit, e.g., as described with respect to the integral transition duct and tube of device 2100 and the single piece waste collection system 2500. That is, the embodiments described herein are by way of example only and the teachings of one embodiment may be applicable to another embodiment described herein, as well as other embodiments that occur to those of ordinary skill in the art.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A waste collection apparatus for collecting waste from a body of a patient, the waste collection apparatus comprising:
   a connector having a tubular portion and a flange portion; and
   a waste pouch integrally formed with the flange portion such that the waste pouch and the connector are inseparable,
   wherein the tubular portion of the connector is configured to be inserted into a tube of a device for insertion into a stoma formed in the body of the patient.

2. A waste collection system for collecting waste from a body of a patient, the waste collection system comprising:
   a device for insertion into a stoma formed in the body of the patient, the device defining an axial direction, the device having a distal end and a proximal end spaced apart along the axial direction, the device comprising:
      a tube extending along the axial direction between the distal end and the proximal end, the tube defining a path for movement of waste, the distal end configured to be disposed within the body and the proximal end configured to be disposed outside the body; and
   a collection apparatus for collecting waste moving through the device, the collection apparatus comprising:
      a connector having a tubular portion and a flange portion, and
      a waste pouch integrally formed with the flange portion such that the waste pouch and the connector are inseparable,
   wherein the tubular portion of the connector is configured to be inserted into the proximal end of the tube of the device.

3. The waste collection system of claim 2, wherein the device further comprises:
   a sealing mechanism extending axially along an external length of the tube between the proximal end and the distal end of the tube, the sealing mechanism having an insertion position and a sealing position; and
   a retention mechanism positioned at the distal end of the tube such that the sealing mechanism is disposed between the proximal end of the tube and the retention mechanism, the retention mechanism having an insertion position and a retention position, and
   wherein the sealing mechanism is an inflatable sealing balloon, the sealing balloon deflated in the insertion position of the sealing mechanism and inflated in the sealing position.

4. The waste collection system of claim 3, wherein the sealing balloon is a thin-wall, high-volume, low-pressure cuff.

5. The waste collection system of claim 3, wherein the sealing balloon has an inflated diameter and the tube has an outer diameter, and wherein the inflated diameter of the sealing balloon is from 1.2 to 1.5 times the outer diameter of the tube.

6. The waste collection system of claim 3, wherein the retention mechanism is an inflatable retention balloon, the retention balloon deflated in the insertion position of the retention mechanism and inflated in the retention position.

7. The waste collection system of claim 6, wherein the retention balloon has an inflated diameter and the tube has an outer diameter, and wherein the inflated diameter of the retention balloon is at least twice the outer diameter of the tube.

8. The waste collection system of claim 6, further comprising a first inflation valve for inflating the sealing balloon and a second inflation valve for inflating the retention balloon.

9. The waste collection system of claim 6, further comprising an inflation valve for inflating both the sealing balloon and the retention balloon.

10. The waste collection system of claim 2, wherein the tube is a thin walled tube.

11. The waste collection system of claim 2, wherein the proximal end of the tube receives the connector to removably connect the collection apparatus to the tube.

12. The waste collection system of claim 11, wherein the connector includes a protrusion extending about an outer surface of the tubular portion, and wherein the tube includes a groove defined along an inner surface of the tube, the groove configured for receipt of the protrusion.

13. The waste collection apparatus of claim 12, wherein, distal to the protrusion, the tubular portion of the connector extends over an axial length within the tube.

14. The waste collection apparatus of claim 1, wherein the tubular portion of the connector extends over an axial length within the tube.

15. The waste collection apparatus of claim 1, wherein the flange portion of the connector defines a plane, and wherein a portion of the waste pouch integral with the flange portion extends within the plane.

16. The waste collection apparatus of claim 1, wherein the connector includes a protrusion extending about an outer surface of the tubular portion, and wherein the tube of the device includes a groove defined along an inner surface of the tube, the groove configured for receipt of the protrusion.

17. The waste collection apparatus of claim 14, wherein, distal to the protrusion, the tubular portion of the connector extends over an axial length within the tube.

18. The waste collection system of claim 2, wherein the tubular portion of the connector extends over an axial length within the tube, and wherein the tubular portion extends parallel to the tube.

19. The waste collection system of claim 2, wherein the flange portion of the connector defines a plane, and wherein a portion of the waste pouch integral with the flange portion extends within the plane.

20. The waste collection system of claim 6, wherein the retention balloon is fluidly separate from the sealing balloon.

* * * * *